US006547788B1

(12) United States Patent
Maguire et al.

(10) Patent No.: US 6,547,788 B1
(45) Date of Patent: Apr. 15, 2003

(54) MEDICAL DEVICE WITH SENSOR COOPERATING WITH EXPANDABLE MEMBER

(75) Inventors: Mark A. Maguire, San Jose, CA (US); Martin F. O'Sullivan, San Francisco, CA (US); Edward L. Carcamo, Millbrae, CA (US); Michael D. Lesh, Mill Valley, CA (US); Alan K. Schaer, San Jose, CA (US); Kevin J. Taylor, San Francisco, CA (US); Guillermo P. Picazo, San Jose, CA (US)

(73) Assignee: Atrionx, Inc., Palo Alto, CA (US)

(*) Notice: Subject to any disclaimer, the term of this patent is extended or adjusted under 35 U.S.C. 154(b) by 0 days.

(21) Appl. No.: 09/517,614

(22) Filed: Mar. 2, 2000

Related U.S. Application Data

(63) Continuation-in-part of application No. 09/199,736, filed on Nov. 25, 1998, now Pat. No. 6,117,101, which is a continuation-in-part of application No. 08/889,798, filed on Jul. 8, 1997, now Pat. No. 6,024,740.
(60) Provisional application No. 60/122,571, filed on Mar. 2, 1999, and provisional application No. 60/163,897, filed on Nov. 5, 1999.

(51) Int. Cl.[7] .............................................. A61B 18/18
(52) U.S. Cl. .......................... 606/41; 606/49; 607/102; 607/122
(58) Field of Search ...................... 606/42, 41, 34, 606/45–50; 607/96, 98, 101, 102, 122, 154, 115, 116, 119

(56) References Cited

U.S. PATENT DOCUMENTS

| 5,114,423 | A | | 5/1992 | Kasprzky et al. |
| 5,220,927 | A | | 6/1993 | Astrahan et al. |
| 5,540,679 | A | * | 7/1996 | Fram et al. ................... 606/27 |
| 5,562,720 | A | | 10/1996 | Stern et al. |
| 5,860,974 | A | * | 1/1999 | Abele .......................... 606/41 |
| 5,989,284 | A | * | 11/1999 | Laufer ......................... 607/96 |
| 6,071,278 | A | * | 6/2000 | Panescu et al. ............... 606/34 |
| 6,086,581 | A | * | 7/2000 | Reynolds et al. ............. 606/41 |
| 6,091,993 | A | | 7/2000 | Bouchier et al. |
| 6,179,835 | B1 | * | 1/2001 | Panescu et al. ............... 606/41 |

FOREIGN PATENT DOCUMENTS

| EP | 0 812 573 A2 | 12/1997 |
| WO | WO 95/10326 | 4/1995 |
| WO | WO 96/00042 | 1/1996 |
| WO | WO 99/02096 | 1/1999 |
| WO | WO 00/51683 | 9/2000 |

* cited by examiner

Primary Examiner—Roy D. Gibson
(74) Attorney, Agent, or Firm—Knobbe, Martens, Olson, & Bear LLP

(57) ABSTRACT

A tissue ablation catheter for forming a lesion along a substantially circumferential region of tissue is described. The catheter includes one or more sensors for monitoring the temperature of the tissue being ablated. The temperature sensors are mounted on the interior or exterior of an expandable member that is affixed to a shaft of the catheter.

30 Claims, 39 Drawing Sheets

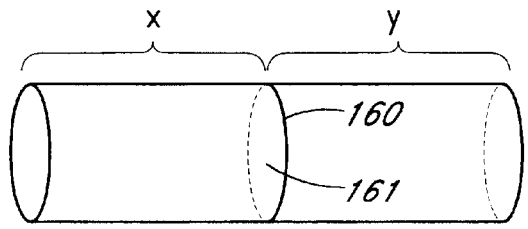
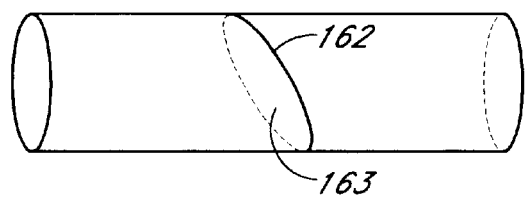
*FIG. 1A*    *FIG. 1B*
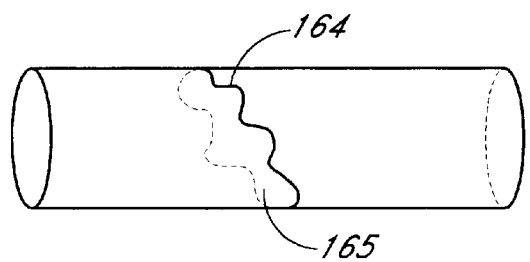
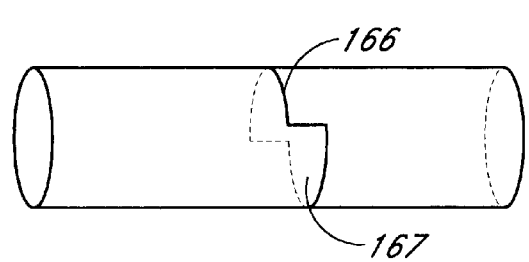
*FIG. 1C*    *FIG. 1D*

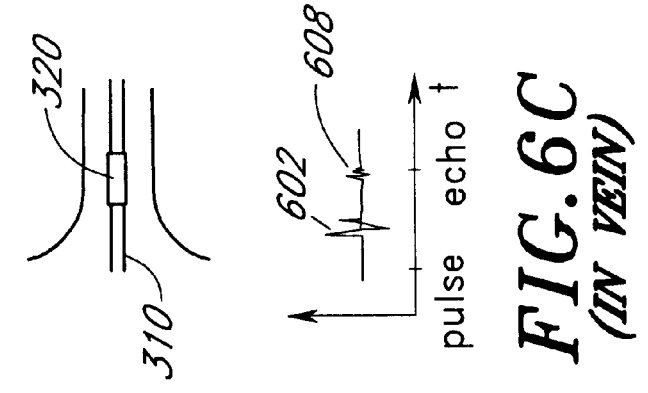
FIG. 6A (NOT IN VEIN)
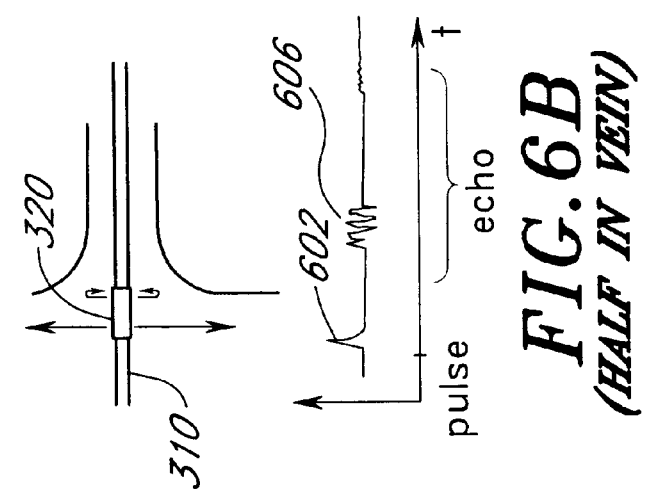
FIG. 6B (HALF IN VEIN)
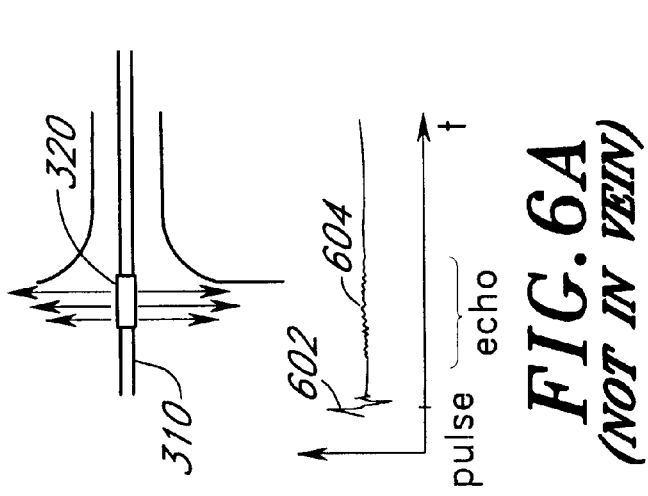
FIG. 6C (IN VEIN)
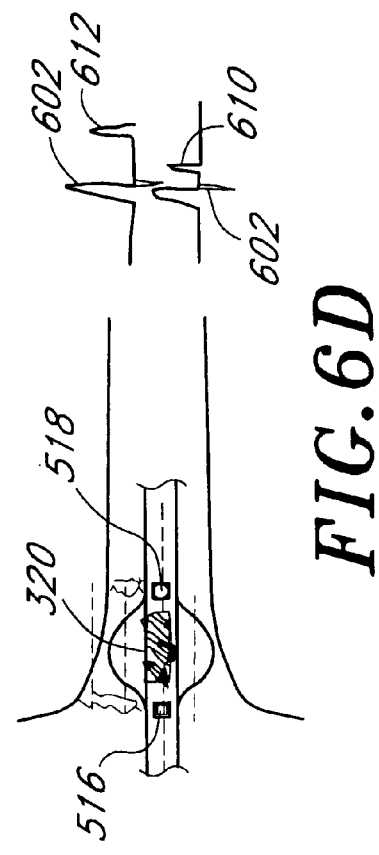
FIG. 6D

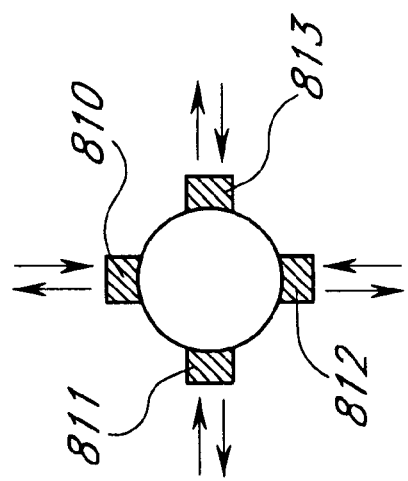
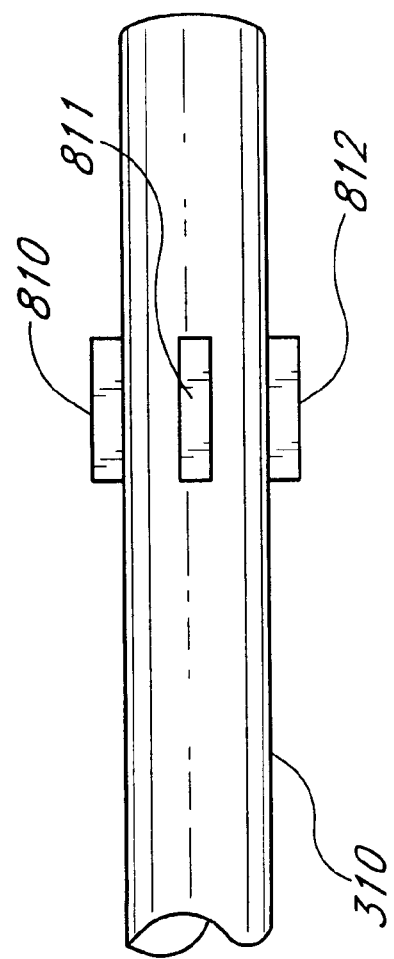

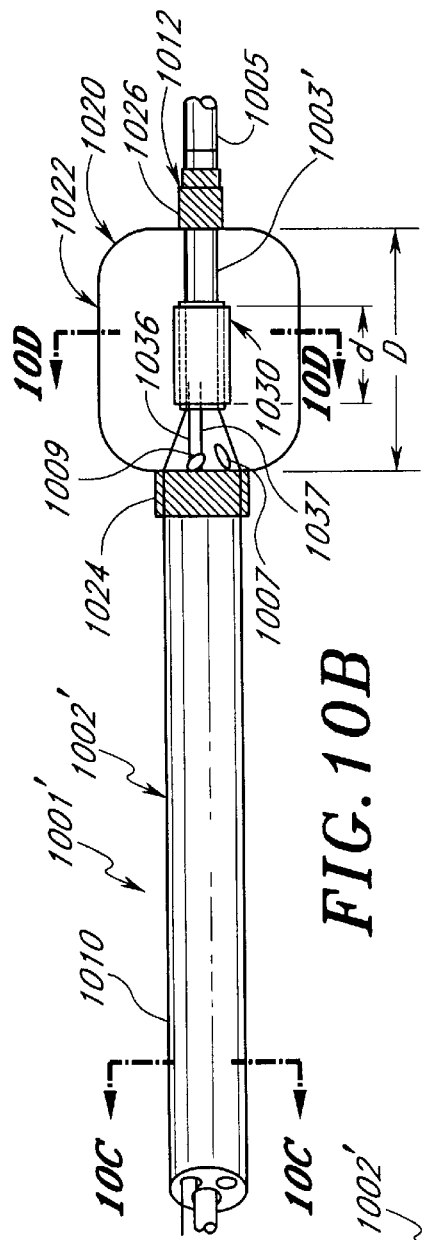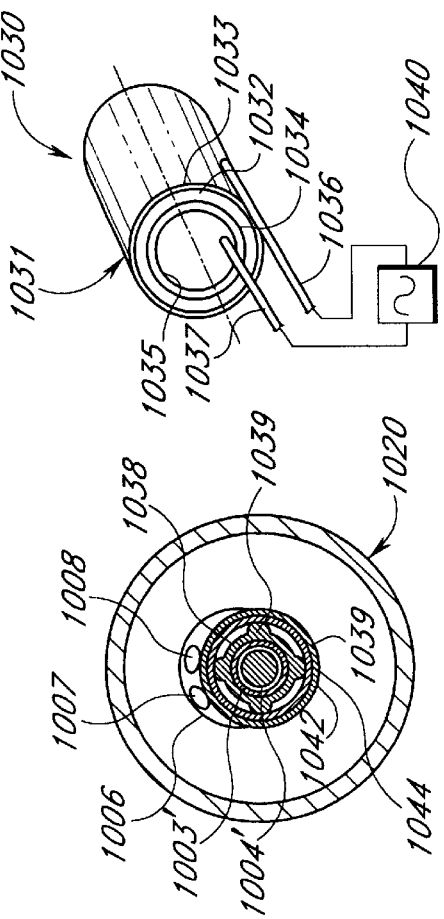

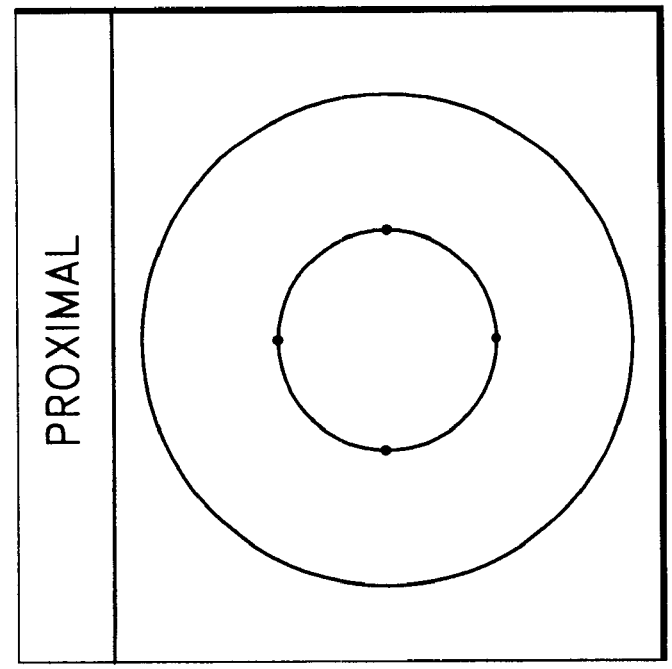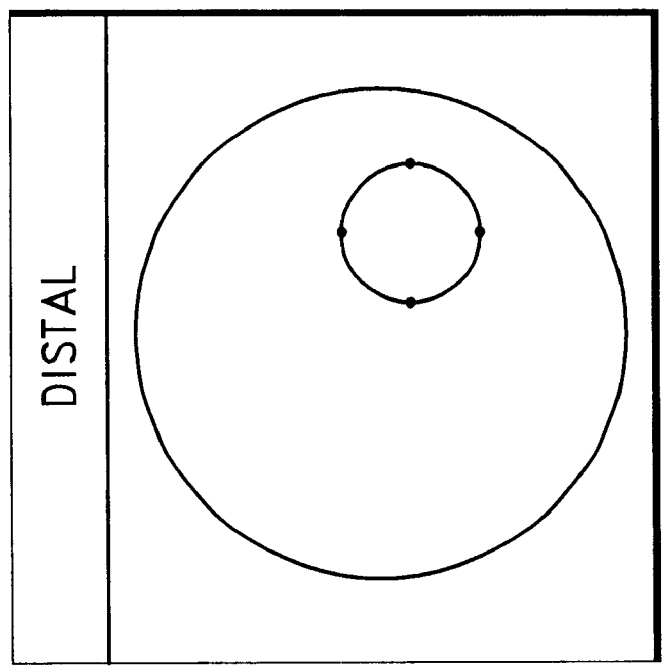
FIG. 13

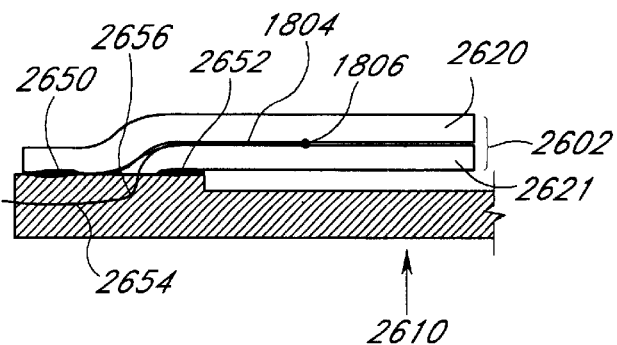
FIG.26A
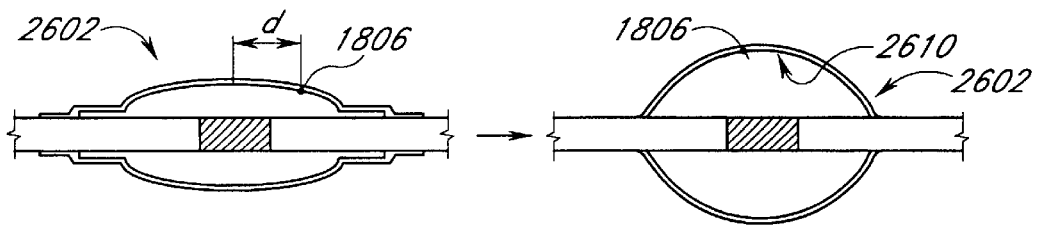
FIG.26B    FIG.26C
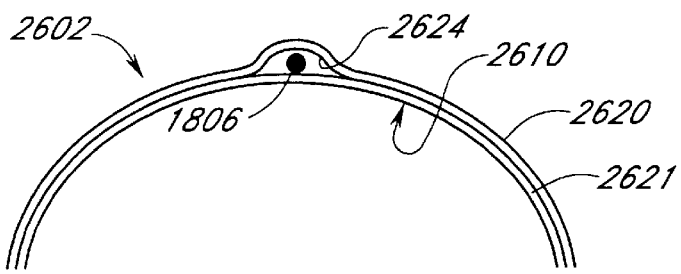
FIG.26D
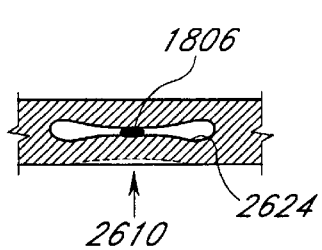 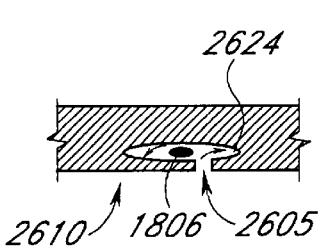 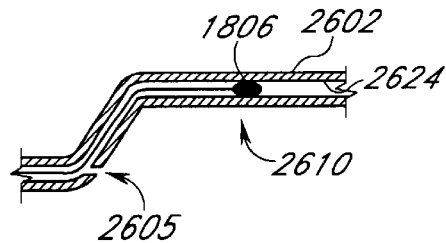
FIG.26E    FIG.26F    FIG.26G

FIG.28G
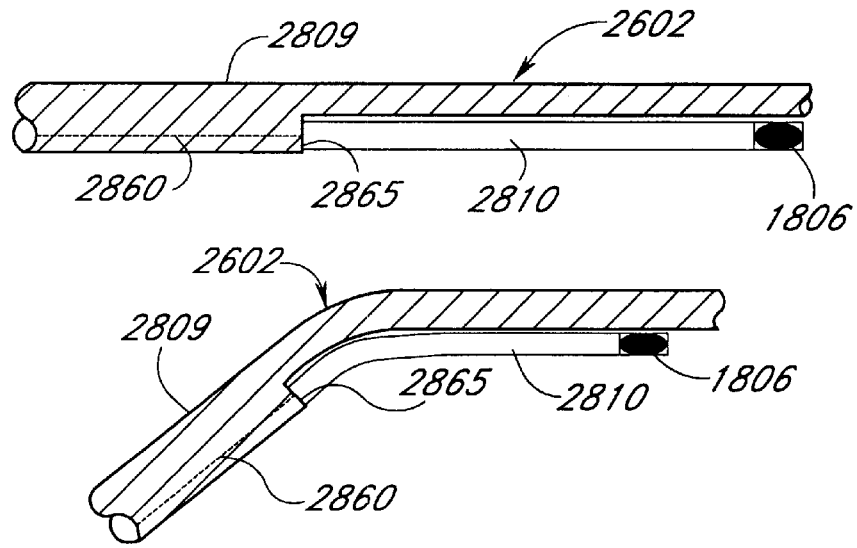
FIG.28H
FIG.29A
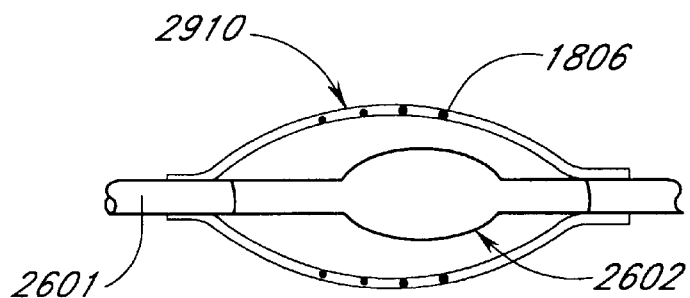
FIG.29B
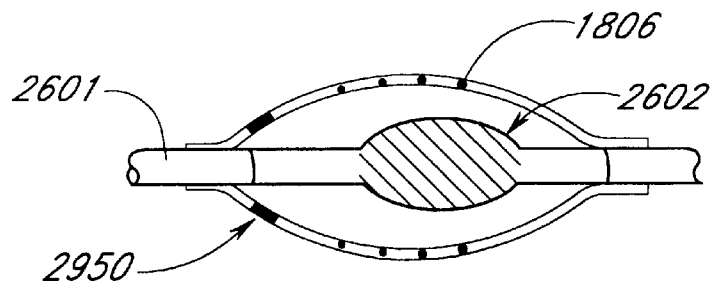

MEDICAL DEVICE WITH SENSOR COOPERATING WITH EXPANDABLE MEMBER

RELATED PATENT AND APPLICATIONS

The present application is a continuation-in-part of U.S. application Ser. No. 09/199,736, filed on Nov. 25, 1998 now U.S. Pat. No. 6,117 101 which is a continuation-in-part of U.S. application Ser. No. 08/889,798, filed on Jul. 8, 1997, now U.S. Pat. No. 6,024,740, issued Feb. 15, 2000, and claims priority under 35 U.S.C. §120 to these applications. These parent cases also are hereby incorporated by reference. In addition, the present application claims priority under 35 U.S.C. §119(e) to provisional application No. 60/122,571, filed on Mar. 2, 1999 and to provisional application No. 60/163,897, filed Nov. 5, 1999.

BACKGROUND OF THE INVENTION

1. Field of the Invention

The field of the invention relates generally to a medical device system and associated methods of manufacture and use. More particularly, the invention relates to a medical device assembly including a sensory system integrated with an expandable member of the assembly, as well as relates to associated methods of manufacturing and using the assembly.

2. Description of Related Art

Many local energy delivery devices and methods have been developed for treating the various abnormal tissue conditions in the body, and particularly for treating abnormal tissue along body space walls which define various body spaces in the body. For example, various devices have been disclosed with the primary purpose of treating or recanalizing atherosclerotic vessels with localized energy delivery. Several prior devices and methods combine energy delivery assemblies in combination with cardiovascular stent devices in order to locally deliver energy to tissue in order to maintain patency in diseased lumens such as blood vessels. Endometriosis, another abnormal wall tissue condition which is associated with the endometrial cavity and is characterized by dangerously proliferative uterine wall tissue along the surface of the endometrial cavity, has also been treated by local energy delivery devices and methods.

Several other devices and methods have also been disclosed which use catheter-based heat sources for the intended purpose of inducing thrombosis and controlling hemorrhaging within certain body lumens such as vessels. Detailed examples of local energy delivery devices and related procedures such as those of the types described above are disclosed in the following references: U.S. Pat. No. 4,672,962 to Hershenson; U.S. Pat. No. 4,676,258 to InoKuchi et al.; U.S. Pat. No. 4,790,311 to Ruiz; 4,807,620 to Strul et al.; U.S. Pat. No. 4,998,933 to Eggers et al.; U.S. Pat. No. 5,035,694 to Kasprzyk et al.; U.S. Pat. No. 5,190,540 to Lee; U.S. Pat. No. 5,226,430 to Spears et al.; and U.S. Pat. No. 5,292,321 to Lee; U.S. Pat. No. 5,449,380 to Chin; U.S. Pat. No. 5,505,730 to Edwards; U.S. Pat. No. 5,558,672 to Edwards et al.; and U.S. Pat. No. 5,562,720 to Stern et al.; U.S. Pat. No. 4,449,528 to Auth et al.; U.S. Pat. No. 4,522,205 to Taylor et al.; and U.S. Pat. No. 4,662,368 to Hussein et al.; U.S. Pat. No. 5,078,736 to Behl; and U.S. Pat. No. 5,178,618 to Kandarpa.

Other prior devices and methods electrically couple fluid to an ablation element during local energy delivery for treatment of abnormal tissues. Some such devices couple the fluid to the ablation element for the primary purpose of controlling the temperature of the element during the energy delivery. Other such devices couple the fluid more directly to the tissue device interface either as another temperature control mechanism or in certain other known applications as a carrier or medium for the localized energy delivery. Detailed examples of ablation devices which use fluid to assist in electrically coupling electrodes to tissue are disclosed in the following references: U.S. Pat. No. 5,348,554 to Imran et al.; U.S. Pat. No. 5,423,811 to Imran et al.;,U.S. Pat. No. 5,505,730 to Edwards; U.S. Pat. No. 5,545,161 to Imran et al.; U.S. Pat. No. 5,558,672 to Edwards et al.; U.S. Pat. No. 5,569,241 to Edwards; U.S. Pat. No. 5,575,788 to Baker et al.; U.S. Pat. No. 5,658,278 to Imran et al.;

U.S. Pat. No. 5,688,2,67 to Panescu et al.; U.S. Pat. No. 5,697,927 to Imran et al.; U.S. Pat. No. 5,722,403 to McGee et al.; U.S. Pat. No. 5,769,846; and PCT Patent Application Publication No. WO 97/32525 to Pomeranz et al.; and PCT Patent Application Publication No. WO 98/02201 to Pomeranz et al.

Atrial Fibrillation

Cardiac arrhythmias, and atrial fibrillation in particular, persist as common and dangerous medical ailments associated with abnormal cardiac chamber wall tissue, and are often observed in elderly patients. In patients with cardiac arrhythmia, abnormal regions of cardiac tissue do not follow the synchronous beating cycle associated with normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction is known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self propagating. In the alternative or in addition to the multiwavelet reentrant type, cardiac arrhythmias may also have a focal origin, such as when an isolated region of tissue in an atrium fires autonomously in a rapid, repetitive fashion. Cardiac arrhythmias, including atrial fibrillation, may be generally detected using the global technique of an electrocardiogram (EKG). More sensitive procedures of mapping the specific conduction along the cardiac chambers have also been disclosed, such as, for example, in U.S. Pat. No. 4,641,649 to Walinsky et al. and in PCT Patent Application Publication No. WO 96/32897 to Desai.

A host of clinical conditions can result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle which thereafter pumps the embolism into the cerebral circulation where a stroke results. Accordingly, numerous procedures for treating, atrial arrhythmias have been developed, including pharmacological, surgical, and catheter ablation procedures.

Several pharmacological approaches intended to remedy or otherwise treat atrial arrhythmias have been disclosed, such as, for example, those approaches disclosed in the following references: U.S. Pat. No. 4,673,563 to Berne et al.; U.S. Pat. No. 4,569,801 to Molloy et al.; and "Current Management of Arrhythmias" (1991) by Hindricks, et al. Such pharmacological solutions, however, are not generally believed to be entirely effective in many cases, and are even believed in some cases to result in proarrhythmia and long term inefficacy.

Several surgical approaches have also been developed with the intention of treating atrial fibrillation. One particular example is known as the "maze procedure," as is disclosed by Cox, J. L. et al. in "The surgical treatment of atrial fibrillation. I. Summary" *Thoracic and Cardiovascular Surgery* 101(3), pp. 402–405 (1991); and also by Cox, JL in "The surgical treatment of atrial fibrillation. IV. Surgical Technique", *Thoracic and Cardiovascular Surgery* 101(4), pp. 584–592 (1991). In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium. See Sueda et al., "Simple Left Atrial Procedure for Chronic Atrial Fibrillation Associated With Mitral Valve Disease" (1996).

The "maze procedure" as performed in the left atrium generally includes forming vertical incisions from the two superior pulmonary veins and terminating in the region of the mitral valve annulus, traversing the region of the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the arrhythmogenic conduction from the boxed region of the pulmonary veins to the rest of the atrium by creating conduction blocks within the aberrant electrical conduction pathways. Other variations or modifications of this specific pattern just described have also been disclosed, all sharing the primary purpose of isolating known or suspected regions of arrhythmogenic origin or propagation along the atrial wall.

While the "maze" procedure and its variations as reported by Dr. Cox and others have met some success in treating patients with atrial arrhythmia, its highly invasive methodology is believed to be prohibitive in most cases. However, these procedures have provided a guiding principle that electrically isolating faulty cardiac tissue may successfully prevent atrial arrhythmia, and particularly atrial fibrillation caused by arrhythmogenic conduction arising from the region of the pulmonary veins.

Less invasive catheter-based approaches to treat atrial fibrillation have been disclosed which implement cardiac tissue ablation for terminating arrhythmogenic conduction in the atria. Examples of such catheter-based devices and treatment methods have generally targeted atrial segmentation with ablation catheter devices and methods adapted to form linear or curvilinear lesions in the wall tissue which defines the atrial chambers. Some specifically disclosed approaches provide specific ablation elements which are linear over a defined length intended to engage the tissue for creating the linear lesion. Other disclosed approaches provide shaped or steerable guiding sheaths, or sheaths within sheaths, for the intended purpose of directing tip ablation catheters toward the posterior left atrial wall such that sequential ablations along the predetermined path of tissue may create the desired lesion. In addition, various energy delivery modalities have been disclosed for forming atrial wall lesions and include use of microwave, laser, ultrasound, thermal conduction, and more commonly, radiofrequency energies to create conduction blocks along the cardiac tissue wall. Detailed examples of ablation device assemblies and methods for creating lesions along an atrial wall are disclosed in the following U.S. Patent references: U.S. Pat. No. 4,898,591 to Jang et al.; U.S. Pat. No. 5,104,393 to Isner et al.; U.S. Pat. No. 5,427,119; U.S. Pat. No. 5,487,385 to Avitall; U.S. Pat. No. 5,497,119 to Swartz et al.; U.S. Pat. No. 5,545,193 to Fleischman et al.; U.S. Pat. No. 5,549,661 to Kordis et al.; U.S. Pat. No. 5,575,810 to Swanson et al.; U.S. Pat. No. 5,564,440 to Swartz et al.; U.S. Pat. No. 5,592,609 to Swanson et al.; U.S. Pat. No. 5,575,766 to Swartz et al.; U.S. Pat. No. 5,582,609 to Swanson; U.S. Pat. No. 5,617,854 to Munsif; U.S. Pat. No. 5,687,723 to Avitall; U.S. Pat. No. 5,702,438 to Avitall. Other examples of such ablation devices and methods are disclosed in the following PCT Patent Application Publication Nos.: WO 93/20767 to Stern et al.; WO 94/21165 to Kordis et al.; WO 96/10961 to Fleischman et al.; WO 96/26675 to Klein et al.; and WO 97/37607 to Schaer. Additional examples of such ablation devices and methods are disclosed in the following published articles: "Physics and Engineering of Transcatheter Tissue Ablation", Avitall et al., *Journal of American College of Cardiology*, Volume 22, No. 3:921–932 (1993); and "Right and Left Atrial Radiofrequency Catheter Therapy of Paroxysmal Atrial Fibrillation," Haissaguerre, et al., *Journal of Cardiovascular Electrophysiology* 7(12), pp. 1132–1144 (1996).

In addition to those known assemblies summarized above, additional tissue ablation device assemblies have been recently developed for the specific purpose of ensuring firm contact and consistent positioning of a linear ablation element along a length of tissue by anchoring the element at,least at one predetermined location along that length, such as in order to form a "maze"-type lesion pattern in the left atrium. One example of such assemblies is that disclosed in U.S. Pat. No. 5,971,983, issued Oct. 26, 1999, which is hereby incorporated by reference. The assembly includes an anchor at each of two ends of a linear ablation element in order to secure those ends to each of two predetermined locations along a left atrial wall, such as at two adjacent pulmonary veins, so that tissue may be ablated along the length of tissue extending therebetween.

In addition to attempting atrial wall segmentation with long linear lesions for treating atrial arrhythmia, other ablation device and method have also been disclosed which are intended to use expandable members such as balloons to ablate cardiac tissue. Some such devices have been disclosed primarily for use in ablating tissue wall regions along the cardiac chambers. Other devices and methods have been disclosed for treating abnormal conduction of the left-sided accessory pathways, and in particular associated with "Wolff-Parkinson-White" syndrome—various such disclosures use a balloon for ablating from within a region of an associated coronary sinus adjacent to the desired cardiac tissue to ablate. Further more detailed examples of devices and methods such as of the types just described are variously disclosed in the following published references: Fram et al., in "Feasibility of RF Powered Thermal Balloon Ablation of Atrioventricular Bypass Tracts via the Coronary Sinus: In vivo Canine Studies," *PACE*, Vol. 18, p 1518–1530 (1995); "Long-term effects of percutaneous laser balloon ablation from the canine coronary sinus", Schuger CD et al., *Circu-*

*lation* (1992) 86:947–954; and "Percutaneous laser balloon coagulation of accessory pathways", McMath LP et al., Diagn Ther Cardiovasc Interven 1991; 1425:165–171.

Arrhythmias Originating from Foci in Pulmonary Veins

Various modes of atrial fibrillation have also been observed to be focal in nature, caused by the rapid and repetitive firing of an isolated center within cardiac muscle tissue associated with the atrium. Such foci may act as either a trigger of atrial fibrillatory paroxysmal or may even sustain the fibrillation. Various disclosures have suggested that focal atrial arrhythmia often originates from at least one tissue region along one or more of the pulmonary veins of the left atrium, and even more particularly in the superior pulmonary veins.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to terminate the inappropriate arrhythmogenic conduction.

One example of a focal ablation method intended to treat focal arrhythmia originating from a pulmonary vein is disclosed by Haissaguerre, et al. in "Right and Left Atrial Radiofrequency Catheter Therapy of Paroxysmal Atrial Fibrillation" in *Journal of Cardiovascular Electrophysiology* 7(12), pp. 1132–1144 (1996). Haissaguerre, et al. discloses radiofrequency catheter ablation of drug-refractory paroxysmal atrial fibrillation using linear atrial lesions complemented by focal ablation targeted at arrhythmogenic foci in a screened patient population. The site of the arrhythmogenic foci were generally located just inside the superior pulmonary vein, and the focal ablations were generally performed using a standard 4 mm tip single ablation electrode.

Another focal ablation method of treating atrial arrhythmias is disclosed in Jais et al., "A focal source of atrial fibrillation treated by discrete radiofrequency ablation," *Circulation* 95:572–576 (1997). Jais et al. discloses treating patients with paroxysmal arrhythmias originating from a focal source by ablating that source. At the site of arrhythmogenic tissue, in both right and left atria, several pulses of a discrete source of radiofrequency energy were applied in order to eliminate the fibrillatory process.

Other assemblies and methods have been disclosed addressing focal sources of arrhythmia in pulmonary veins by ablating circumferential regions of tissue either along the pulmonary vein, at the ostium of the vein along the atrial wall, or encircling the ostium and along the atrial wall. More detailed examples of device assemblies and methods for treating focal arrhythmia as just described are disclosed in PCT Patent Application Publication No. WO 99/02096 to Diederich et al., and also in the following pending U.S. Patent Applications: U.S. Ser. No. 08/889,798 for "Circumferential Ablation Device Assembly" to Michael D. Lesh et al., filed Jul. 8, 1997, now U.S. Pat. No. 6,024,740, issued Feb. 15, 2000; U.S. Ser. No. 08/889,835 for "Device and Method for Forming a Circumferential Conduction Block in a Pulmonary Vein" to Michael D. Lesh, filed Jul. 8, 1997; U.S. Ser. No. 09/199,736 for "Circumferential Ablation Device Assembly" to Chris J. Diederich et al., filed Feb. 3, 1998; and U.S. Ser. No. 09/260,316 for "Device and Method for Forming a Circumferential Conduction Block in a Pulmonary Vein" to Michael D. Lesh.

Another specific: device assembly and method which is intended to treat focal atrial fibrillation by ablating a circumferential region of tissue between two seals in order to form a conduction block to isolate an arrhythmogenic focus within a pulmonary vein is disclosed in U.S. Pat. No. 5,938,660 and a related PCT Patent Application Publication No. WO 99/00064.

Thermocouples have been used with prior ablation catheter to monitor and regulate the ablation process. A difficulties arises, however, with monitoring and regulating the ablation process with one or more thermocouples where ablation occurs though an inflatable balloon, such as with the device, assembly disclosed in PCT Patent Application Publication No. WO 99/02096 to Diederich et al. Thermocouples are usually mounted to the catheter shaft, and if ablation occurs at an interface between the balloon and the tissue which it engages, the thermocouples do not accurately measure the temperature because of their remote distance relative to the ablation site. Accordingly, a need exists for an improved approach for mounting a thermocouple onto a catheter in proximity to the ablation site.

SUMMARY OF THE INVENTION

In one mode, the present invention provides a medical device system for ablating a circumferential region of tissue in order to form a circumferential conduction block at a location where a pulmonary vein extends from an atrium in a patient's heart. Such conduction block may be formed in order to, for example: electrically isolate a focal source of arrhythmia in the pulmonary vein from the rest of the atrium; or connect linear lesions such that a pattern of conduction blocks may be formed to isolate a posterior region of the atrial wall from the rest of the atrium.

In one aspect, the tissue ablation apparatus of the present invention ablates a substantial portion of a circumferential region of tissue at a location in a patient's body where a pulmonary vein extends from an atrium in a patient. The ablation apparatus includes an elongate body with a proximal end portion and a distal end portion. An ablation member is coupled to the elongate body. The ablation member comprises an expandable member coupled to the distal end portion of the elongate body, wherein the expandable member is adjustable from a collapsed position to an expanded position. The expandable member is adapted to engage the substantial portion of the circumferential region of tissue when in the expanded position. The ablation member also has an ablation element that is adapted to ablate at least a portion of the substantial portion of the circumferential region of tissue. The ablation member further includes a sensor that is coupled to the expandable member at a location at least when the expandable member is in the expanded position. A conductor is coupled to the sensor in a manner that does not substantially affect the adjustment of the expandable member from the collapsed positioned to an expanded position. In a preferred form, the conductor also is coupled to a coupler at the proximal end portion of the elongated body.

In one variation of the ablation apparatus, the expandable member includes an inflatable balloon. The expandable member may be coupled to the elongate body by an adhesive. Further, the adhesive may encapsulate the sensor. A variety of ways are disclosed for reducing tension on the location where the sensor is coupled to the expandable member. For example, the wire may form a loop or a helix to reduce tension on the attachment point.

In one embodiment, the expandable member has an outer surface that is adapted to contact the substantial portion of the circumferential region of tissue along an ablative path when the expandable member is adjusted to the expanded position. The location where the sensor is coupled to the expandable member may be provided along the outer surface. Alternatively, the expand able member may have an inner surface and an outer surface, wherein the outer surface is adapted to contact the substantial portion of the circumferential region of tissue, and wherein the location, at which the sensor is coupled to the expandable member, is provided along the inner surface of the expandable member.

In one preferred embodiment, the sensor comprises a temperature sensor. The sensor may be coupled to the expandable member at a location which is fixed along the ablative path. In the alternative or in addition, the sensor may comprise an electrode.

In another variation of the present invention, the expandable member may include an outer layer and an inner layer, wherein the outer layer comprises an outer surface that is adapted to contact the substantial portion of the circumferential region of tissue. The sensor may be disposed between the outer and inner layers in such an embodiment. In a further variation, a passageway may be provided between the outer layer and the inner layer, wherein the sensor is slideably engaged within the passageway. The passageway may be filled with a fluid. Alternatively, the passageway may be incorporated into the elastomeric wall of the expandable member, wherein the sensor and conductor are slideably engaged within the channel. In one variation, the expandable member has an interior space which is in fluid communication with the passageway in order to facilitate adjustment of the expandable member from a collapsed to an expanded state. In another variation, the passageway may include a stenting member to prevent the passageway from collapsing under pressure from the interior of the expandable member.

In another preferred embodiment, the coupling location on the expandable member further comprises a reinforcement disposed on either the inner or outer surface of the expandable member.

In one additional variation, the expandable member of the present invention may comprise a spline to which the sensor is coupled, the spline being expandable or self-expanding. In some cases, the apparatus may include both an inflatable balloon and a spline, wherein the coupling location for the sensor is located along the spline.

The apparatus of the present invention preferably includes an ultrasound transducer adapted to emit a circumferential path of ultrasound ablative energy. The sensor may be positionable within the circumferential path when the expandable member is in the expanded position.

Also disclosed is a method of monitoring the ablation of a substantial portion of a circumferential region of tissue at a location where a pulmonary vein extends from an atrium. The method involves positioning an ablation member, which has an ablation element, along the location where the pulmonary vein extends from the atrium. The ablation element is activated to ablate the substantial portion of the circumferential region of tissue. This can be done simultaneously or through a sequential series of ablation steps (temporal and/or spatial). Temperature is monitored along the substantial portion of the circumferential region of tissue. The ablation element is deactivated when the temperature along the substantial portion of the circumferential region of tissue has reached either a first predetermined value or a second predetermined valve for a predetermined period of time. The initial act of positioning may further comprise adjusting an expandable member from a collapsed position to an expanded position, such that at least a portion of the expandable member contacts the substantial portion of the circumferential region of tissue. In a further variation, when the expandable member is adjusted from the collapsed position to the expanded position, a sensor, which is coupled to the expandable member, is preferably placed sufficiently close to the substantial portion of the circumferential region of tissue to allow the sensor to monitor the temperature of the substantial portion of the circumferential region of tissue.

While various aspects and features of the present invention have particular utility in the context of tissue ablation, apparatuses and ablation processes, such aspects and features also can be practiced apart from such devices and methods. Thus, in accordance with another mode of the present invention, a medical article is provided comprising an elongate body with a proximal end portion and a distal end portion. An expandable member is coupled to the distal end portion of the elongate body, and the expandable member is adapted to be adjusted between a collapsed position and an expanded position. A sensor is coupled to the expandable member at a location at least when the expandable member is in the expanded position, and a conductor is coupled to the sensor in a manner that does not substantially affect the adjustment of the expandable member from the collapsed position to the expanded position. In a preferred form, the conductor is also coupled to a coupler at the proximal end portion of the elongated body.

The present invention also involves methods of manufacturing the medical apparatuses described herein. In one mode, the method involves inverting an expandable member, coupling the sensor to the expandable member, and then returning the expandable member to its normal position. One or more ends of the expandable member can be attached to an elongated body of the medical apparatus after the sensor is coupled to the expandable member. In one variation, one end of the expandable member is attached to the elongated body before the expandable member is inverted.

In another mode, an end of the sensor is formed to have a larger sized shape than a conductor to which it is attached. In one form, for example, the sensor is shaped to have a loop configuration and in another form the sensor is shaped to have a serpentine configuration. The sensor is embedded in a bonding agent affixed to the expandable member or within the material of the expandable member itself.

In an additional mode, the expandable member is formed with at least one reinforcement location. The location(s) can be formed on inner or outer sides of the expandable member. The sensor is coupled to the expandable member at the reinforcement location.

In a further manufacturing mode, the expandable member is formed with a passageway. The sensor and/or a conductor, which is connected to the sensor, is slideably inserted within or through the passageway.

These manufacturing methods, as well as others described herein, can be used to coupled the sensor to the expandable member so as to position the sensor in a desired location when the expandable member is adjusted to an expanded position, but not to substantially affect such adjustment (e.g., affect the shape of the expandable member when in the expanded position and/or impede the adjustment of the expandable member to the expanded position).

Further aspects, features and advantages of the present invention will also become apparent from the following description of preferred embodiments of the invention.

BRIEF DESCRIPTION OF THE DRAWINGS

The advantages and features of the disclosed invention will readily be appreciated by persons skilled in the art from the following detailed description when read in conjunction with the drawings listed below.

FIG. 1A shows an example of a circular ablation path.

FIG. 1B shows an example of an elliptical ablation path.

FIG. 1C shows an example of an irregular ablation path.

FIG. 1D shows an example of a stepped ablation path.

FIG. 6A shows a downrange time-domain response of a single-transducer ultrasonic sensing system when the transducer is positioned in the atrium.

FIG. 6B shows a downrange time-domain response of a single-transducer ultrasonic sonar system when the transducer is partially inserted into the ostium.

FIG. 6C shows a downrange time-domain response of a single-transducer ultrasonic sonar system when the transducer is fully inserted into the ostium.

FIG. 6D shows a downrange time-domain response of a multi-transducer ultrasonic sensing system when a proximal ultrasonic transducer is not positioned in the ostium and a distal transducer is positioned in the ostium.

FIG. 8A is a side view of an array of ultrasonic transducers disposed around a catheter, and M FIG. 8B is a cross-sectional view of the catheter shown in FIG. 8A and illustrates ultrasonic wavefronts produced by the array of ultrasonic transducers.

FIG. 10B shows a partial side elevational view of a circumferential ablation catheter for use with a position monitoring system, and shows the ablation element to include a single cylindrical ultrasound transducer, such as that illustrated in FIG. 10A, which is positioned along an inner member within an expandable balloon that is shown in a radially expanded condition.

FIG. 10C shows a transverse cross-sectional view of the circumferential ablation catheter shown in FIG. 10B taken along line 10C—10C shown in FIG. 10B.

FIG. 10D shows a transverse cross-sectional view of the circumferential ablation catheter shown in FIG. 10B taken along line 10D—10D shown in FIG. 10B.

FIG. 10E shows a perspective view of the ultrasonic transducer of FIG. 10B in isolation, similar to that shown in FIG. 10A, and further shows electrical leads coupled to the transducer.

FIG. 10F shows a modified version of the ultrasonic transducer of FIG. 10E with individually driven sectors.

FIG. 13 shows a display produced by data from a skew-sensing catheter.

FIGS. 16D–E respectively show sequential modes of using another ablation catheter in a partially segmented view of a left atrium and pulmonary veins similar to that shown in FIGS. 16A–B, wherein FIG. 16D shows a circumferential ablation member having a balloon inflated and positioned within the left atrium, and wherein FIG. 16E shows the ablation member after being advanced with the balloon inflated until being positioned at a desired location wherein the expanded balloon engages the pulmonary vein, the vein ostium, and a region of tissue along the posterior left atrial wall surrounding the ostium (FIG. 16E).

FIG. 26A shows an enlarged cross-sectional view of a thermocouple wire and a thermocouple disposed between two layers of a multi-layer balloon FIGS. 26B–D variously show longitudinal perspective (FIGS. 26B–C) and partial axial cross-sectional (FIG. 2D) views of various aspects for one particular mode of a thermocouple/multi-layer balloon assembly such as the assembly shown in FIG. 26A.

FIGS. 26E–F show two different modes for a thermocouple/multi-layer balloon assembly, wherein FIG. 26E shows the thermocouple wire bound within a channel formed along the balloon in fluid isolation from the interior of the balloon, and FIG. 26F shows the thermocouple wire unbound and moveable within the channel when that channel is adapted by means of a port to communicate with the balloon inflation medium in order to equilibrate pressures between the channel and the balloon chamber.

FIG. 26G shows a partial longitudinal cross-sectional view of a thermocouple/balloon assembly according to FIG. 26F, showing the port positioned along the proximal taper region of the balloon.

FIGS. 28G–H show an exploded partially sectioned longitudinal view of another thermocouple/balloon assembly in a deflated condition (FIG. 28G) and an inflated condition (FIG. 28H).

FIGS. 29A and 29B show longitudinal side views of additional thermocouple/balloon assemblies similar to that shown in FIG. 28A, although FIG. 29B shows the elongated thermocouple members to include a stretchable zone adapted to allow for the thermocouple members to elongate such that the thermocouples maintain their relative position along the length of the ablation balloon member when the balloon inflates.

Figure 2A:
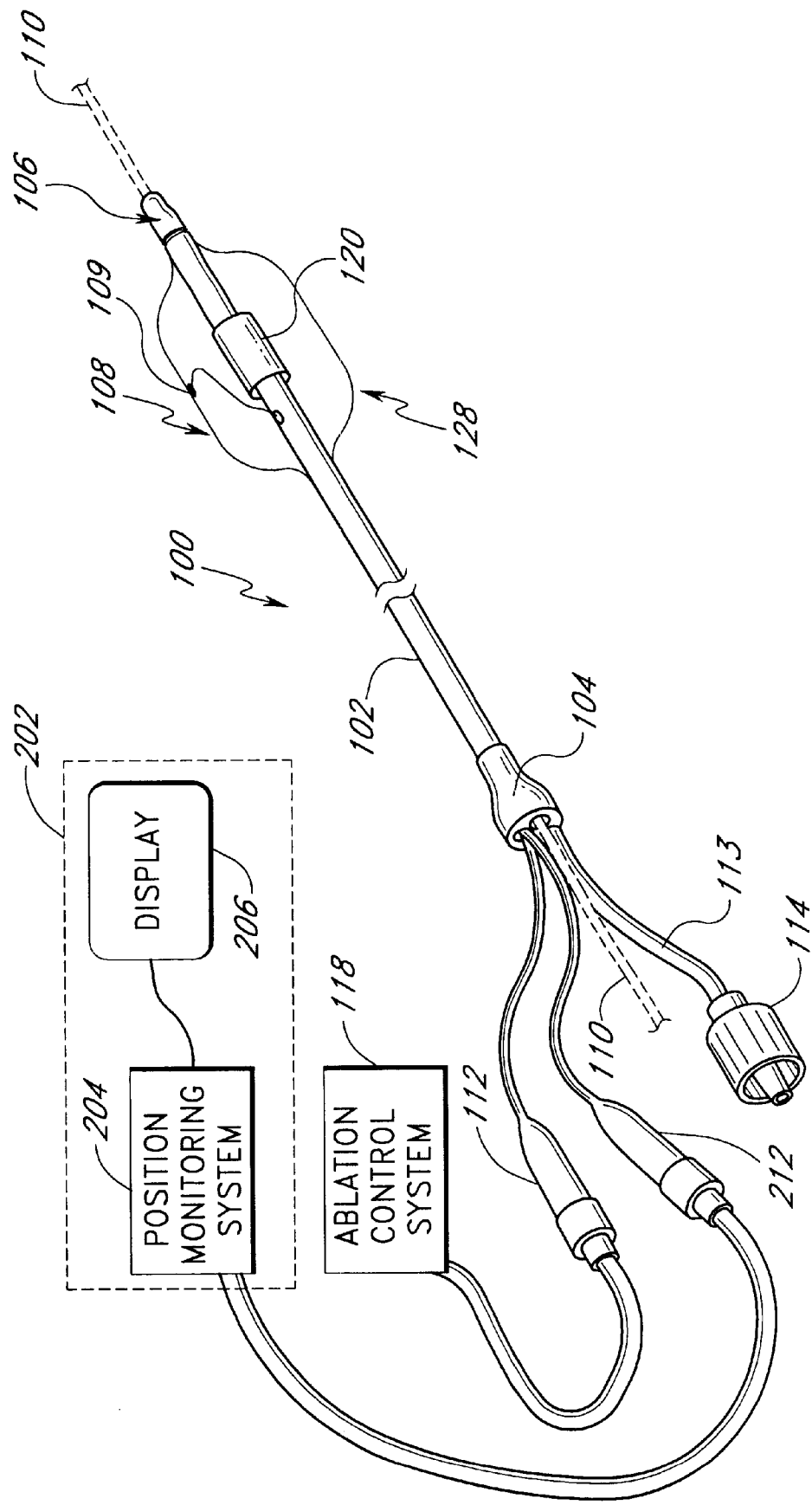
FIG. 2A shows an ablation catheter with position sensing capability operably connected to an ablation control system and a position sensing system. An expandable member of the catheter is illustrated in an expanded state.

In the drawings, the first digit of any three-digit number generally indicates the number of the figure in which the element first appears. Where four-digit reference numbers are used, the first two digits indicate the figure number.

DETAILED DESCRIPTION OF THE PREFERRED EMBODIMENT

Definitions of Terms

The following terms will have the following meanings throughout this specification.

The terms "body space," including derivatives thereof, is herein intended to mean any cavity or lumen within the body which is defined at least in part by a tissue wall. For example, the cardiac chambers, the uterus, the regions of the gastrointestinal tract, and the arterial or venous vessels are all considered illustrative examples of body spaces within the intended meaning.

The term "body lumen," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of lumens within the intended meaning. Blood vessels are also herein considered lumens, including regions of the vascular tree between their branch points. More particularly, the pulmonary veins are lumens within the intended meaning, including the region of the pulmonary veins between the branched portions of their ostia along a left ventricle wall, although the wall tissue defining the ostia typically presents uniquely tapered lumenal shapes.

The terms "circumference" or "circumferential", including derivatives thereof, as used herein include a continuous path or line which forms an outer border or perimeter that surrounds and thereby defines an enclosed region of space. Such a continuous path starts at one location along the outer border or perimeter, and translates along the outer border or perimeter until it is completed at the original starting location to enclose the defined region of space. The related term "circumscribe," including derivatives thereof, as used herein includes a surface to enclose, surround, or encompass a defined region of space. Therefore, a continuous line which is traced around a region of space and which starts and ends at substantially the same location "circumscribes" the region of space and has a "circumference" which includes the distance the line travels as it translates along the path circumscribing the space.

Still further, a circumferential path or element may include one or more of several shapes, and may be for example circular, oblong, ovular, elliptical, or otherwise planar enclosures. A circumferential path may also be three dimensional, such as for example two opposite-facing semi-circular paths in two different parallel or off-axis planes that are connected at their ends by line segments bridging between the planes.

For purpose of further illustration and example, FIGS. 1A–1D show circumferential paths 160, 162, 164, and 166, respectively. Each path 160, 162, 164, 166 translates along a portion of a pulmonary vein wall and circumscribes a defined region of space, shown at 161, 163, 165, and 167, respectively, each circumscribed region of space being a portion of a pulmonary vein lumen.

The term "transect", including derivatives thereof, as used herein includes a way to divide or separate a region of space into isolated regions. Thus, each of the regions circumscribed by the circumferential paths shown in FIGS. 1A–D transects the respective pulmonary vein, including its lumen and its wall, to the extent that the respective pulmonary vein is divided into a first longitudinal region located on one side of the transecting region, shown for example at region "X" in FIG. 1A, and a second longitudinal region on the other side of the transecting plane, shown for example at region "Y" also in FIG. 1A.

Therefore, a "circumferential conduction block" according to the present invention is formed along a region of tissue that follows a circumferential path along the pulmonary vein wall, circumscribing the pulmonary vein lumen and transecting the pulmonary vein relative to electrical conduction along its longitudinal axis. The transecting circumferential conduction block therefore isolates electrical conduction between opposite longitudinal portions of the pulmonary wall relative to the conduction block and along the longitudinal axis.

The terms "ablate" or "ablation," including derivatives thereof, are hereafter intended to include the substantial altering of the mechanical, electrical, chemical, or other structural nature of tissue. In the context of ablation applications shown and described with reference to the variations of the illustrative device below, "ablation" is intended to include sufficient altering of tissue properties to substantially block conduction of electrical signals from or through the ablated cardiac tissue.

The term "element" within the context of "ablation element" is herein intended to include a discrete element, such as an electrode, or a plurality of discrete elements, such as a plurality of spaced electrodes, which are positioned so as to collectively ablate a region of tissue.

Therefore, an "ablation element" according to the defined terms can include a variety of specific structures adapted to ablate a defined region of tissue. For example, one suitable ablation element for use in the present invention may be formed, according to the teachings of the embodiments below, from an "energy emitting" type of structure which is adapted to emit energy sufficient to ablate tissue when coupled to and energized by an energy source. Suitable "energy emitting" ablation elements for use in the present invention may therefore include, for example: an electrode element adapted to couple to a direct current ("DC") or alternating current ("AC") current source, such as a Radio Frequency ("RF") current source; an antenna element which is energized by a microwave energy source; a heating element, such as a metallic element or other thermal conductor which is energized to emit heat such as by convection or conductive heat transfer, by resistive heating due to current flow, or by optical heating with light; a light emitting element, such as a fiber optic element which transmits light sufficient to ablate tissue when coupled to a light source; or an ultrasonic element such as an ultrasonic crystal element which is adapted to emit ultrasonic sound waves sufficient to ablate tissue when coupled to a suitable excitation source.

In addition, other elements for altering the nature of tissue may be suitable as "ablation elements" under the present invention when adapted according to the detailed description of the invention below. For example, a cryogenic ablation (cryoblation) element adapted to sufficiently cool tissue to substantially alter the structure thereof may be suitable if adapted according to the teachings of the current invention. Furthermore, a fluid delivery element, such as a discrete port or a plurality of ports which are fluidly coupled to a fluid delivery source, may be adapted to infuse an ablating fluid, such as a fluid containing alcohol, into the tissue adjacent to the port or ports to substantially alter the nature of that issue.

Suitable "energy emitting" ablation elements for use in the present invention include, for example, but without limitation: an electrode element adapted to couple to a Direct Current (DC) or Alternating Current (AC) current source, such as a Radio Frequency (RF) current source; an antenna element which is energized by a microwave energy source; a heating element, such as a metallic element or other thermal conductor which is energized to emit heat such as by convection or conductive heat transfer, by resistive heating due to current flow, or an ultrasonic element such as an ultrasound crystal element which is adapted to emit ultrasonic sound waves sufficient to ablate tissue when coupled to a suitable excitation source.

Embodiments of the Invention

The following describes several ablation devices of a medical device system. Several of the disclosed devices employ sensors (e.g., thermocouples, electrodes, etc.) used with an expandable member of the medical article to sense a variety of parameters relating to the progression and efficacy of the ablation process, and illustrate a variety of ways in which such sensors can be used with the expandable member.

Several of the disclosed devices also include a position monitoring system that allows a clinician to precisely locate a distal end of the medical device within a body space by using feedback information provided by the system. Such feedback information is indicative of the position of the distal end of the medical device within the body space. The following devices of the position monitoring system are particularly well suited for applications involving positioning an ablation member at an area where a pulmonary vein extends from a left atrium and relative to a targeted circumferential region of tissue within the area, and therefore these devices are described in this context. Various aspects of the present invention, however, can be readily adapted by those skilled in the art for applications involving positioning medical articles within other body spaces.

Before describing the various devices of the position monitoring system and the variety of ways in which a sensor can be coupled to and/or used with an expandable member, a description of a preferred ablation catheter assembly is provided.

In the context of the illustrative application, catheter-based cardiac arrhythmia therapies generally involve introducing an ablation catheter into a cardiac chamber, such as in a percutaneous transluminal procedure, wherein an ablation element on the catheter's distal end portion is positioned at or adjacent to the aberrant conductive tissue. The ablation element is used to ablate the targeted tissue thereby creating a lesion.

FIG. 2A shows an exemplary ablation catheter assembly 100 operably connected through an electrical connector 112 to an ablation control system 118. The catheter assembly 100 includes an elongated delivery member 102 with a proximal end portion 104 and a distal end portion 106. The distal end portion 106 supports an ablation member 128 including an ablation element 120 and an expandable member 108. The expandable member can also include a sensor 109 that is explained below.

Figure 2B:
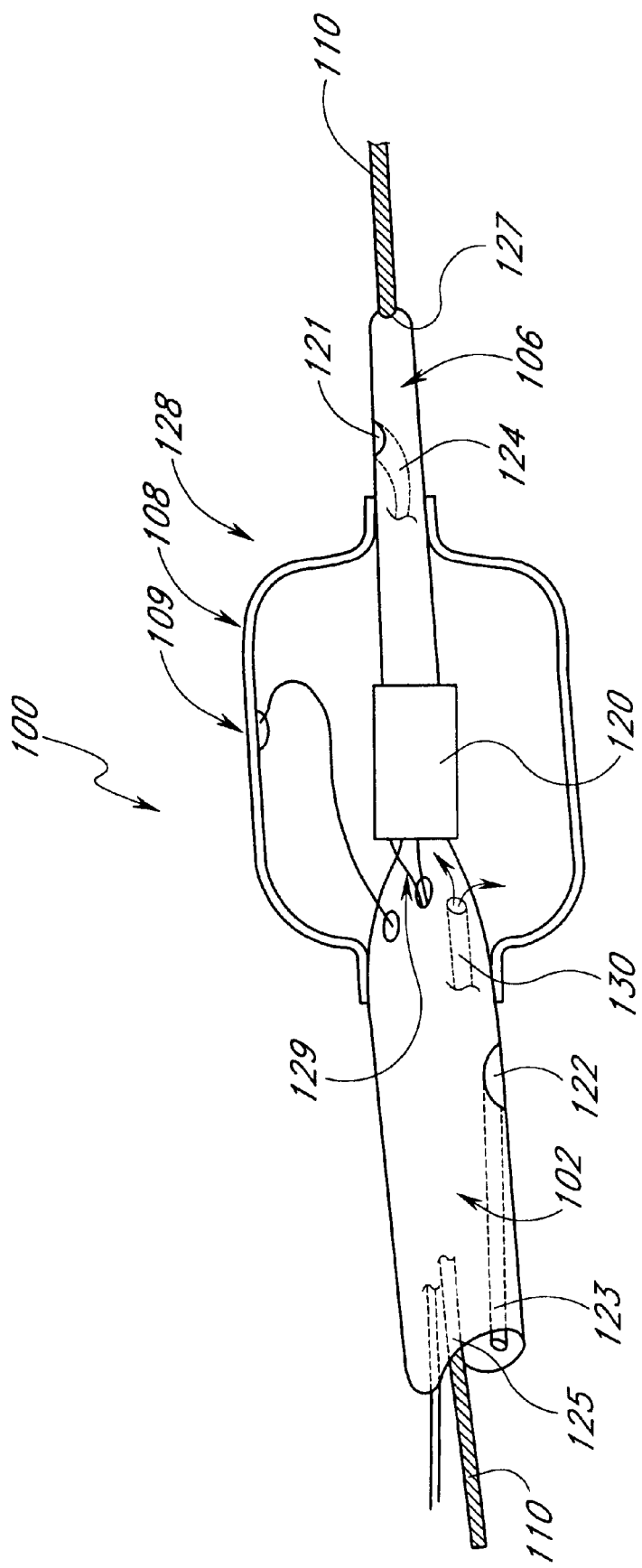
FIG. 2B shows details of an ablation member in the expanded state at a distal end of the ablation catheter of FIG. 2A, including a sensor.

The delivery member 102 desirably includes a plurality of lumens (some of which are illustrated in FIG. 2B). Various wires and electrical leads are routed to the distal end portion 106 through at least some of these lumens. In a preferred device, these lumens generally run the length of the delivery member 102; however, for some applications, the lumens can be shorter. In one example, a guidewire 110 runs through a lumen in the delivery member 102 from the proximal end portion 104 to the distal end portion 106. The proximal end portion 104 also connects through a tube 113 to a screw connector 114. By introducing fluid into the tube 113 through the screw connector 114, a physician can inflate the expandable member 108, as known in the art.

In some modes of the catheter assembly, as seen in FIG. 2B, the delivery member 102 includes a distal port 121, which is distal to an ablation member 128. In addition, there is a proximal port 122, which is provided proximal of the ablation member 128. The proximal port 122 connects to a proximal port lumen 123, and the distal port 121 connects to a distal port lumen 124. The distal port 121 allows the clinician to introduce fluids into the patient, take fluid samples from the patient, and take fluid pressure reading on the distal side of the ablation member 128. Similarly, the proximal port 122 allows the clinician to introduce fluids into the patient, take fluid samples from the patient, and take fluid pressure reading on the proximal side of the ablation member 128. These ports 121, 122 and lumens 123 and 124 are particularly useful when pressure or X-ray positioning techniques are employed, as explained below; however, the catheter assembly 100 need not include such ports and lumens when only an A-mode or Doppler position monitoring system is used with the catheter assembly.

In the illustrated device, the delivery member 102 also includes a guidewire lumen 125 that is sized to track over the guidewire 110. The lumen 125 terminates at a distal port 127 located on the distal end 106 of the delivery member 102.

When constructed for use in transeptal left atrial ablation procedures, the delivery member 102 desirably has an outer diameter provide within the range of from about 5 French to about 10 French, and more preferably from about 7 French to about 9 French. The guidewire lumen 125 preferably is adapted to slideably receive guidewires ranging from about 0.010 inch to about 0.038 inch in diameter, and preferably is adapted for use with guidewires ranging from about 0.018 inch to about 0.035 inch in diameter. Where a 0.035 inch guidewire is to be used, the guidewire lumen 125 preferably has an inner diameter of 0.040 inch to about 0.042 inch. In addition, where the delivery member 102 includes an inflation lumen 130 for use with an inflatable balloon (a preferred form of the expandable member 108), the inflation lumen 130 preferably has an inner diameter of about 0.020 inch in order to allow for rapid deflation times, although this may vary based upon the viscosity of inflation medium used, length of the lumen 130, and other dynamic factors relating to fluid flow and pressure.

In addition to providing the requisite lumens and support for the ablation member 128, the delivery member 102 for the illustrative application also is adapted to be introduced into the left atrium such that the distal end portion 106 can be placed within the pulmonary vein ostium in a percutaneous translumenal procedure, and even more preferably in a transeptal procedure as otherwise herein provided. Therefore, the distal end portion 106 is preferably flexible and adapted to track over and along a guidewire seated within the targeted pulmonary vein.

In a further construction, the proximal end portion 104 is adapted to be at least 30% more stiff than the distal end portion 106. According to this relationship, the proximal end portion 104 may be suitably adapted to provide push transmission to the distal end portion 106 while the distal end portion 106 is suitably adapted to track through bending anatomy during in vivo delivery of the distal end portion 106 of the device into the desired ablation region.

Notwithstanding the specific device constructions just described, other delivery mechanisms for delivering the ablation member 128 to the desired ablation region are also contemplated. For example, while the FIG. 2A variation is shown as an "over-the-wire" catheter construction, other guidewire tracking designs are suitable substitutes, such as, for example, catheter devices which are known as "rapid exchange" or "monorail" variations, wherein the guidewire is only housed coaxially within a lumen of the catheter in the distal region of the catheter in another example, a deflectable tip design may also be a suitable substitute to independently select a desired pulmonary vein and direct the transducer assembly into the desired location for ablation. Further to this latter variation, the guidewire lumen and guidewire of the variation depicted in FIG. 2A may be replaced with a "pullwire" lumen and associated fixed pullwire which is adapted to deflect the catheter tip by applying tension along varied stiffness transitions along the catheter's length. Still further to this pullwire variation, acceptable pullwires may have a diameter within the range from about 0.008 inch to about 0.020 inch, and may further include a taper, such as, for example, a tapered outer diameter from about 0.020 inch to about 0.008 inch.

As discussed above, the distal end portion 106 of the delivery member supports an ablation member 128. The ablation member 128 includes an expandable member 108 and an ablation element 120. The expandable member 108 cooperates with the ablation element 120 to position and anchor the ablation element 120 relative to a circumferential region of tissue at a location where a pulmonary vein extends from the left atrium, which is targeted for ablation.

In the illustrated device, the expandable member 108 is an inflatable balloon. The balloon has a diameter in a collapsed state roughly the same as the outer diameter of the delivery member distal end portion 106. The balloon 108 can be expanded to a diameter generally matching the diameter of the circumferential region of tissue, and may be expandable to a plurality of expanded positions in order to work with pulmonary vein ostia and/or pulmonary veins of various sizes. It is understood, however, that the ablation catheter assembly can also include other types of expandable members, such as, for example baskets, cages and like expandable structures.

The expandable balloon 108 may be constructed from a variety of known materials, although the balloon preferably is adapted to conform to the contour of a pulmonary vein ostium and/or pulmonary vein lumenal wall. For this purpose, the balloon material can be of the highly compliant variety, such that the material elongates upon application of pressure and takes on the shape of the body lumen or space when fully inflated. Suitable balloon materials include elastomers, such as, for example, but without limitation, silicone, latex, or low durometer polyurethane (for example a durometer of about 80 A).

In addition, or in the alternative to constructing the balloon of highly compliant material, the balloon can be formed to have a predefined fully inflated shape (i.e., be preshaped) to generally match the anatomic shape of the body lumen in which the balloon is inflated. For instance, as described below in greater detail, the balloon can have a distally tapering shape to generally match the shape of a pulmonary vein ostium, and/or can include a bulbous proximal end to generally match a transition region of the atrium posterior wall adjacent to the pulmonary vein ostium. In this manner, the desired seating within the irregular geometry of a pulmonary vein or vein ostium can be achieved with both compliant and non-compliant balloon variations.

Notwithstanding the alternatives which may be acceptable as just described, the balloon is preferably constructed to exhibit at least 300% expansion at 3 atmospheres of pressure, and more preferably to exhibit at least 400% expansion at that pressure. The term "expansion" is herein intended to mean the balloon outer diameter after pressurization divided by the balloon inner diameter before pressurization, wherein the balloon inner diameter before pressurization is taken after the balloon is substantially filled with fluid in a taut configuration. In other words, "expansion" is herein intended to relate to the change in diameter that is attributable to the material compliance in a stress/strain relationship. In one more detailed construction, which is believed to be suitable for use in most conduction block procedures in the region of the pulmonary veins, the balloon is adapted to expand under a normal range of pressure such that its outer diameter may be adjusted from a radially collapsed position of about 5 millimeters to a radially expanded position of about 2.5 centimeters (or approximately 500% expansion).

The ablation element 120 cooperates with the expandable member 108 such that the ablation element 120 is held in a generally fixed position relative to the target circumferential region of tissue. The ablation element can be located outside or inside the expandable member, or can be located at least partially outside the expandable member. The ablation element, in some forms, also includes a portion of the expandable member. For instance, the ablation catheter assembly in FIGS. 2A–B includes an ultrasonic transducer located within the expandable member 108. In one device, the ultrasonic transducer excites a portion of the expandable member 108 during ablation. The specific construction of the ultrasonic transducer and the associated construction of the delivery member shaft that supports the transducer, is described below in connection with FIGS. 10A–O.

Figure 16B:
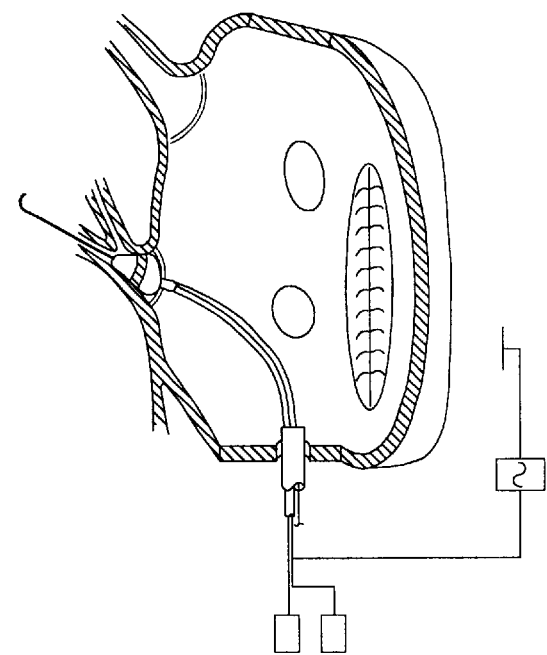
FIG. 16B shows a sequential mode of use for the ablation catheter shown in FIG. 16A, although shows the circumferential ablation member after being advanced over a guidewire and positioned at one desired location at a location where the pulmonary vein extends from the left atrium with the balloon expanded and engaged to the surrounding wall during ablation to form a circumferential conduction block.
Figure 16C:
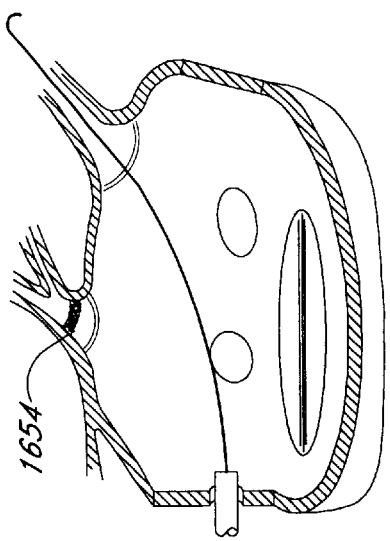
FIG. 16C shows a segmented view of a left atrium and pulmonary veins with one type of circumferential lesion formed after ablation with a circumferential ablation member according to the modes of FIGS. 16A–B.
Figure 16A:
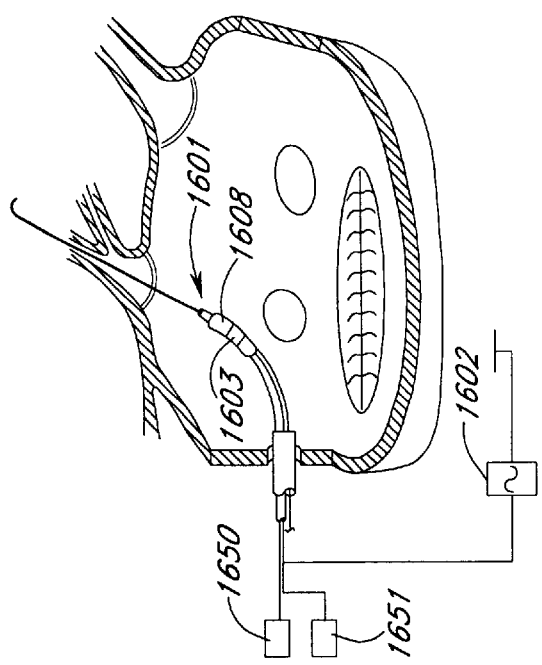
FIG. 16A shows a segmented view of a left atrium and pulmonary veins extending from the atrium, and shows a perspective view of one type of ablation catheter with a circumferential ablation member having a balloon in an unexpanded condition positioned within the left atrium.

As noted above, the ablation element can also take many other forms. For instance, the ablation element can include one or more electrodes exposed on the exterior of the expandable member and adapted to contact the targeted tissue. FIGS. 16A, D, H and 17A illustrate devices of this type of ablation element, which are described below. The electrode(s) can also be positioned within the expandable member with an electrical path established between the electrode and the tissue by an electrolytic solution (e.g., saline), as discussed in more detail in connection with FIG. 17B below. In either of these modes, as illustrated in FIG. 2A, the ablation element 120 is typically connected to the electrical connector 112 and to a ground patch (not shown). A circuit thereby is created which includes the ablation element 120, the patient's body, and the ground patch that provides either earth ground or floating ground to the ablation control 118. In the circuit, an electrical current, such as a Radio Frequency (RF) signal may be sent through the patient between the ablation element 120 and the ground patch.

FIG. 2B shows details of the distal end portion 106 of the catheter assembly 100 and, in particular, shows the ablation element 120 located circumferentially about an axial centerline of the delivery member 102. A pair of wires 129 connect the ablation element 120 to a connector 112 at the proximal end of the catheter (shown in FIG. 2A) The connector 112 is coupled to a corresponding cable of the ablation control system 118. If the ablation element 120 includes more than one electrode, the conductor lead can connect to all of the electrodes or energy sources, or separate conductors can be used so as to allow for independent control of each electrode or energy source under some modes of operation.

The tissue ablation catheter 100 assembly also desirably includes feedback control. For instance, the expandable member 108 can include one or more thermal sensors 109 (e.g., thermocouples, thermistors, etc.) that are provided to either the outer side or the inside of the expandable member 108. Monitoring temperature at this location provides indicia for the progression of the lesion. If the temperature sensors are located inside the expandable member 108, the feedback control may also need to account for any temperature gradient that occurs through wall of the expandable member 108.

If the sensors 109 are placed on the exterior of the expandable member 108, they may also be used to record electrogram signals by reconnecting the signal leads to different input port of a signal-processing unit. Such signals can be useful in mapping the target tissue both before and after ablation.

The thermocouples and/or electrodes desirably are blended into the expandable member 108 in order to present a smooth profile. Transition regions, which are formed by either adhesive or melted polymer tubing, "smooth out" the surface of the expandable member 108 as the surface steps up from the outer surface of the expandable member 108 to the thermocouple surface. Various constructions to integrate the thermocouples and/or electrodes into the expandable member, as well as various approaches to using thermocouples and electrodes with an expandable member, are described in detail below.

The illustrated ablation catheter assembly 100 is designed for treatment of the more common forms of atrial fibrillation, resulting from perpetually wandering reentrant wavelets. Such arrhythmias are generally not amenable to localized ablation techniques, because the excitation waves may circumnavigate a focal lesion. Thus, the catheter assembly 100 uses the ablation element 120 to form a substantially circumferential lesion, or lesions, to segment the atrial tissue so as to block conduction of the reentrant wave fronts.

During a surgical procedure, a clinician guides the ablation catheter assembly 100 into the left atrium. The clinician then manipulates the catheter so that the ablation member enters the pulmonary vein from the left atrium. The goal of the surgical procedure is to position the ablation member just inside the pulmonary vein, at the pulmonary vein ostium. Once the expandable member 108 is positioned at desired site within the ostium and relative to the targeted region of circumferential tissue, the ablation element 120 is activated to ablate the targeted tissue and thereby form the desired lesion.

Access to the atrium is gained using techniques known in the art. After access to the atrium is obtained, another guidewire or guide member is advanced into the pulmonary vein. This is typically done through a guiding introducer which is coaxial within a transeptal sheath seated in the fossa ovalis, or by using a deflectable guidewire or catheter such as those disclosed in U.S. Pat. No. 5,575,766 to Swartz. Alternatively, the guidewire should have sufficient stiffness and maneuverability in the left atrial cavity to unitarily select the desired pulmonary vein distally of the transeptal sheath seated at the fossa ovalis. The guidewire is advanced into the pulmonary vein ostium to a suitable anchoring position.

The ablation catheter 100 is then slid over the proximal end of the guidewire 110 and advanced until the ablation member of the ablation catheter 100, including the ablation element 120, is positioned at the area where the pulmonary vein extends from the left atrium. A combination of pushing and pulling alternatively on the guidewire 110 and the ablation catheter 100 may be employed to facilitate advancement and positioning of the ablation catheter 100.

Delivery of energy. (e.g., thermal, RF, ultrasonic, electrical, etc.) to the tissue of the pulmonary vein ostium is commenced once the ablation element 120 is positioned at the desired ablation region. Good coupling of the energy produced by the ablation element 120 with the tissue facilitates creation of a continuous lesion. Energy from the ablation control system 118 (FIG. 2A) is typically delivered to the ablation element 120 via electrical conductor leads. The ablation control system 118 includes a current source for supplying current to the ablation element 120, a monitoring circuit, and a control circuit. The current source is coupled to the ablation element 120 via a lead set (and to a ground patch in some modes). The monitor circuit desirably communicates with one or more sensors (e.g., temperature and/or current sensors) which monitor the operation of the ablation element 120. The control circuit is connected to the monitoring circuit and to the current source in order to adjust the output level of the current driving the ablation element 120 based upon the sensed condition (e.g., upon the relationship between the monitored temperature and a predetermined temperature set point).

Position Monitoring System

FIG. 2A shows an ablation catheter with position monitoring capability operably connected to an ablation control system 118 and a position monitoring system 202. The position monitoring system 202 includes a sensor control system 204 and a display 206. The sensor control system 204 communicates with one or more sensor elements 220 located in, or near the expandable member 108. In one variation, the ablation element 120 and sensor element 220 are combined in a single element that provides both sensing and ablation capabilities. In other variations, separate elements are used for the ablation element 120 and the sensor element(s) 220. Various exemplifying device embodiments of the position sensor 220 are described in connection with FIGS. 3–14.

Amplitude Monitoring

Figure 3:
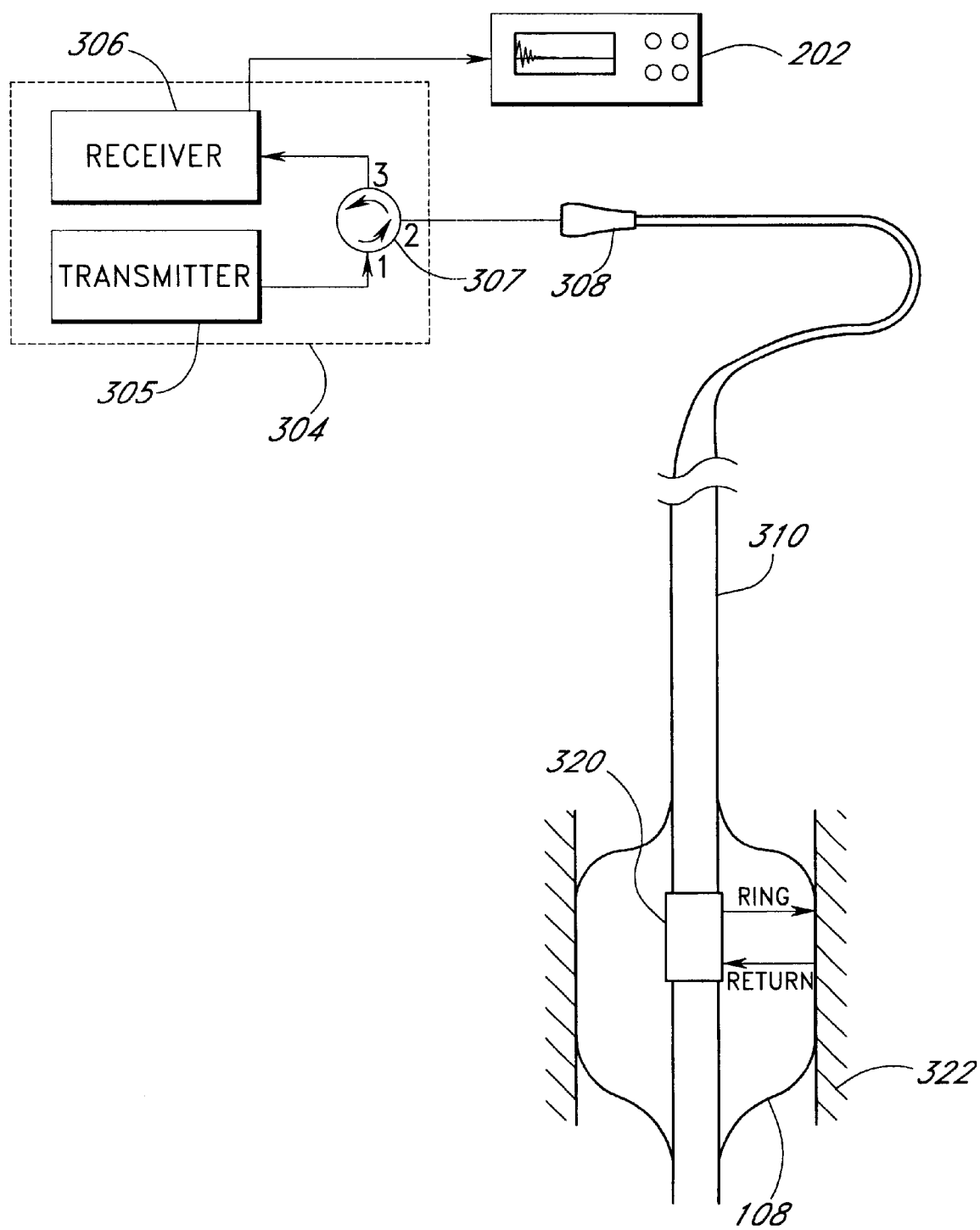
FIG. 3 shows an ultrasonic position sensing system that uses an ablation element as an ultrasonic position sensor.

FIG. 3 illustrates the basic operation of an ultrasonic position monitoring system. In FIG. 3, the sensor 320 is embodied as a single, circumferentially symmetric ultrasonic transducer 320. The sensor 320 can be the ultrasonic ablation element, as illustrated in FIGS. 2A and 3, or a separate ultrasonic transducer in addition to an ultrasonic ablation element, as illustrated in FIGS. 5A–E, which are described below. The transducer 320 is shown positioned in a pulmonary vein 322, and the transducer 320 is operably connected to a sensor control system 304. In an exemplary device, the sensor control system is a Panametrics Model 5073PR. The sensor control system 304 includes a transmitter 305, a receiver 306, and a diplexer 307. An output from the transmitter 305 is provided to a transmitter port (port 1) of the diplexer 307. An output from a receiver port (port 3) of the, diplexer 307 is provided to an input of the receiver 306. A transducer port (port 2) of the diplexer 307 is provided through a connector 308 to the transducer 320. An output from the receiver 306 is provided to the display 202.

A diplexer, such as the diplexer 307, is commonly used in radar and sonar systems to isolate the transmitter output from the receiver input. Energy provided to the transmitter port of the diplexer (port 1) is provided to the transducer port (port 2) of the diplexer 307, but not to the receiver port of the diplexer (port 3). Energy provided from the transducer 320 to the transducer port of the diplexer (port 2) is provided to the receiver port (port 3) of the diplexer 307, but not to the transmitter port (port 3) of the diplexer.

The diplexer 307 can be a circulator or an electronically controlled switch controlled by a timing generator. The timing generator sets the switch to connect the transmitter 305 to the transducer 320 for a first time period. The timing generator then sets the switch to connect the receiver to the transducer 320 for a second time period. By switching the transducer 320 between the transmitter 305 and the receiver 306, the diplexer 307 effectively "timeshares" the transducer 320 between the transmitter 305 and the receiver 306.

The transmitter 305 generates a signal that drives the transducer 320. When the diplexer 307 connects the transmitter 305 to the transducer 320, the drive signal from the transmitter 305 causes the transducer 320 to emit an ultrasonic sound wave. The ultrasonic sound wave propagates through the interior of the expandable member 108, through the wall of the expandable member 108, and reflects off of the inner wall of the ostium 322. The reflected ultrasonic energy returns to the transducer 320 and causes the transducer 320 to generate an echo signal. The echo signal is provided through the diplexer 307 to the receiver 306. The receiver 306 amplifies and processes the echo signal to produce a display signal. The display signal is provided to the display 202.

Figure 4A:
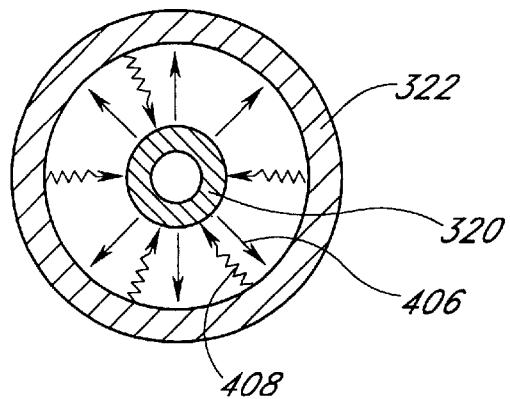
FIG. 4A shows the cylindrical ultrasonic wavefronts produced by a uniformly circumferential (cylindrical) ultrasonic transducer.

FIG. 4A is an axial cross section showing the transducer 320 centered in the ostium 322. The transducer transmits a radiated wave 406. For a cylindrically symmetric transducer 320, the radiated wave 406 will approximate a cylindrical wave that expands away from the transducer 320. When the cylindrical wave reaches the ostium 322, the wave will be reflected in a substantially cylindrically symmetric fashion to produce a reflected wave 408 that is similar to a cylindrical wave as well. The reflected wave 408 propagates back to the transducer 320.

Reflections will occur when the ultrasonic sound wave propagating in a medium strikes a transition (or interface) in the acoustic properties of the medium. Any interface between materials having different acoustic properties will cause a portion of the wave to be reflected.

Figure 4B:
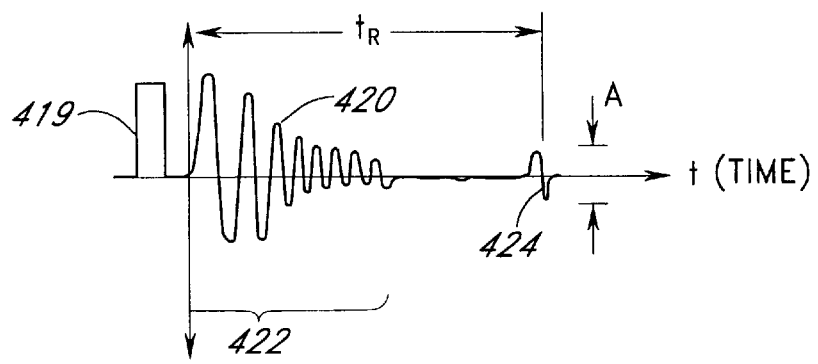
FIG. 4B shows a downrange time-domain response produced by an ultrasonic sensing system having an ultrasonic transducer configured as a transceiver using a short-pulse transmitter.

FIG. 4B shows a downrange, time-domain, amplitude mode (A-mode) plot of the response produced on the display 202 by the system shown in FIG. 3. The x-axis of the plot shown in FIG. 4B is a time axis where t=0 corresponds to the time when the diplexer 307 connects the transducer 320 to the receiver 306. During a time period just before t=0, the transducer 320 is connected to the transmitter 305, and the transmitter produces a transmit pulse 419. The y-axis in FIG. 4B is an amplitude plot of the energy produced by ultrasonic vibrations of the transducer 320. The plot in FIG. 4B shows a ring-down signal 420 during a ring-down period 422 (a time period $0<t<t_r$). The plot also shows an echo pulse 424 at a time $t_r$.

The transmit pulse 419 causes the transducer 320 to vibrate (in a manner very similar to a bell) during the ring-down period 422 thereby producing the ring-down signal 420. The echo pulse 424 is caused by ultrasonic energy that is reflected from the ostium 322 back to the transducer 320. During the ring-down period 422 it is difficult to see signals caused by reflections (such as the signal 424) because the signals produced by reflections are typically relatively small in amplitude and are easily masked by the relatively large amplitude portions of the ring-down signal 420. Thus, it is difficult to detect reflections from targets that are so close to the transducer 320 that their reflections return during the ring-down period 422. This can limit the minimum useful range of the transducer 320.

Figure 4C:
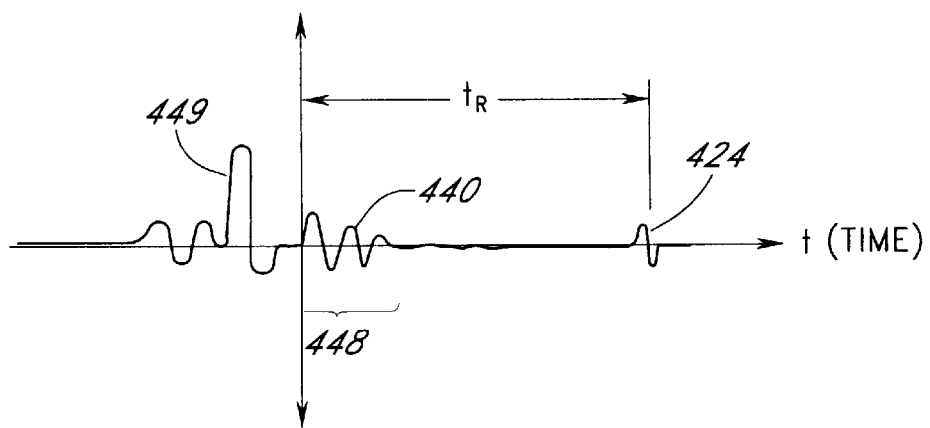
FIG. 4C shows a downrange time-domain response produced by an ultrasonic sensing system having an ultrasonic transducer configured as a transceiver using a modified-pulse transmitter.

As shown in FIG. 4C, the ring-down time of the transducer 320 can be reduced by configuring the transmitter 305 to provide a shaped transmit pulse 449. The shaped transmit pulse drives the transducer 320 in a manner that reduces the amplitude of the ringing and shortens the ring-down period. Thus, FIG. 4C shows a ring-down time 448 that is less than the ring-down time 422 shown in FIG. 4B. FIG. 4C also shows a ring-down signal 440 having an amplitude that is relatively smaller than the amplitude of the ring-down signal 420 in FIG. 4B. Since the ring-down period 448 is shorter, the shaped transmit pulse 449 allows the transducer 320 to be used to detect targets at a shorter distance.

In an device where the transducer 320 is also used as the ablation element 120, the transmitter 305 provides two power modes, a low-power mode used for position measurements, and a high-power mode used for ablation. When ablation is desired, the diplexer 307 stops switching between the receiver 306 and the transmitter 305, and stays locked on the transmitter 305 while the transmitter operates in the high-power mode.

Ultrasonic ablation requires that the transducer 320 produce an ultrasonic wave having relatively higher power. Higher power typically requires a transducer 320 having a relatively large physical size. Larger transducers often have longer ring-down times. While the use of a shaped transmit pulse will reduce ring-down times, for some transducers even the use of a shaped transmit pulse does not shorten the ring-down time sufficiently to allow the ablation element 120 to be used for position sensing. Moreover, in some devices, the ablation element 120 is not an ultrasonic transducer, and thus may be unsuitable for use as a position sensor. Thus, in some devices, it is desirable to add one or more ultrasonic transducers to be used for position sensing.

Figure 5A:
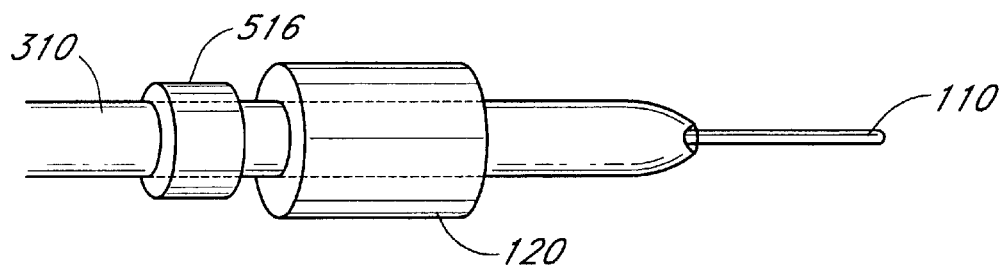
FIG. 5A shows an ultrasonic position sensing system that uses an ultrasonic sensing element proximal to the ablation element.

FIG. 5A shows a distal end of a catheter-based ultrasonic position monitoring system that uses an ultrasonic sensing element 516 proximal to the ablation element 120. (In FIGS. 5A–C the expandable member 108 is omitted for clarity). The sensing element 516 is used for position sensing, not ablation, and thus does not need to handle the higher powers needed for an ablation element. This allows the characteristics of the sensing element 516 to be tailored to attributes needed for position sensing, such attributes typically include, small size, low power, short ring-down times, etc. When used in connection with the sensor control system 304 shown in FIG. 3, the sensing element 516, rather than the ablation transducer 120, is connected to the diplexer 307. In other respects, the sensing element operates in a manner similar that discussed above in connection with FIGS. 4A–C.

Figure 5B:
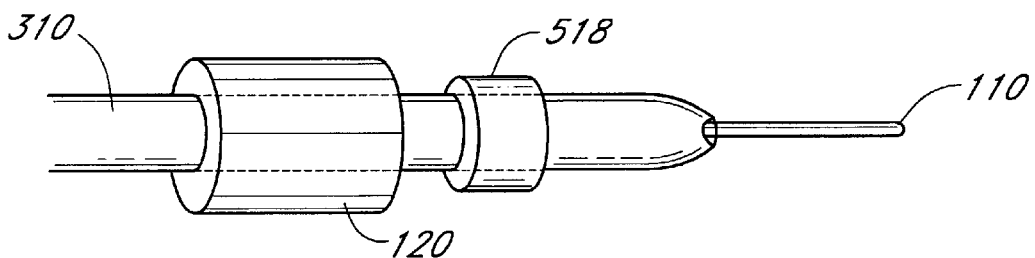
FIG. 5B shows an ultrasonic position sensing system that uses an ultrasonic sensing element distal to the ablation element.

FIG. 5B shows an ultrasonic position sensing system that uses an ultrasonic sensing element 518 distal to the ablation element 120. In other respects, the system shown in FIG. 5B is similar to the system shown in FIG. 5A.

Figure 5C:
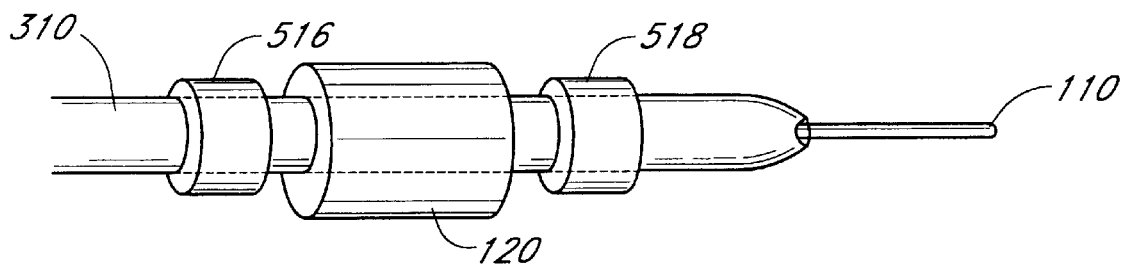
FIG. 5C shows an ultrasonic position sensing system that uses two ultrasonic sensing elements, one ultrasonic element is proximal to the ablation element and one ultrasonic element is distal to the ablation element.

FIG. 5C shows an ultrasonic position sensing system that uses both the proximal sensor 516 and the distal sensor 518. The two sensors 516 and 516 are each driven by the sensor control system 304 either in parallel (using separate channels in the system 304) or in serial (first one than the other).

Figure 5D:
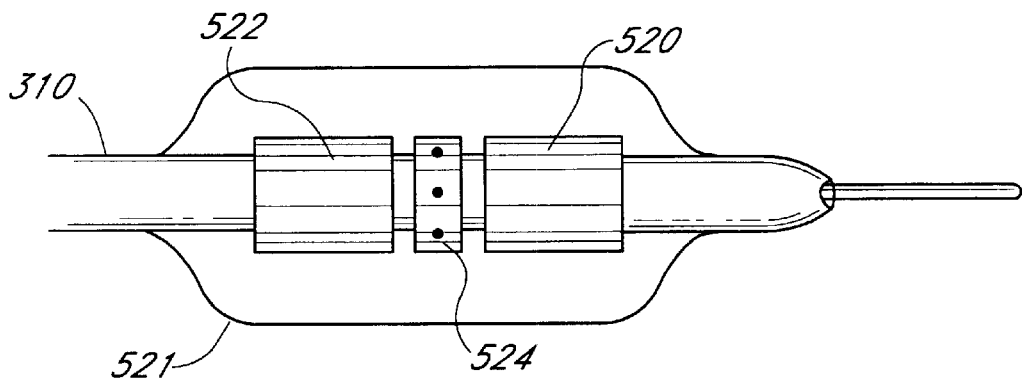
FIG. 5D shows an ultrasonic position sensing system between two ablation elements enclosed by a single balloon.
Figure 5E:
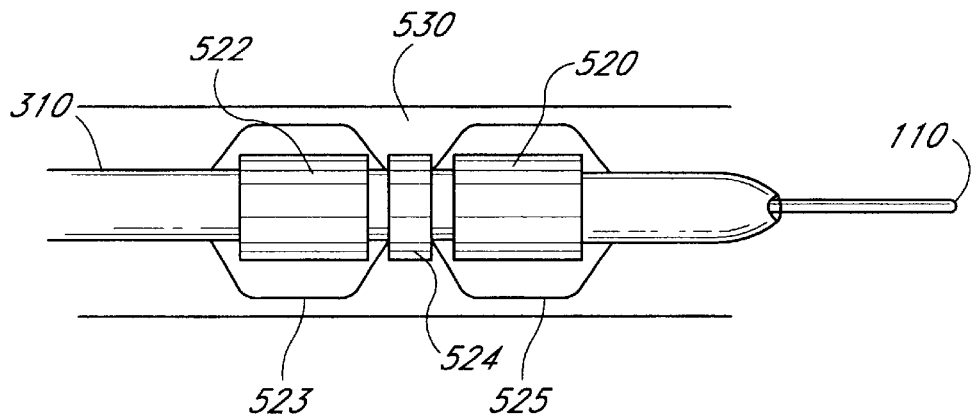
FIG. 5E shows an ultrasonic position sensing system between two ablation elements where each ablation element is enclosed by a separate balloon.

FIGS. 5D–E shows yet other devices of an ultrasonic sensor system wherein a single position sensing transducer 524 is provided between a proximal ablation element 522 and a distal ablation element 520. In FIG. 5D, both ablation elements 520 and 522 are enclosed by a single expandable member (e.g., a balloon) 512. In FIG. 5E an expandable member 523 surrounds the ablation element 522 and an expandable member 525 surrounds the ablation element 520. In FIG. 5E, the ablation elements 522 and 520 are optional, and ablation energy may be provided by, for example, an ablation solution introduced in the space 530 between the expandable members 523 and 525. Ablation solutions include solutions that cause ablation, such as, for example, solutions that cause cooling, solutions that cause heating, or solutions that cause chemical reactions on the tissue wall in the region 530.

Figure 5F:
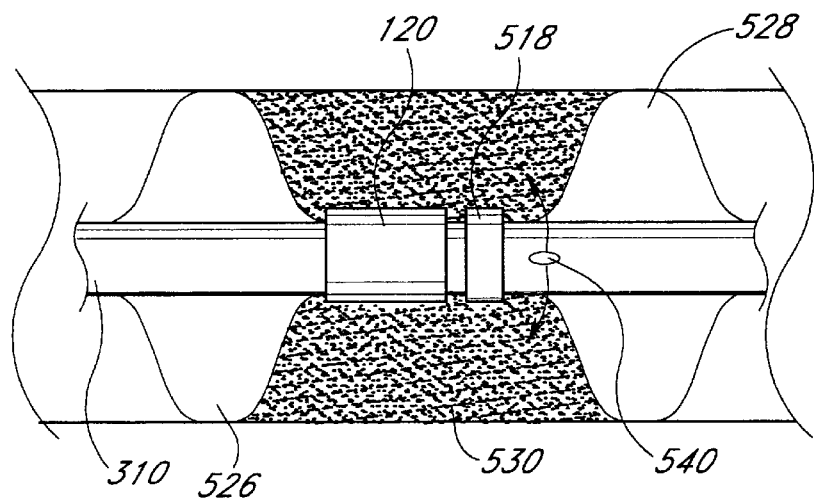
FIG. 5F shows an ultrasonic positioning sensing system located next to an ablation element and between a pair of inflatable balloons.

FIG. 5F illustrates another device of an ultrasonic sensor system. A single positioning sensing transducer 518 is positioned next to an ablation element 120. In the illustrated device, the transducer is located on the distal side of the ablation element 120; however, it can be located on the proximal side as well. Both the sensing transducer and the ablation element are located between a pair of expandable members 526,528. In one variation, the expandable members are a pair of inflatable balloons that may have differing diameters such that the distal-most balloon seals off blood flow, while the proximal balloon permits some flow of fluid from the space 530 between the balloons. In the illustrated variation, the ablation member comprises at least one electrode 120 and a fluid port 540 communicates with the space 530 between the balloons 526,528. An electrolytic solution (e.g., saline) is introduced into the space between the balloons.

This solution electrically couples the electrode to the circumferential region of tissue located between the inflated pair of balloons. The sensing transducer 518 aids in the proper positioning of this assembly within the pulmonary vein ostium, in the manner described above.

Figure 5G:
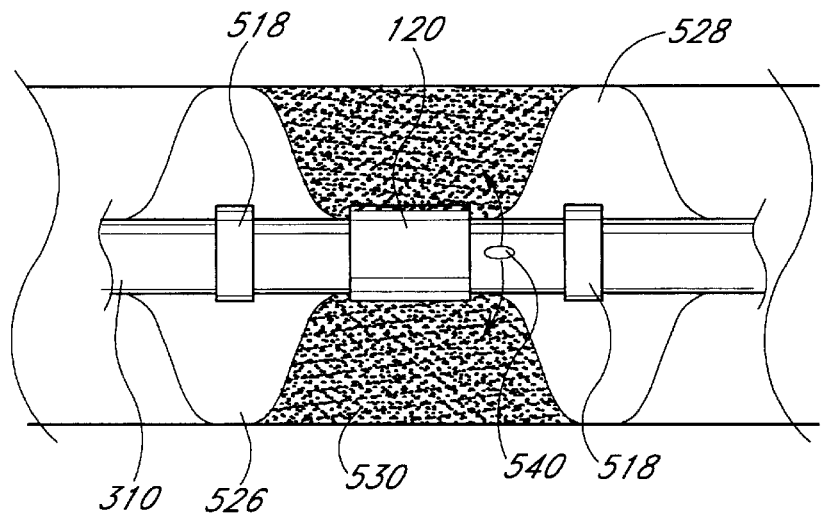
FIG. 5G shows a pair of ultrasonic elements of a positioning sensor system located next to an ablation element that is disposed between a pair of inflatable balloons.

In another variation, as seen in FIG. 5G, the ultrasonic sensor system includes a pair of positioning sensing transducers 518. Each transducer 518 is positioned in one of the expandable members 526,528 (e.g., inflatable balloons) with the ablation element 120 disposed between the expandable members 526,528.

The sensor systems shown in FIG. 3, and FIGS. 5A–F are all used in a similar fashion to measure the position of the ablation element relative to the ostium. FIGS. 6A–C illustrate the use of the A-mode ultrasonic systems to determine position.

FIG. 6A shows an A-mode response of the ultrasonic sensor systems when an ultrasonic transducer, such as the ultrasonic transducer 320, is in the atrium and not in the vein. The A-mode response in FIG. 6A shows a ring-down signal 602 and little else except a few indefinite echo returns 604. The response show no definite echo signals because the walls of the atrium are too far away from the transducer and/or are poorly oriented to provide a strong echo response back to the transducer.

FIG. 6B shows an A-mode response of the ultrasonic sensor systems when an ultrasonic transducer, such as the ultrasonic transducer 320, is partially in the pulmonary vein (e.g., half way into the vein). The A-mode response in FIG. 6B shows the ring-down signal 602 and relatively weak echo return 606. Moreover, the echo return 606 is relatively spread-out in time. The signal is weak because only a portion of the transducer 302 is in the vein and only the portion of the transducer 302 in the vein receives a strong echo. The portion of the transducer 302 outside the vein (in the atrium) does not see a strong echo response. The echo return 606 is relatively spread-out in time because the diameter of the vein varies significantly near the opening into the atrial chamber.

FIG. 6C shows an A-mode response of the ultrasonic sensor systems when an ultrasonic transducer, such as the ultrasonic transducer 320, is fully inserted in the pulmonary vein. The A-mode response in FIG. 6C shows the ring-down signal 602 and relatively strong, short, echo return 608. The signal is relatively stronger than the signal 606 because all of the transducer 302 is inside the vein and thus all of the transducer 302 is receiving a return echo. The signal 608 also is relatively short because all portions of the echo return at almost the same time (assuming the transducer 320 is near the center of the vein).

To position the transducer 320 (and thus the ablation element 120), the clinician (e.g., an interventional electrophysiologist) inserts the ablation catheter while watching the display 202 for the progression of echo signals 604, 606 and 608. The clinician stops advancing the delivery member once when he or she sees a signal profile similar to the signal 608 depicted in FIG. 6C.

FIG. 6D shows a two-trace display produced by the two-transducer system shown in FIG. 5C having a proximal sensor 516 and a distal sensor 518. The two-transducer system can provide more precise positioning f the ablation element 120 because, as shown in FIG. 6D, the proximal sensor 516 produces a first A-mode signal having a ring-down pulse 602 and an echo pulse 612; and the distal sensor 518 produces a second A-mode signal having a ring-down pulse 602 and an echo pulse 610.

When inserting a two-transducer system into the ostium, the clinician will first observe the echo pulse 610 rise up and move towards the ring-down pulse 602 (as the distal sensor moves into the vein). The clinician will then see the echo pulse 612 rise up and move towards the ring-down pulse 602 as the clinician advances the proximal transducer 516 into the pulmonary vein ostium.

As with the single sensor system, the distance between the ring-down pulse and the echo pulse is a measure of the distance to the target (e.g., the pulmonary wall, vein wall, etc.) that produced the echo pulse. The unquantified signal profile can be used by the clinician to position the ablation member 120 relative to a pulmonary vein ostium of a pulmonary vein in order to ablate a circumferential region of tissue at a location where the pulmonary vein extends from the left atrium; however, this signal can also be quantified to provide information regarding the anatomical size and shape of the particular patient's vein ostium. The clinician can use such information to determine whether the size of the expandable member is sufficient to engage the wall of the vein and/or vein, ostium.

Figure 7A:
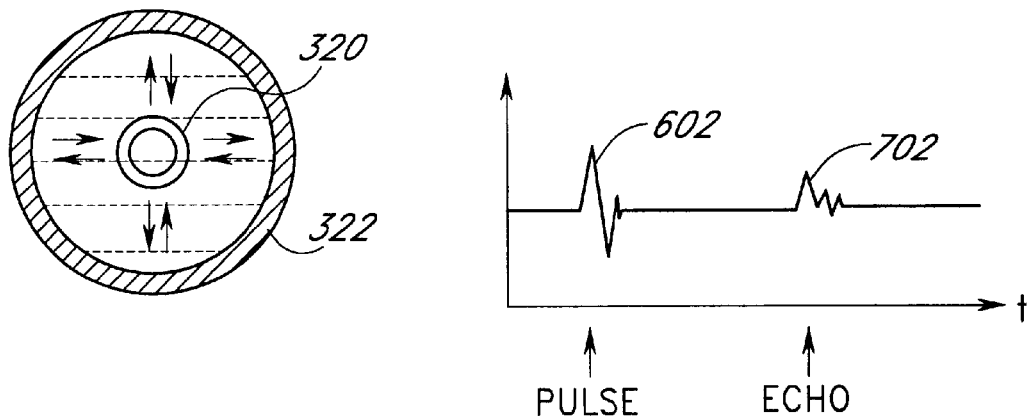
FIG. 7A shows an ultrasonic sensing system centered in a cavity or ostium and a corresponding downrange time-domain response.
Figure 7B:
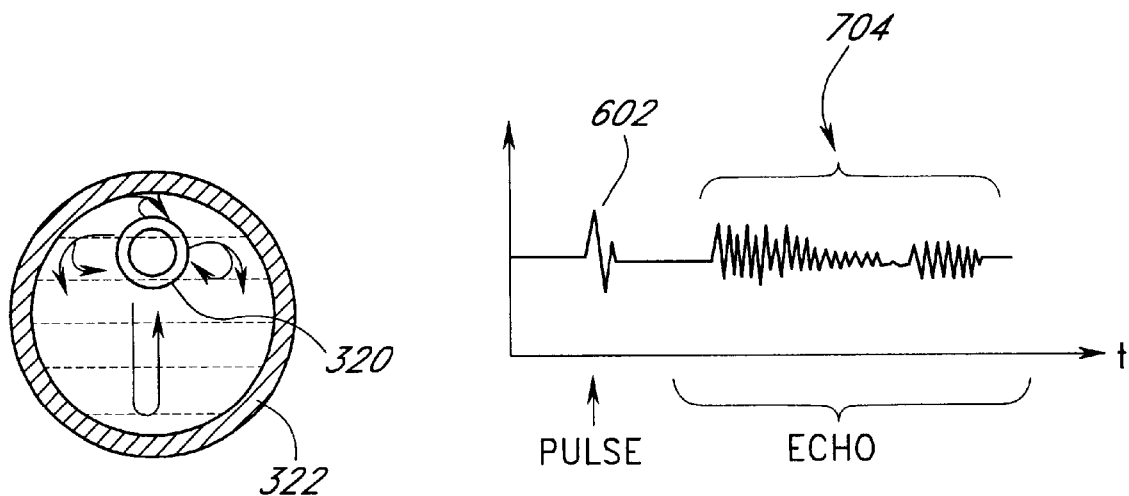
FIG. 7B shows an ultrasonic sensing system positioned off-centered in a cavity or ostium and a corresponding a downrange time-domain response.

The shape (width and height) of the echo pulses 608, 610 and 612 can also be used to center the transducer 320 within the vein ostium. The echo pulses 608, 610 and 612 will be affected by the location of the ultrasonic transducer with respect to the axial centerline of the vein. As shown in FIG. 7A, when a cylindrical transducer, such as the transducer 320, is located near the center of the vein, the distance from the transducer to the wall of the vein is essentially the same in all radial directions. Thus, when the transducer 320 is centered, the A-mode display will show the ring-down pulse 602 and an echo pulse 702 that is "sharp", having a relatively large amplitude and relatively short duration. By contrast, when the transducer 320 is off-center, as shown in FIG. 7B, the distance from the transducer 320 to the wall of the vein will not be uniform. Thus, when the transducer 320 is off-center, the A-mode display will show the ring-down pulse 602 and an echo pulse 704,that is "smeared-out", having a relatively smaller amplitude and relatively longer duration.

The variation of the echo return times for an off-center transducer can advantageously be used to measure the position of the ablation element 120 with respect to the center of the vein. An array having a plurality of sensors, preferably three or more, can advantageously be used to measure the position of the ablation element 120 with respect to center. For example, FIGS. 8A–B show a portion of a catheter assembly with an array of four ultrasonic sensors 810–813 disposed in a circumferential pattern around the catheter 310. Each of the ultrasonic sensors is 810–813 used to produce an A-mode plot.

Figure 9A:
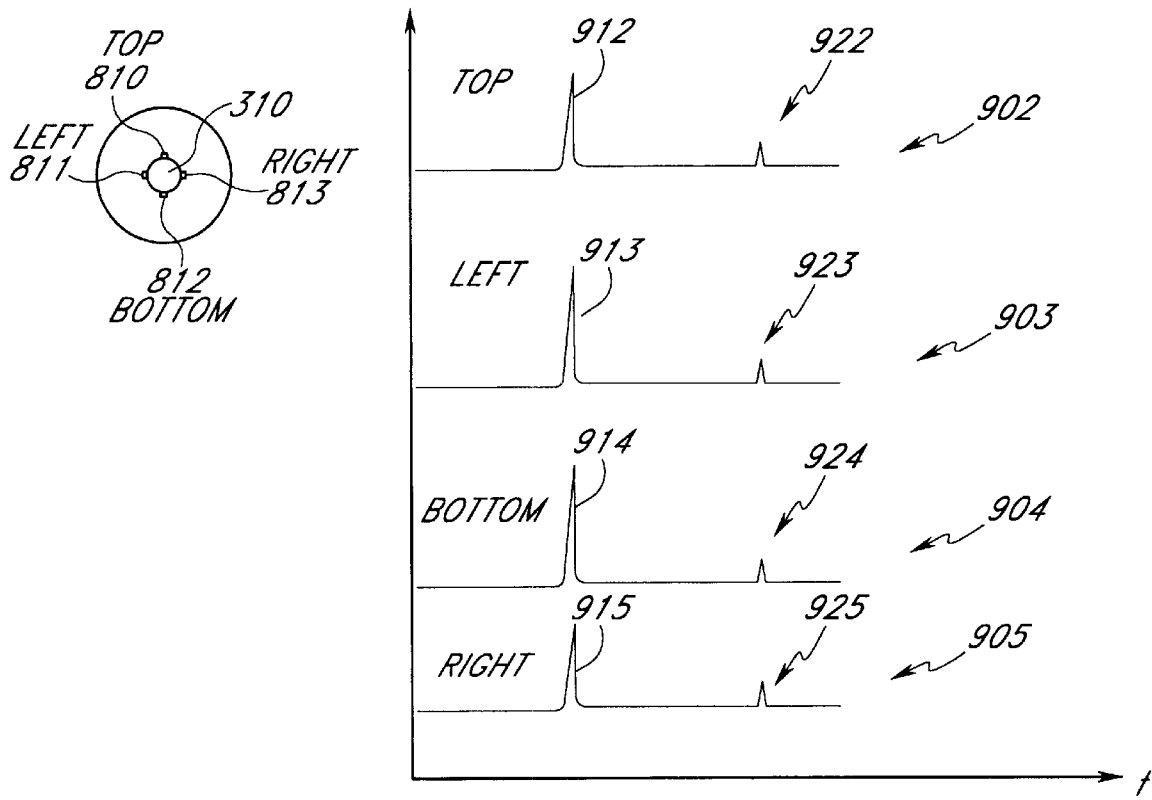
FIG. 9A shows downrange time-domain responses of the ultrasonic sensors shown in FIG. 8A when the catheter is centered in an ostium, as schematically illustrated.

FIG. 9A shows downrange time-domain responses of the ultrasonic sensors 810–813 when the catheter 310 is centered in a vein. The ultrasonic sensors 810–813 produce A-mode plots 902–905 respectively. Each of the plots 902–905 has a ring-down (t=0) pulse 912–915, respectively, and an echo pulse 922–925, respectively. For similar transducers, the ring-down pulses 912–915 are similar. When the catheter 310 is centered in the vein the echo pulses 922–925 will also be similar and occur at similar downrange distances (times).

Figure 9B:
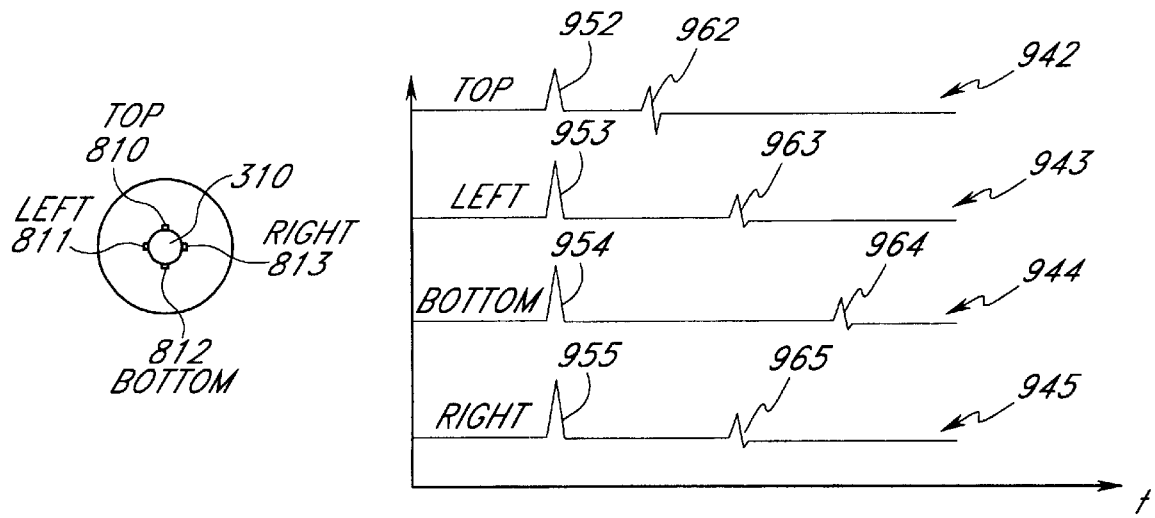
FIG. 9B shows downrange time-domain responses of the ultrasonic sensors shown in FIG. 8A when the catheter is positioned off-center in an ostium, as schematically illustrated.

FIG. 9B shows downrange time-domain responses of the ultrasonic sensors 810–813 when the catheter 310 is off-centered in a vein. In FIG. 9B, the catheter 310 is above center, and thus the top transducer 810 is closest to the wall, the left and right transducers 811, 813 are equidistant from the wall, and the bottom transducer 812 is furthest from the wall. FIG. 9B shows A-mode plots 942–945, each having;a ring-down pulse 952–955, respectively, and an echo pulse 962–965, respectively. For similar transducers, the ring-down pulses 952–955 are similar. Of the echo pulses 962–965, the echo pulse 962 is closest to the ring-down pulses and strongest. The echo pulses 963, 965 are approximately the same distance from the ring-down pulse. The echo pulse 964 is the furthest from the ring-down pulses and the weakest. A clinician seeing the plots 942–945 would know that the catheter 310 is above center in the vein and thus be able to manipulate the catheter and guidewire (e.g., by torquing or pulling the guidewire taught) to move the ablation member closer to center of the vein. If the ablation member is disposed on a deflectable or steerable delivery platform, the distal end of the delivery member can be moved to reposition the ablation member. Alternatively, a graphical representation, as is shown in FIG. 13 below, can be used to show the location of the array with respect to the center of the vein. This information can then be used to supply different power levels to a corresponding array of ablation devices (e.g., ultrasonic transducer segments as described below) that form at least part of the ablation element.

The array of transducers 810–813 can be constructed by attaching separate transducers to the catheter 310. Alternatively, the array of transducers 810–813 can be constructed by modify a single transducer to produce a multi-mode transducer.

Figure 10A:
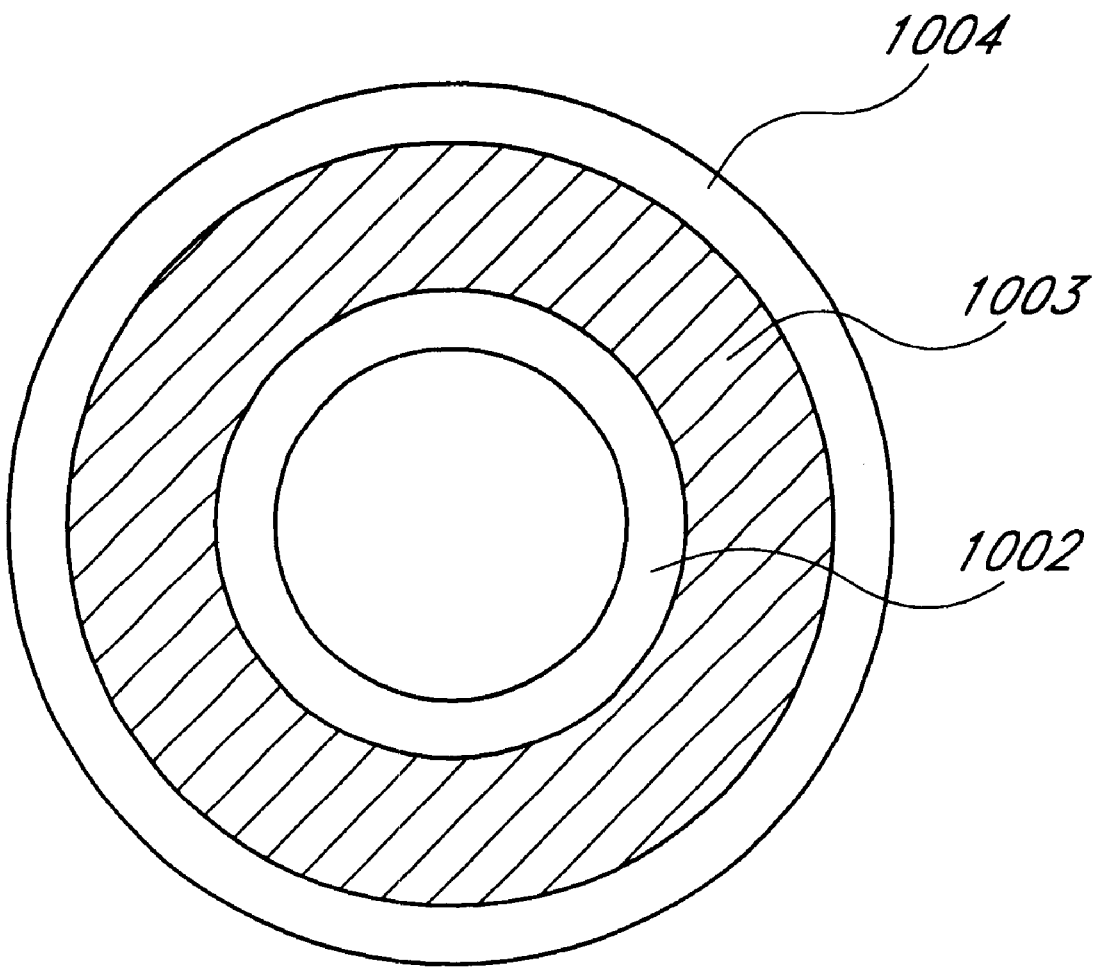
FIG. 10A is a transverse cross-section drawing showing construction of a cylindrical ultrasonic transducer having inner and outer electrodes.

FIG. 10A is a cross-section drawing showing construction of a single cylindrical ultrasonic transducer having a cylindrical inner electrode 1002, a cylindrical outer electrode 1004, and a cylindrical piezoelectric material 1003 between the electrodes. The piezoelectric material 1003 is a suitable material, such as, for example quartz, PZT, and the like, that exhibits a change in physical dimension in response to an impressed voltage. The piezoelectric material 1003 is oriented such that when a voltage is impressed between the electrodes 1002 and 1004, the thickness of the piezoelectric material 1003 changes slightly. Then the polarity of the impressed voltage is alternated at a ultrasonic frequency F the piezoelectric material 1003' will vibrate at the ultrasonic frequency F. The vibrations of the piezoelectric material 1003 produce ultrasonic sound waves. Since the electrodes are cylindrically symmetric, the piezoelectric material 1003 will vibrate radially, with cylindrical symmetry. Conversely, when an ultrasonic wave hits the piezoelectric material 1003, the ultrasonic wave will cause vibrations in the piezoelectric material.

These vibrations will generate a voltage between the electrodes 1002 and 1004. Thus, the transducer is a reciprocal device that can both transmit and receive ultrasonic waves.

Figure 10G:
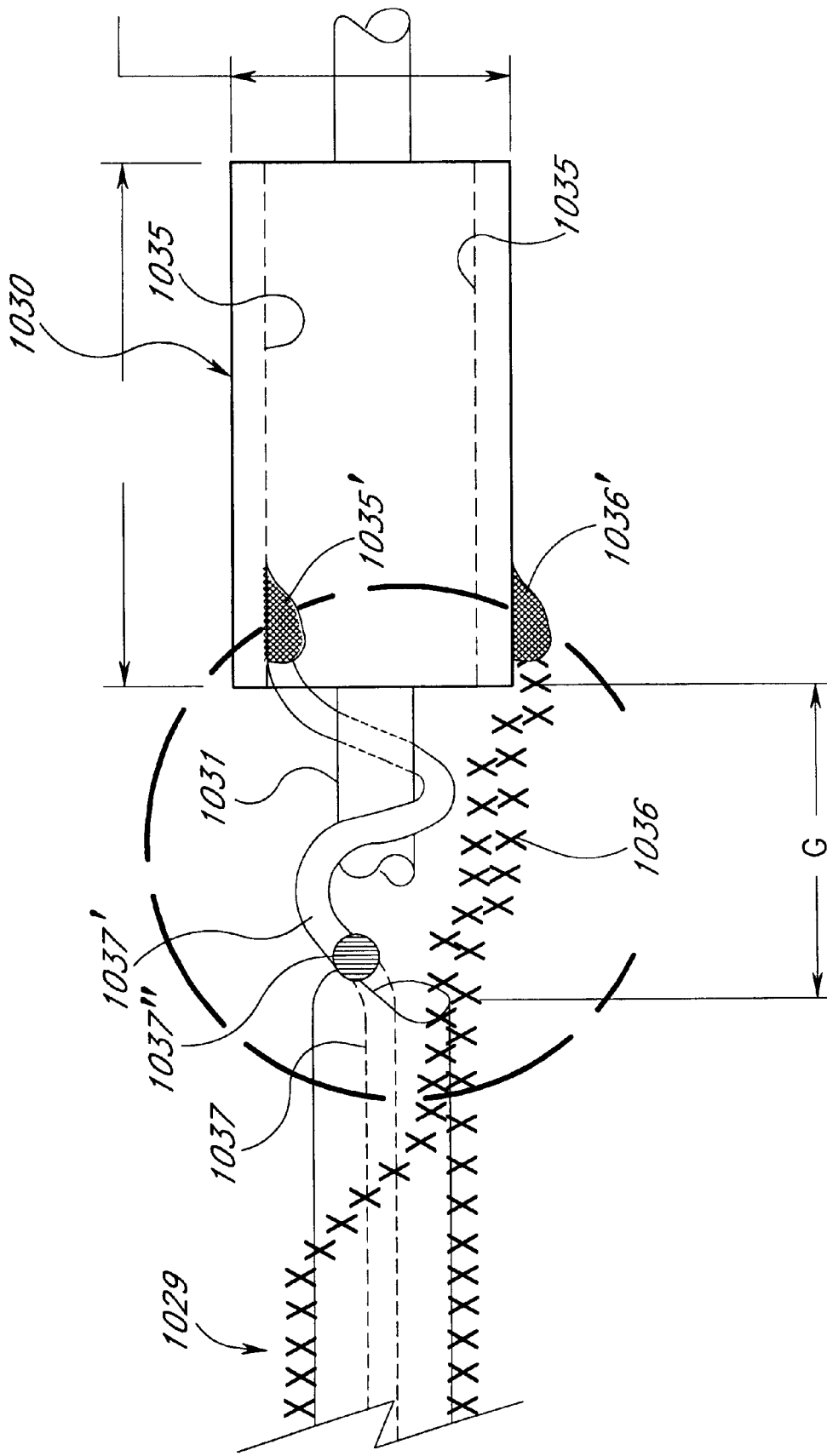
FIG. 10G shows a perspective view of an ultrasonic transducer in an overall assembly wherein the electrical leads are coupled from a coaxial cable assembly to the ultrasound transducer in a strain-relief design.
Figure 10H:
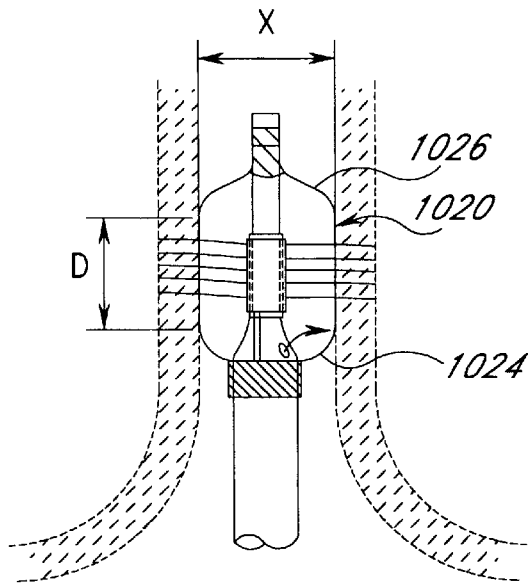
FIG. 10H shows a side view of a similar circumferential ablation catheter to the catheter shown in FIG. 10B, and shows the distal end portion of the circumferential ablation catheter during one mode of use in forming a circumferential conduction block in a pulmonary vein in the region of its ostium along a left atrial wall (shown in cross-section in phantom).
Figure 10I:
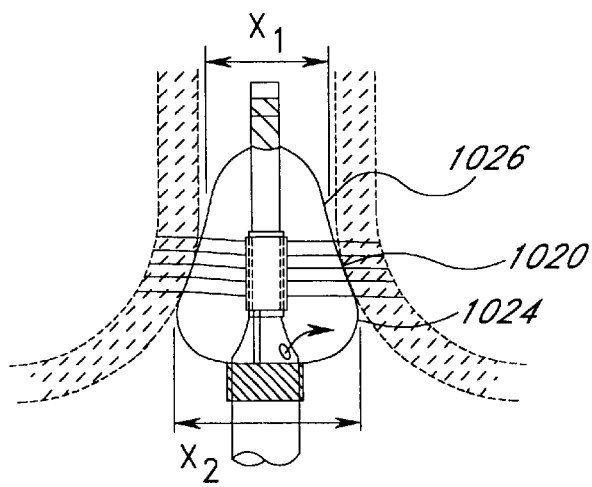
FIG. 10I shows a similar side view of a circumferential ablation catheter and pulmonary vein ostium (shown in cross-section in phantom) as that shown in FIG. 10H, but with the circumferential ablation catheter having a balloon with a tapered outer diameter.
Figure 10J:
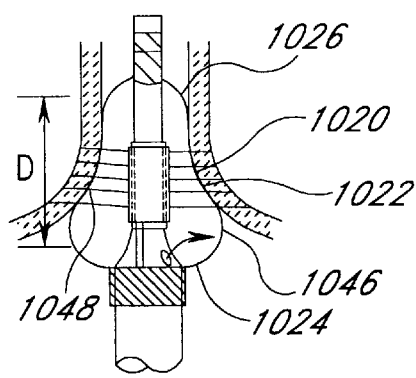
FIG. 10J shows a, similar view to that shown in FIGS. 10H–I, although showing another circumferential ablation catheter wherein the balloon has a "pear"-shaped outer diameter with a contoured surface along a taper which is adapted to seat in the ostium of a pulmonary vein.
Figure 10K:
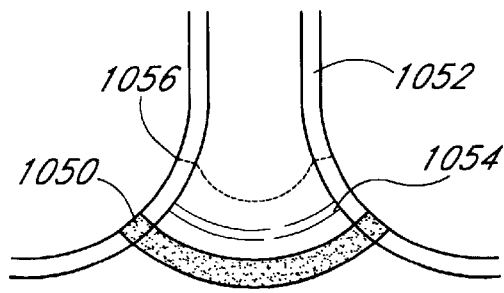
FIG. 10K shows a cross-sectional view of one circumferential conduction block which may be formed by use of a circumferential ablation catheter such as that shown in FIG. 10J, and shows in phantom another circumferential conduction block including a region of tissue within the pulmonary vein.
Figure 10L:
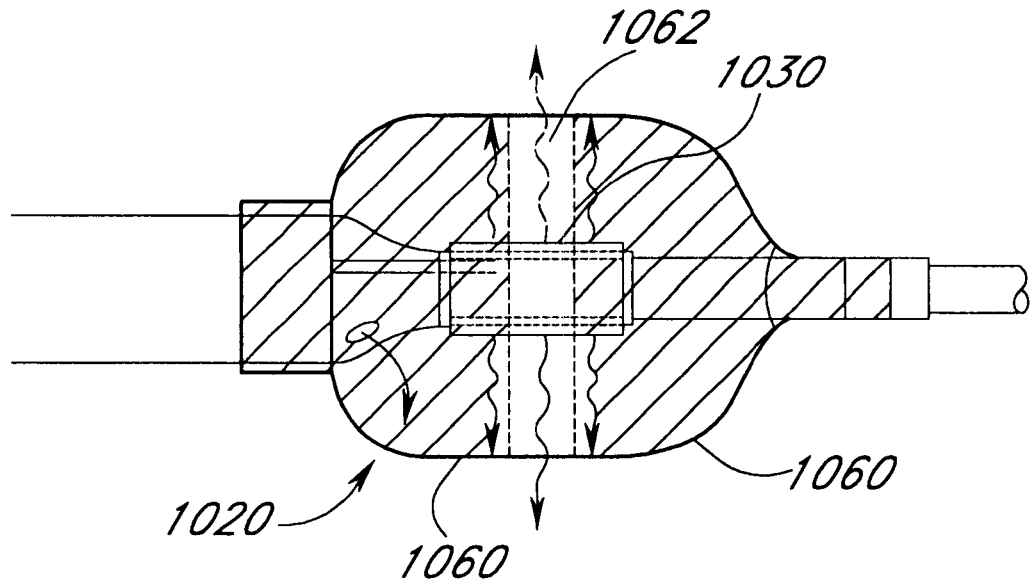
FIG. 10L shows a side view of the distal end portion of another circumferential ablation catheter for use with a., position monitoring assembly, wherein an outer shield or filter is provided along the balloon's outer surface in order to isolate sonic transmissions from the inner ultrasound transducer to only a narrow circumferential area which circumscribes a narrow circumferential band along an intermediate region of the working length of the balloon.
Figure 10M:
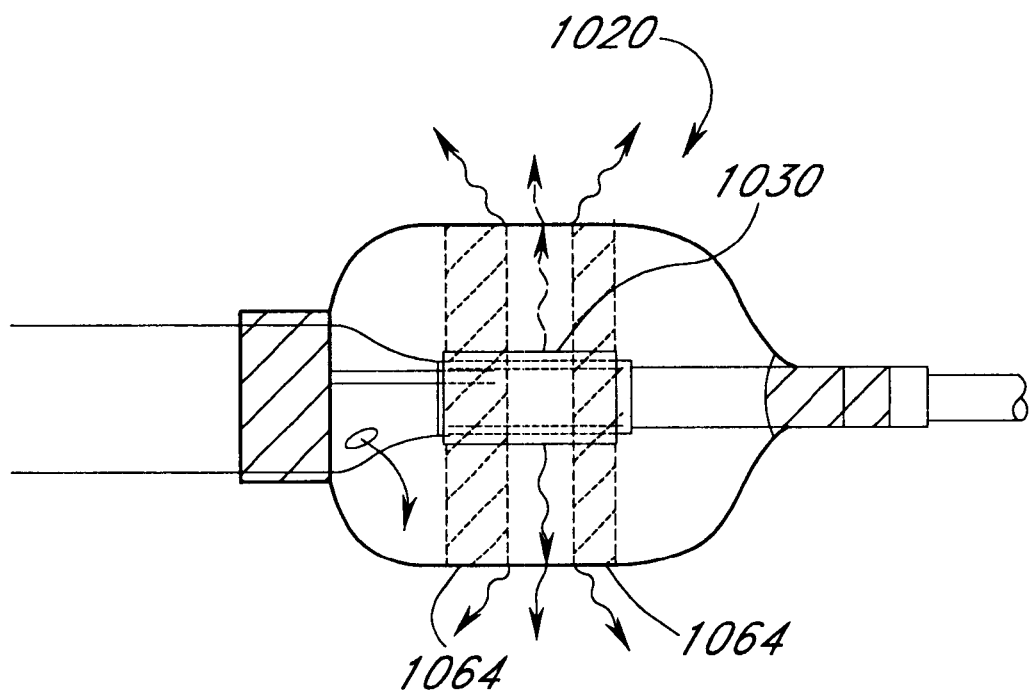
FIG. 10M shows a similar view as that shown in FIG. 10L, although showing the distal end portion of another circumferential ablation catheter which includes a heat sink as an equatorial band within the circumferential path of energy emission from an inner ultrasound transducer.
Figure 10O:
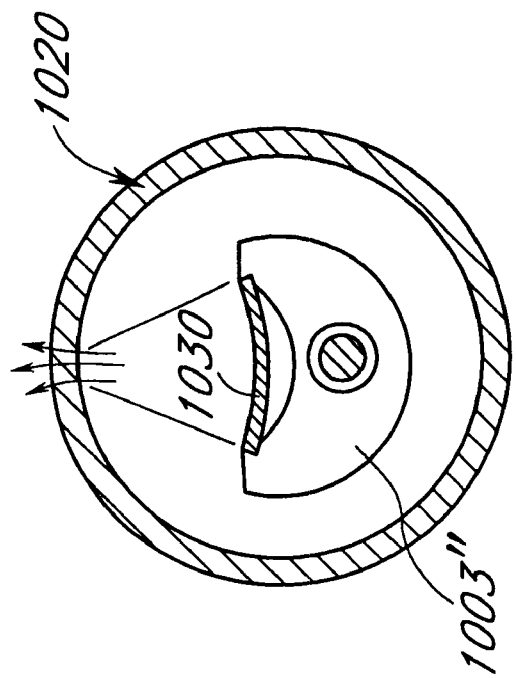
FIG. 10O shows a transverse cross-sectional view of an a further circumferential ablation catheter for use with a position monitoring assembly, and shows the ablation element to include a single curvilinear section that is mounted so as to position its concave surface facing in a radially outward direction.

FIGS. 10B–O variously show circumferential ablation device assemblies incorporating ultrasound transducers for ablating a circumferential region of tissue in order to form the desired conduction block to treat left atrial arrhythmia according to the present invention. Such ultrasound ablation assemblies are believed to be particularly amenable to use with the position monitoring assemblies incorporating sensing capabilities of the ablation transducer itself, such as for example but not limited to an "A."-mode sensing system. However, it is further contemplated that the particular ablation devices of FIGS. 10B–O may also be combined with the other position monitoring assemblies and related sensors also herein shown and described. Furthermore, such ultrasound ablation assemblies may also be combined with the various ablation monitoring assemblies, such as temperature monitoring assemblies and sensors, also elsewhere described in this disclosure.

As common to each of the following devices, a source of acoustic energy is provided a delivery device that also includes an anchoring mechanism. In one mode, the anchoring device comprises an expandable member that also positions the acoustic energy source within the body; however, other anchoring and positioning devices may also be used, such as, for example, a basket mechanism. In a more specific form, the acoustic energy source is located within the expandable member and the expandable member is adapted to engage a circumferential path of tissue either about or along a pulmonary vein in the region of its ostium along a left atrial wall. The acoustic energy source in turn is acoustically coupled to the wall of the expandable member and thus to the circumferential region of tissue engaged by the expandable member wall by emitting a circumferential and longitudinally collimated ultrasound signal when actuated by an acoustic energy driver. The use of acoustic energy, and particularly ultrasonic energy, offers the advantage of simultaneously applying a dose of energy sufficient to ablate a relatively large surface area within or near the heart to a desired heating depth without exposing the heart to a large amount of current. For example, a collimated ultrasonic transducer can form a lesion, which has about a 1.5 mm width, about a 2.5 mm diameter lumen, such as a pulmonary vein and of a sufficient depth to form an effective conductive block. It is believed that an effective conductive block can be formed by producing a lesion within the tissue that is transmural or substantially transmural. Depending upon the patient as well as the location within the pulmonary vein ostium, the lesion may have a depth of 1 millimeter to 10 millimeters. It has been observed that the collimated ultrasonic transducer can be powered to provide a lesion having these parameters so as to form an effective conductive block between the pulmonary vein and the posterior wall of the left atrium.

With specific reference now to the device illustrated in FIGS. 10B–E, a circumferential ablation device assembly 1001' includes an elongate body 1002' with proximal and distal end portions 1010, 1012, an expandable balloon 1020 located along the distal end portion 1012 of elongate body 1002', and a circumferential ultrasound transducer 1030 which forms a circumferential ablation member which is acoustically coupled to the expandable balloon 1020. In more detail, FIGS. 10B–D variously show elongate body 1002' to include guidewire lumen 1004', inflation lumen 1006, and electrical lead lumen 1008. The ablation device, however, can be of a self steering type rather than an over-the-wire type device.

Each lumen extends between a proximal port (not shown) and a respective distal port, which distal ports are shown as distal guidewire port 1005 for guidewire lumen 1004', distal inflation port 1007 for inflation lumen 1006, and distal lead port 1009 for electrical lead lumen 1008. Although the guidewire, inflation and electrical lead lumens are generally arranged in a side-by-side relationship; the elongate body 1002' can be constructed with one or more of these lumens arranged in a coaxial relationship, or in any of a wide variety of configurations that will be readily apparent to one of ordinary skill in the art.

In addition, the elongate body 1002' is also shown in FIGS. 10B and 10D to include an inner member 1003' which extends distally beyond distal inflation and lead ports 1007, 1009, through an interior chamber formed by the expandable balloon 1020, and distally beyond expandable balloon 1020 where the elongate body terminates in a distal tip. The inner member 1003' forms the distal region for the guidewire lumen 1004' beyond the inflation and lead ports, and also provides a support member for the cylindrical ultrasound transducer 1030 and for the distal neck of the expansion balloon, as described in more detail below.

One more detailed construction for the components of the elongate body 1002' which is believed to be suitable for use in transeptal left atrial ablation procedures is as follows. The elongate body 1002' itself may have an outer diameter provided within the range of from about 5 French to about 10 French, and more preferable from about 7 French to about 9 French. The guidewire lumen preferably is adapted to slideably receive guidewires ranging from about 0.010 inch to about 0.038inch in diameter, and preferably is adapted for use with guidewires ranging from about 0.018inch to about 0.035 inch in diameter. Where a 0.035 inch guidewire is to be used, the guidewire lumen preferably has an inner diameter of 0.040 inch to about 0.042 inch. In addition, the inflation lumen preferably has an inner diameter of about 0.020 inch in order to allow for rapid deflation times, although may vary based upon the viscosity of inflation medium used, length of the lumen, and other dynamic factors relating to fluid flow and pressure.

In addition to providing the requisite lumens and support members for the ultrasound transducer assembly, the elongate body 1002' of the present device must also be adapted to be introduced into the left atrium such that the distal end portion with balloon and transducer may be placed within the pulmonary vein ostium in a percutaneous translumenal procedure, and even more preferably in a transeptal procedure as otherwise herein provided. Therefore, the distal end portion 1012 is preferably flexible and adapted to track over and along a guidewire seated within the targeted pulmonary vein. In one further more detailed construction which is believed to be suitable, the proximal end portion is adapted to be at least 30% more stiff than the distal end portion. According to this relationship, the proximal end portion may be suitably adapted to provide push transmission to the distal end portion while the distal end portion is suitably adapted to track through bending anatomy during in vivo delivery of the distal end portion of the device into the desired ablation region.

Notwithstanding the specific device constructions just described, other delivery mechanisms for delivering the ultrasound ablation member to the desired ablation region are also contemplated. For example, while the FIG. 10B variation is shown as an "over-the-wire" catheter construction, other guidewire tracking designs may be suitable substitutes, such as, for example, catheter devices which are known as "rapid exchange" or "monorail" variations wherein the guidewire is only housed coaxially within a lumen of the catheter in the distal regions of the catheter. In another example, a deflectable tip design may also be a suitable substitute and which is adapted to independently select a desired pulmonary vein and direct the transducer assembly into the desired location for ablation. Further to this latter variation, the guidewire lumen and guidewire of the FIG. 10B variation may be replaced with a "pullwire" lumen and associated fixed pullwire which is adapted to deflect the catheter tip by applying tension along varied stiffness transitions along the catheter's length. Still further to this pullwire variation, acceptable pullwires may have a diameter within the range from about 0.008 inch to about 0.020 inch, and may further include a taper, such as, for example, a tapered outer diameter from about 0.020 inch to about 0.008 inch.

More specifically regarding expandable balloon 1020 as shown in varied detail between FIG. 10B and 10D, a central region 1022 is generally coaxially disposed over the inner member 1003' and is bordered at its end neck regions by proximal and distal adaptions 1024, 1026. The proximal adaption 1024 is sealed over elongate body 1002' proximally of the distal inflation and the electrical lead ports 1007, 1009, and the distal adaption 1026 is sealed over inner member 1003'. According to this arrangement, a fluid tight interior chamber is formed within expandable balloon 1020. This interior chamber is fluidly coupled to a pressurizeable fluid source (not shown) via inflation lumen 1006. In addition to the inflation lumen 1006, electrical lead lumen 1008 also communicates with the interior chamber of expandable balloon 1020 so that the ultrasound transducer 1030, which is positioned within that chamber and over the inner member 1003', may be electrically coupled to an ultrasound drive source or actuator, as will be provided in more detail below.

The expandable balloon 1020 may be constructed from a variety of known materials, although the balloon 1020 preferably is adapted to conform to the contour of a pulmonary vein ostium. For this purpose, the balloon material can be of the highly compliant variety or of a predefined shape, as noted above.

The ablation member, which is illustrated in FIGS. 10B–E, takes the form of annular ultrasonic transducer 1030. In the illustrated device, the annular ultrasonic transducer 1030 has a unitary cylindrical shape with a hollow interior (i.e., is tubular shaped); however, the transducer applicator 1030 can have a generally annular shape and be formed of a plurality of segments. For instance, the transducer applicator 1030 can be formed by a plurality of tube sectors that together form an annular shape. The tube sectors can also be of sufficient arc lengths so as when joined together, the sectors assembly forms a "clover-leaf shape". This shape is believed to provide overlap in heated regions between adjacent elements. The generally annular shape can also be formed by a plurality of planar transducer segments which are arranged in a polygon shape (e.g., hexagon). In addition, although in the illustrated device the ultrasonic transducer comprises a single transducer element, the transducer applicator can be formed of a multi-element array, as described in greater detail below.

As is shown in detail in FIG. 10E, cylindrical ultrasound transducer 1030 includes a tubular wall 1031 which includes three concentric tubular layers. The central layer 1032 is a tubular shaped member of a piezoceramic or piezoelectric crystalline material. The transducer preferably is made of type PZT-4, PZT-5 or PZT-8, quartz or Lithium-Niobate type piezoceramic material to ensure high power output capabilities. These types of transducer materials are commercially available from Stavely Sensors, Inc. of East Hartford, Conn., or from Valpey-Fischer Corp. of Hopkinton, Mass.

The outer and inner tubular members 1033, 1034 enclose central layer 1032 within their coaxial space and are constructed of an electrically conductive material. In the illustrated device, these transducer electrodes 1033, 1034 comprise a metallic coating, and more preferably a coating of nickel, copper, silver, gold, platinum, or alloys of these metals.

One more detailed construction for a cylindrical ultrasound transducer for use in the present application is as follows. The length of the transducer 1030 or transducer assembly (e.g., multi-element array of transducer elements) desirably is selected for a given clinical application. In connection with forming circumferential condition blocks in cardiac or pulmonary vein wall tissue, the transducer length can fall within the range of approximately 2 mm up to greater than 10 mm, and preferably equals about 5 mm to 10 mm. A transducer accordingly sized is believed to form a lesion of a width sufficient to ensure the integrity of the formed conductive block without undue tissue ablation. For other applications, however, the length can be significantly longer.

Likewise, the transducer outer diameter desirably is selected to account for delivery through a particular access path (e.g., percutaneously and transeptally), for proper placement and location within a particular body space, and for achieving a desired ablation effect. In the given application within or proximate of the pulmonary vein ostium, the transducer 1030 preferably has an outer diameter within the range of about 1.8 mm to greater than 2.5 mm. It has been observed that a transducer with an outer diameter of about 2 mm generates acoustic power levels approaching 20 Watts per centimeter radiator or greater within myocardial or vascular tissue, which is believed to be sufficient for ablation of tissue engaged by the outer balloon for up to about 2 cm outer diameter of the balloon. For applications in other body spaces, the transducer applicator 1030 may have an outer diameter within the range of about 1 mm to greater than 3–4 mm (e.g., as large as 1 to 2 cm for applications in some body spaces).

The central layer 1032 of the transducer 1030 has a thickness selected to produce a desired operating frequency. The operating frequency will vary of course depending upon clinical needs, such as the tolerable outer diameter of the ablation and the depth of heating, as well as upon the size of the transducer as limited by the delivery path and the size of the target site. As described in greater detail below, the transducer 1030 in the illustrated application preferably operates within the range of about 5 MHz to about 20 MHz, and more preferably within the range of about 7 MHz to about 10 MHz. Thus, for example, the transducer can have a thickness of approximately 0.3 mm for an operating frequency of about 7 MHz (i.e., a thickness generally equal to ½ the wavelength associated with the desired operating frequency).

The transducer 1030 is vibrated across the wall thickness and to radiate collimated acoustic energy in the radial direction. For this purpose, as best seen in FIGS.10B and 10E, the distal ends of electrical leads 1036, 1037 are electrically coupled to outer and inner tubular members or electrodes 1033, 1034, respectively, of the transducer 1030, such as, for example, by soldering the leads to the metallic coatings or by resistance welding. In the illustrated device, the electrical leads are 4–8 mil (0.004 to 0.008 inch diameter) silver wire or the like.

The proximal ends of these leads are adapted to couple to an ultrasonic driver or actuator 1040, which is schematically illustrated in FIG. 10E. FIGS. 10B–E further show leads 1036, 1037 as separate wires within electrical lead lumen 1008, in which configuration the leads must be well insulated when in close contact. Other configurations for leads 1036, 1037 are therefore contemplated. For example, a coaxial cable may provide one cable for both leads which is well insulated as to inductance interference, as further developed below by reference to FIG. 10G. Or, the leads may be communicated toward the distal end portion 1012 of the elongate body through different lumens which are separated by the catheter body.

The transducer also can be sectored by scoring or notching the outer transducer electrode 1033 and part of the central layer 1032 along lines parallel to the longitudinal axis L of the transducer 1030, as illustrated in FIG. 10F. A separate electrical lead connects to each sector in order to couple the sector to a dedicated power control that individually excites the corresponding transducer sector. By controlling the driving power and operating frequency to each individual sector, the ultrasonic driver 1040 can enhance the uniformity of the ultrasonic beam around the transducer 1030, as well as can vary the degree of heating (i.e., lesion control) in the angular dimension.

The ultrasound transducer just described is combined with the overall device assembly according to the present device as follows. In assembly, the transducer 1030 desirably is "air-backed" to produce more energy and to enhance energy distribution uniformity, as known in the art. In other words, the inner member 1003' does not contact an appreciable amount of the inner surface of transducer inner tubular member 1034. This is because the piezoelectric crystal which forms central layer 1032 of ultrasound transducer 1030 is adapted to radially contract and expand (or radially "vibrate") when an alternating current is applied from a current source and across the outer and inner tubular electrodes 1033, 1034 of the crystal via the electrical leads 1036, 1037. This controlled vibration emits the ultrasonic energy which is adapted to ablate tissue and form a circumferential conduction block according to the present device. Therefore, it is believed that appreciable levels of contact along the surface of the crystal may provide a dampening effect which would diminish the vibration of the crystal and thus limit the efficiency of ultrasound transmission.

For this purpose, the transducer 1030 seats coaxially about the inner member 1003' and is supported about the inner member 1003' in a manner providing a gap between the inner member 1003' and the transducer inner tubular member 1034. That is, the inner tubular member 1034 forms an interior bore 1035 which loosely receives the inner member 1003'. Any of a variety of structures can be used to support the transducer 1030 about the inner member 1003'. For instance, spaces or splines can be used to coaxially position the transducer 1030 about the inner member 1003' while leaving a generally annular space between these components. In the alternative, other conventional and known approaches to support the transducer can also be used. For instance, 0-rings that circumscribe the inner member 1003' and lie between the inner member and the transducer 1030 can support the transducer 1030 in a manner similar to that illustrated in U.S. Pat. No. 5,606,974, issued Mar. 4, 1997, and entitled "Catheter Having Ultrasonic Device." More detailed examples of the alternative transducer support structures just described are respectfully disclosed in the following references: U.S. Pat. No. 5,620,479 to Diederich, issued Apr. 15, 1997, and entitled "Method and Apparatus for Thermal Therapy of Tumors," and U.S. Pat. No. 5,606,974 to Castellano, issued Mar. 4, 1997, and entitled "Catheter Having Ultrasonic Device." The disclosures of these references are herein incorporated in their entirety by reference thereto.

In the illustrated device, a stand-off 1038 is provided in order to ensure that the transducer 1030 has a radial separation from the inner member 1003' to form a gap filled with air and/or other fluid. In one preferred mode shown in FIG. 10D, stand-off 1038 is a tubular member with a plurality of circumferentially spaced outer splines 1039 which hold the majority of the transducer inner surface away from the surface of the stand-off between the splines, thereby minimizing dampening affects from the coupling of the transducer to the catheter. The tubular member which forms a stand-off such as stand-off 1039 in the FIG. 10D device may also provide its inner bore as the guidewire lumen in the region of the ultrasound transducer, in the alternative to providing a separate stand-off coaxially over another tubular member which forms the inner member, such as according to the FIG. 10D device.

In a further mode, the elongate body 1002' can also include additional lumens which lie is either side by side to or coaxial with the guidewire lumen 1004' and which terminate at ports located within the space between the inner member 1003' and the transducer 1030. A cooling medium can circulate through space defined by the stand-off 1038 between the inner member 1003' and the transducer 1030 via these additional lumens. By way of example, carbon dioxide gas, circulated at a rate of 5 liters per minute, can be used as a suitable cooling medium to maintain the transducer at a lower operating temperature. It is believed that such thermal cooling would allow more acoustic power to transmit to the targeted tissue without degradation of the transducer material.

The transducer 1030 desirably is electrically and mechanically isolated from the interior of the balloon 1020. Again, any of a variety of coatings, sheaths, sealants, tubings and the like may be suitable for this purpose, such as those described in U.S. Pat. Nos. 5,620,479 and 5,606,974. In the illustrated device, as best illustrated in FIG. 10D, a conventional, flexible, acoustically compatible, and medical grade epoxy 1042 is applied over the transducer 1030. The epoxy 1042 may be, for example, Epotek 301, Epotek 310, which is available commercially from Epoxy Technology, or Tracon FDA-8. In addition, a conventional sealant, such as, for example, General Electric Silicon II gasket glue and sealant, desirably is applied at the proximal and distal ends of the transducer 1030 around the exposed portions of the inner member 1003', wires 1036, 1037 and stand-off 1038 to seal the space between the transducer 1030 and the inner member 1003' at these locations.

An ultra thin-walled polyester heat shrink tubing 1044 or the like then seals the epoxy coated transducer. Alternatively, the epoxy covered transducer 1030, inner member 1003' and stand-off 1038 can be instead inserted into a tight thin wall rubber or plastic tubing made from a material such as Teflon®, polyethylene, polyurethane, silastic or the like. The tubing desirably has a thickness of 0.0005 to 0.003 inches.

When assembling the ablation device assembly, additional epoxy is injected into the tubing after the tubing is placed over the epoxy-coated transducer 1030. As the tube shrinks, excess epoxy flows out and a thin layer of epoxy remains between the transducer and the heat shrink tubing 1044. These layers 1042, 1044 protect the transducer surface, help acoustically match the transducer 1030 to the load, make the ablation device more robust, and ensure airtight integrity of the air backing.

Although not illustrated in FIG. 10B in order to simplify the drawing, the tubing 1044 extends beyond the ends of transducer 1030 and surrounds a portion of the inner member 1003' on either side of the transducer 1030. A filler (not shown) can also be used to support the ends of the tubing 1044. Suitable fillers include flexible materials such as, for example, but without limitation, epoxy, Teflon® tape and the like.

The ultrasonic actuator 1040 generates alternating current to power the transducer 1030. The ultrasonic actuator 1040 drives the transducer 1030 at frequencies within the range of about 5 to about 20 MHz, and preferably for the illustrated application within the range of about 7 MHz to about 10 MHz. In addition, the ultrasonic driver can modulate the driving frequencies and/or vary power in order to smooth or unify the produced collimated ultrasonic beam. For instance, the function generator of the ultrasonic actuator 1040 can drive the transducer at frequencies within the range of 6.8 MHz and 7.2 MHz by continuously or discretely sweeping between these frequencies.

The ultrasound transducer 1030 of the present device sonically couples with the outer skin of the balloon 1020 in a manner which forms a circumferential conduction block in a pulmonary vein as follows. Initially, the ultrasound transducer is believed to emit its energy in a circumferential pattern which is highly collimated along the transducer's length relative to its longitudinal axis L (see FIG. 10F). The circumferential band therefore maintains its width and circumferential pattern over an appreciable range of diameters away from the source at the transducer. Also, the balloon is preferably inflated with fluid which is relatively ultrasonically transparent, such as, for example, degassed water. Therefore, by actuating the transducer 1030 while the balloon 1020 is inflated, the circumferential band of energy is allowed to translate through the inflation fluid and ultimately sonically couple with a circumferential band of balloon skin which circumscribes the balloon 1020. Moreover, the circumferential band of balloon skin material may also be further engaged along a circumferential path of tissue which circumscribes the balloon, such as, for example, if the balloon is inflated within and engages a pulmonary vein wall, ostium, or region of atrial wall. Accordingly, where the balloon is constructed of a relatively ultrasonically transparent material, the circumferential band of ultrasound energy is allowed to pass through the balloon skin and into the engaged circumferential path of tissue such that the circumferential path of tissue is ablated.

Further to the transducer-balloon relationship just described, the energy is coupled to the tissue largely via the inflation fluid and balloon skin. It is believed that, for in vivo uses of the present invention, the efficiency of energy coupling to the tissue, and therefore ablation efficiency, may significantly diminish in circumstances where there is poor contact and conforming interface between the balloon skin and the tissue. Accordingly, it is contemplated that several different balloon types may be provided for ablating different tissue structures so that a particular shape may be chosen for a particular region of tissue to be ablated.

In one particular balloon-transducer combination shown in FIG. 10B, the ultrasound transducer preferably has a length such that the ultrasonically coupled band of the balloon skin, having a similar length d according to the collimated electrical signal, is shorter than the working length D of the balloon. According to this aspect of the relationship, the transducer is adapted as a circumferential ablation member which is coupled to the balloon to form an ablation element along a circumferential band of the balloon, therefore forming a circumferential ablation element band which circumscribes the balloon. Preferably, the transducer has a length which is less than two-thirds the working length of the balloon, and more preferably is less than one-half the working length of the balloon. By sizing the ultrasonic transducer length d smaller than the working length D of the balloon 1020 —and hence shorter than a longitudinal length of the engagement area between the balloon 1020 and the wall of the body space (e.g., pulmonary vein ostium)—and by generally centering the transducer 1030 within the balloon's working length D, the transducer 1030 operates in a field isolated from the blood pool. A generally equatorial position of the transducer 1030 relative to the ends of the balloon's working length also assists in the isolation of the transducer 1030 from the blood pool. It is believed that the transducer placement according to this arrangement may be preventative of thrombus formation which might otherwise occur at a lesion sight, particularly in the left atrium.

The ultrasound transducer described in various levels of detail above has been observed to provide a suitable degree of radiopacity for locating the energy source at a desired location for ablating the conductive block. However, it is further contemplated that the elongate body 1002' may include an additional radiopaque marker or markers (not shown) to identify the location of the ultrasonic transducer 1030 in order to facilitate placement of the transducer at a selected ablation region of a pulmonary vein via X-ray visualization. The radiopaque marker is opaque under X-ray, and can be constructed, for example, of a radiopaque metal such as gold, platinum, or tungsten, or can comprise a radiopaque polymer such as a metal loaded polymer. The radiopaque marker is positioned coaxially over an inner tubular member 1003'.

The present circumferential ablation device is introduced into a pulmonary vein of the left atrium in a manner similar to that described above. Once properly positioned within the pulmonary vein or vein ostium, the pressurized fluid source inflates the balloon 1020 to engage the lumenal surface of the pulmonary vein ostium. Once properly positioned, the ultrasonic driver 1040 is energized to drive the transducer 1030. It is believed that by driving the ultrasonic transducer 1030 at 20 acoustical watts at an operating frequency of 7 megahertz, that a sufficiently sized lesion can be formed circumferentially about the pulmonary vein ostium in a relatively short period of time (e.g., 1 to 2 minutes or less). It is also contemplated that the control level of energy can be delivered, then tested for lesion formation with a test stimulus in the pulmonary vein, either from an electrode provided at the tip area of the ultrasonic catheter or on a separate device such as a guidewire through the ultrasonic catheter. Therefore, the procedure may involve ablation at a first energy level in time, then check for the effective conductive block provided by the resulting lesion, and then subsequent ablations and testing until a complete conductive block is formed.

In addition or in the alternative, the circumferential ablation device may also include feedback control, for example, if thermocouples are provided at the circumferential element formed along the balloon outer surface. Monitoring temperature at this location provides indicia for the progression of the lesion. This feedback feature may be used in addition to or in the alternative to the multi-step procedure described above.

FIG. 10G shows one particular device wherein a coaxial cable 1029 provides electrical leads 1036, 1037 that couple to ultrasound transducer 1030 in a strain relief assembly (designated within shadowed circle) which has been observed to provide a robust lead-transducer coupling with minimized risk of fracturing or otherwise degrading the joints between these members.

More particularly, the strain relief assembly shown in FIG. 10G is formed by separating lead 1036 and lead 1037 from coaxial cable 1029. A connector lead 1037' is then soldered to inner surface 1035 of transducer 1030, after which connector lead 1037 is coiled around inner member 1031 and then soldered to the distal terminus of lead 1037 to form solder joint 1037". Lead 1036 is formed from the braided outer jacket of coaxial cable 1029, which is pushed to one side of cable 1029 and twisted and soldered to the outer electrode surface of transducer 1030, as shown at joint 1036'. In one particular device of this arrangement which has been observed to be suitable, the distance of gap G between the distal terminus of cable 1029 and transducer 1030 may be from 1 to 5 millimeters wherein the coiled connector lead 1037' has an outer diameter of 0.15 mm, and the transducer has an outer diameter from 2.0 to 2.5 millimeters and a length of approximately 5 millimeters. According to the FIG. 10G variation, joint 1035' is strain relieved and longitudinal tension on joint 1035' is minimized when the overall assembly is placed within a bend, such as for example while deflecting or tracking the assembly around tortuous bends to deliver the ablation element to the region to be ablated.

FIGS. 10H–K show various alternative devices of an ablation member for the purpose of illustrating the relationship between the ultrasound transducer and balloon of the member just described above. More specifically, FIG. 10H shows the balloon 1020 having a "straight" configuration with a working length D and a relatively constant diameter X between proximal and distal tapers 1024, 1026. As is shown in FIG. 10H, this variation is believed to be particularly well adapted for use in forming a circumferential conduction block along a circumferential path of tissue which circumscribes and transects a pulmonary vein wall. However, unless the balloon is constructed of a material having a high degree of compliance and conformability, this shape may provide for gaps in contact between the desired circumferential band of tissue and the circumferential band of the balloon skin along the working length of the balloon 1020.

The balloon 1020 in FIG. 10H is also concentrically positioned relative to the longitudinal axis of the elongate body. It is understood, however, that the balloon can be asymmetrically positioned on the elongate body, and that the ablation device can include more than one balloon.

FIG. 10I shows another assembly, although this assembly includes a balloon 1020 which has a tapered outer diameter from a proximal outer diameter $X_1$ to a smaller distal outer diameter $X_2$. (Like reference numerals have been used in each of these devices in order to is identify generally common elements between the devices.) According to this mode, this tapered shape is believed to conform well to other tapering regions of space, and may also be particularly beneficial for use in engaging and ablating circumferential paths of tissue along a pulmonary vein ostium.

FIG. 10J further shows a similar shape for the balloon as that just illustrated by reference to FIG. 10I, except that the FIG. 10J device further includes a balloon 1020 and includes a bulbous proximal end 1046. In the illustrated device, the proximate bulbous end 1046 of the central region 1022 gives the balloon 1020 a "pear" shape. More specifically, a contoured surface 1048 is positioned along the tapered working length D and between proximal shoulder 1024 and the smaller distal shoulder 1026 of balloon 1020. As is suggested by view of FIG. 10J, this pear shaped device is believed to be beneficial for forming the circumferential conduction block along a circumferential path of atrial wall tissue which surrounds and perhaps includes the pulmonary vein ostium. For example, the device shown in FIG. 10J is believed to form a similar lesion to that shown at circumferential lesion 1050 in FIG. 10K. Circumferential lesion 1050 electrically isolates the respective pulmonary vein 1052 from a substantial portion of the left atrial wall. The device shown in FIG. 10J is also believed to be suited to form an elongate lesion which extends along a substantial portion of the pulmonary vein ostium 1054, e.g., between the proximal edge of the illustrated lesion 1050 and the dashed line 1056 which schematically marks a distal edge of such an exemplary elongate lesion 1050.

As mentioned above, the transducer 1030 can be formed of an array of multiple transducer elements that are arranged in series and/or coaxial. The transducer can also be formed to have a plurality of longitudinal sectors. These modes of the transducer have particular utility in connection with the tapering balloon designs illustrated in FIGS. 10I and 10J. In these cases, because of the differing distances along the length of the transducer between the transducer and the targeted tissue, it is believed that a non-uniform heating depth could occur if the transducer were driven at a constant power. In order to uniformly heat the targeted tissue along the length of the transducer assembly, more power may therefore be required at the proximal end than at the distal end because power falls off as 1/radius from a in source (i.e., from the transducer) in water. Moreover, if the transducer 1030 is operating in an attenuating fluid, then the desired power level may need to account for the attenuation caused by the fluid. The region of smaller balloon diameter near the distal end thus requires less transducer power output than the region of larger balloon diameter near the proximal end. Further to this premise, in a more specific device, transducer elements or sectors, which are individually powered, can be provided and produce a tapering ultrasound power deposition. That is, the proximal transducer element or sector can be driven at a higher power level than the distal transducer element or sector so as to enhance the uniformity of heating when the transducer lies skewed relative to the target site.

The circumferential ablation device can also include additional mechanisms to control the depth of heating. For instance, the elongate body can include an additional lumen which is arranged on the body so as to circulate the inflation fluid through a closed system. A heat exchanger can remove heat from the inflation fluid and the flow rate through the closed system can be controlled to regulate the temperature of the inflation fluid. The cooled inflation fluid within the balloon 1020 can thus act as a heat sink to conduct away some of the heat from the targeted tissue and maintain the tissue below a desired temperature (e.g., 90° C.), and thereby increase the depth of heating. That is, by maintaining the temperature of the tissue at the balloon/tissue interface below a desired temperature, more power can be deposited in the tissue for greater penetration. Conversely, the fluid can be allowed to warm. This use of this feature and the temperature of the inflation fluid can be varied from procedure to procedure, as well as during a particular procedure, in order to tailor the degree of ablation to a given application or patient.

The depth of heating can also be controlled by selecting the inflation material to have certain absorption characteristics. For example, by selecting an inflation material with higher absorption than water, less energy will reach the balloon wall, thereby limiting thermal penetration into the tissue. It is believed that the following fluids may be suitable for this application: vegetable oil, silicone oil and the like.

Uniform heating can also be enhanced by rotating the transducer within the balloon. For this purpose, the transducer 1030 may be mounted on a torquible member which is movably engaged within a lumen that is formed by the elongate body.

Another aspect of the balloon-transducer relationship of the present device is also illustrated by reference to FIGS. 10L–M. In general as to the variations embodied by those figures, the circumferential ultrasound energy signal is modified at the balloon coupling level such that a third order of control is provided for the tissue lesion pattern (the first order of control is the transducer properties affecting signal emission, such as length, width, shape of the transducer crystal; the second order of control for tissue lesion pattern is the balloon shape, per above by reference to FIGS. 10H–J).

More particularly, FIG. 10L shows balloon 1020 to include a filter 1060 which has a predetermined pattern along the balloon surface and which is adapted to shield tissue from the ultrasound signal, for example, by either absorbing or reflecting the ultrasound signal. In the particular variation shown in FIG. 10L, the filter 1060 is patterned so that the energy band which is passed through the balloon wall is substantially more narrow than the band which emits from the transducer 1030 internally of the balloon 1020. The filter 1060 can be constructed, for example, by coating the balloon 1020 with an ultrasonically reflective material, such as with a metal, or with an ultrasonically absorbent material, such as with a polyurathane elastomer. Or, the filter 1060 can be formed by varying the balloon's wall thickness such that a circumferential band 1062, which is narrow in the longitudinal direction as compared to the length of the balloon, is also thinner (in a radial direction) than the surrounding regions, thereby preferentially allowing signals to pass through the band 1062. The thicker walls of the balloon 1020 on either side of the band 1062 inhibit propagation of the ultrasonic energy through the balloon skin at these locations.

For various reasons, the "narrow pass filter" device of FIG. 10L may be particularly well suited for use in forming circumferential conduction blocks in left atrial wall and pulmonary vein tissues according to the present invention. It is believed that the efficiency of ultrasound transmission from a piezoelectric transducer is limited by the length of the transducer, which limitations are further believed to be a function of the wavelength of the emitted signal. Thus, for some applications a transducer 1030 may be required to be longer than the length which is desired for the lesion to be formed. Many procedures intending to form conduction blocks in the left atrium or pulmonary veins, such as, for example, less-invasive "maz"-type procedures, require only enough lesion width to create a functional electrical block and to electrically isolate a tissue region. In addition, limiting the amount of damage formed along an atrial wall, even in a controlled ablation procedure, pervades as a general concern. However, a transducer that is necessary to form that block, or which may be desirable for other reasons, may require a length which is much longer and may create lesions which are much wider than is functionally required for the block. A "narrow pass" filter along the balloon provides one solution to such competing interests.

FIG. 10M shows another variation of the balloon-transducer relationship in an ultrasound ablation assembly according to the present invention. Unlike the variation shown in FIG. 10L, FIG. 10M shows placement of an ultrasonically absorbent band 1064 along balloon 1020 and directly in the central region of the emitted energy signal from transducer 1030. According to this variation, the ultrasonically absorbent band 1064 is adapted to heat to a significant temperature rise when sonically coupled to the transducer via the ultrasound signal. It is believed that some ablation methods may benefit from combining ultrasound/thermal conduction modes of ablation in a targeted circumferential band of tissue. In another aspect of this variation, ultrasonically absorbent band 1064 may operate as an energy sink as an aid to control the extent of ablation to a less traumatic and invasive level than would be reached by allowing the raw ultrasound energy to couple directly to the tissue. In other words, by heating the absorbent band 1064 the signal is diminished to a level that might have a more controlled depth of tissue ablation. Further to this aspect, absorbent band 1064 may therefore also have a width which is more commensurate with the length of the transducer, as is shown in an alternative mode in shadow at absorbent band 1064.

It is further contemplated that, where outer shields, absorbant bands, or sinks are placed over and around the ultrasound transducer (as in FIGS. 10L–M), use of the transducer as a position monitoring sensor, as described herein according to various devices, may be affected. For example, the ultrasonic shield or sink may produce a pronounced signal reflecting the distance of the expanded balloon from the transducer, which signal may mask or otherwise affect the ability to sense the signal that represents the desired anatomical information radially disposed from the ablation region along the balloon. Therefore, signal processing or other means to recognize distinctive characteristics of the desired anatomical signal may be required to decipher between the anatomical ultrasound data and sensed ultrasound data from the shield(s) or sink(s).

Figure 10N:
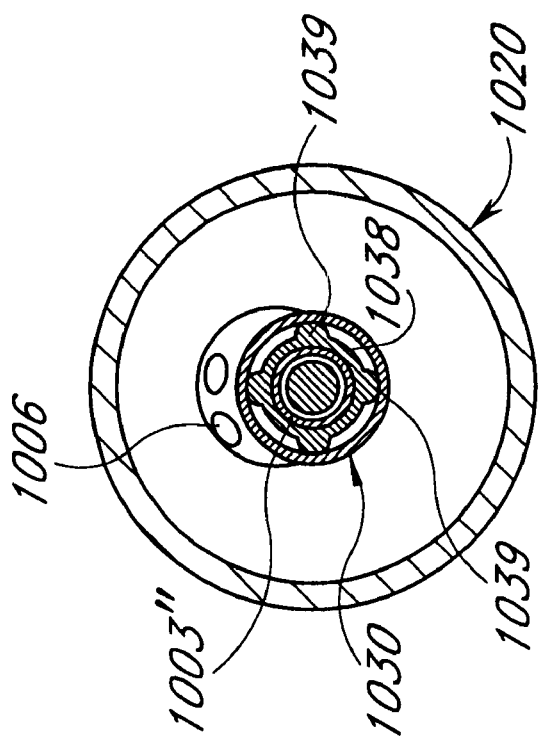
FIG. 10N shows a transverse cross-sectional view of an additional circumferential ablation catheter, and shows the ablation element to include a single transducer sector segment which is positioned along an inner member within an expandable balloon which is further shown in a radially expanded condition.

In each of the devices illustrated in FIGS. 10B–M, the ultrasonic transducer had an annular shape so as to emit ultrasonic energy around the entire circumference of the balloon. The present circumferential ablation device, however, can emit a collimated beam of ultrasonic energy in a specific angular exposure. For instance, as seen in FIG. 10N, the transducer can be configured to have only a single active sector (e.g., 180° exposure). The transducer can also have a planar shape. By rotating the elongate body, the transducer 1030 can be swept through 360° in order to form a circumferential ablation. For this purpose, the transducer 1030 may be mounted on a torquible member 1003", in the manner described above.

FIG. 10 illustrates another type of ultrasonic transducer which can be mounted to a torquible member 1003" within the balloon 1020. The transducer 1030 is formed by curvilinear section and is mounted on the inner member 1003" with its concave surface facing in a radially outward direction. The inner member 1003" desirably is formed with recess that substantially matches a portion of the concave surface of the transducer 1030. The inner member 1003" also includes longitudinal ridges on the edges of the recess that support the transducer above the inner member such that an air gap is formed between the transducer and the inner member. In this manner, the transducer is "air-backed." This spaced is sealed and closed in the manner described above in connection with the device of FIGS. 10B–G.

The inverted transducer section produces a highly directional beam pattern. By sweeping the transducer through 360° of rotation, as described above, a circumferential lesion can be formed while using less power than would be required with a planar or tubular transducer.

It is to be further understood that the various modes of the ultrasound-balloon devices just illustrated by reference to FIGS. 10B–O may be used according to several different particular methods such as those methods otherwise set forth throughout this disclosure. For example, any of the ultrasound transducer devices may be used to form a conduction block in order to prevent or treat focal arrhythmia arising from a specific pulmonary vein, or may alternatively or additionally be used for joining adjacent linear lesions in a less-invasive "maz"-type procedure.

Figure 11A:
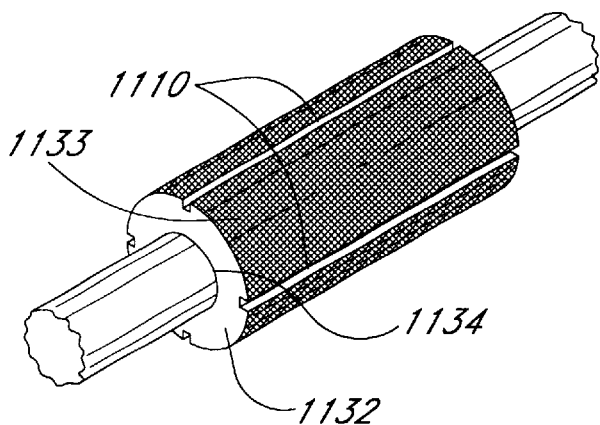
FIG. 11A is a perspective view showing the construction of a circular array of ultrasonic transducers having a common inner electrode.

FIG. 11A is a perspective view showing construction of a circular array of ultrasonic transducers having the inner electrode 1134 as a common electrode and the cylindrical piezoelectric material 1132 as a common element. The single outer electrode 1133, however, is separated by four longitudinal grooves 1110 into four electrodes disposed about the outer surface of the piezoelectric material 1132. The four electrodes correspond to the array of four sensors, each electrode corresponding to one sensor.

Figure 11B:
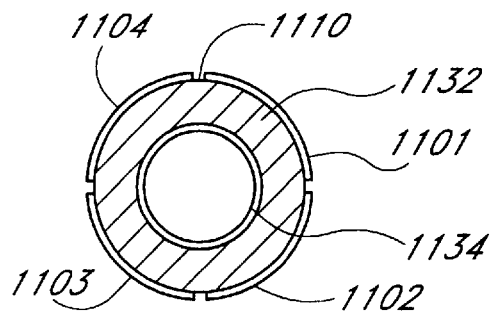
FIG. 11B is a cross-sectional view of the circular array of the ultrasonic transducers of FIG. 11A.

FIG. 11B is a cross-sectional drawing showing construction of a circular array of ultrasonic transducers having the inner electrode 1134 as a common electrode and the cylindrical piezoelectric material 1132 as a common element. The single outer electrode 1133, however, is separated by four longitudinal grooves into four electrodes 1101–1104 disposed about the outer surface of the piezoelectric material 1132. The four electrodes 1101–1104 correspond to the array of four sensors, each electrode corresponding to one sensor.

When an AC voltage is impressed between the inner electrode 1134 and a selected one of the four electrodes 1101–1104, the piezoelectric material vibrates in the region between the inner electrode 1134 and the selected electrode. For example, an AC voltage impressed between the inner electrode 1134 and the electrode 1101 will cause the region between the electrode 1134 and the electrode 1101 to vibrate. However, the piezoelectric material 1132 is a single piece of material as shown in FIG. 11B, so a vibration between the inner electrode 1134 and the electrode 1101 will also cause some vibration in the regions between the electrode 1134 and the electrodes 1104 and 1102. The vibration in the regions between the electrode 1134 and the electrodes 1104 and 1102 will generate a voltage between the electrode 1134 and the electrodes 1104 and 1102. Thus, the sensors produced by the electrodes 1101–1104 are not completely independent of one another and there will be some coupling between the sensors.

Figure 11C:
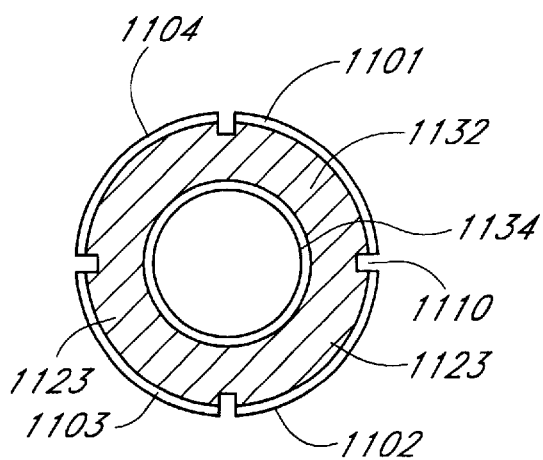
FIG. 11C is a cross-section drawing showing the construction of a circular array of ultrasonic transducers having a common inner electrode and a grooved piezoelectric element.

The coupling between the sensors produced by the electrodes 1101–1104 can be reduced by extending the longitudinal grooves between the electrodes into the single piece of piezoelectric material 1132 to provide a zoned piezoelectric material 1123, as shown in FIG. 11C. The grooves in the piezoelectric material 1123 will tend to physically separate the piezoelectric material 1132 into four zones 1123. Each zone will have less mass than the single piece of piezoelectric material 1132, and thus each of the four zones will typically provide a faster right-down time than the single piezoelectric material 1132.

Figure 11D:
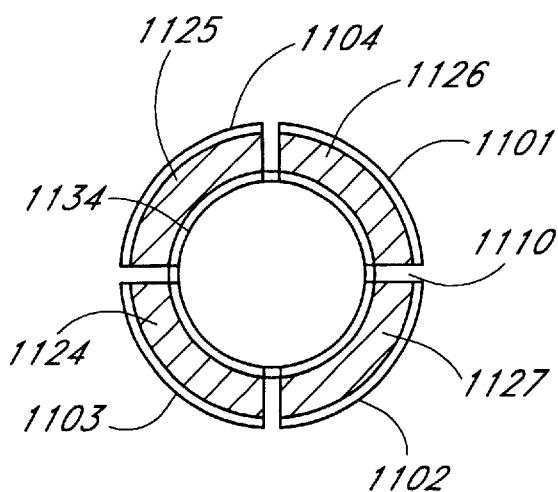
FIG. 11D is a cross-section drawing showing the construction of a circular array of ultrasonic transducers having independent inner and outer electrodes.

The coupling between the sensors produced by the electrodes 1101–1104 can be further reduced by extending the longitudinal grooves all the way through the piezoelectric material 1132 as shown in FIG. 11D, thereby producing four separate pieces of piezoelectric material 1124–1127.

The electrodes 1101–1104 shown in FIGS. 11B–D can be driven separately thereby providing four separate transducers. The electrodes 1101–1104 can also be driven in unison to provide a single transducer similar to the transducer shown in FIG. 10A.

Figure 12:
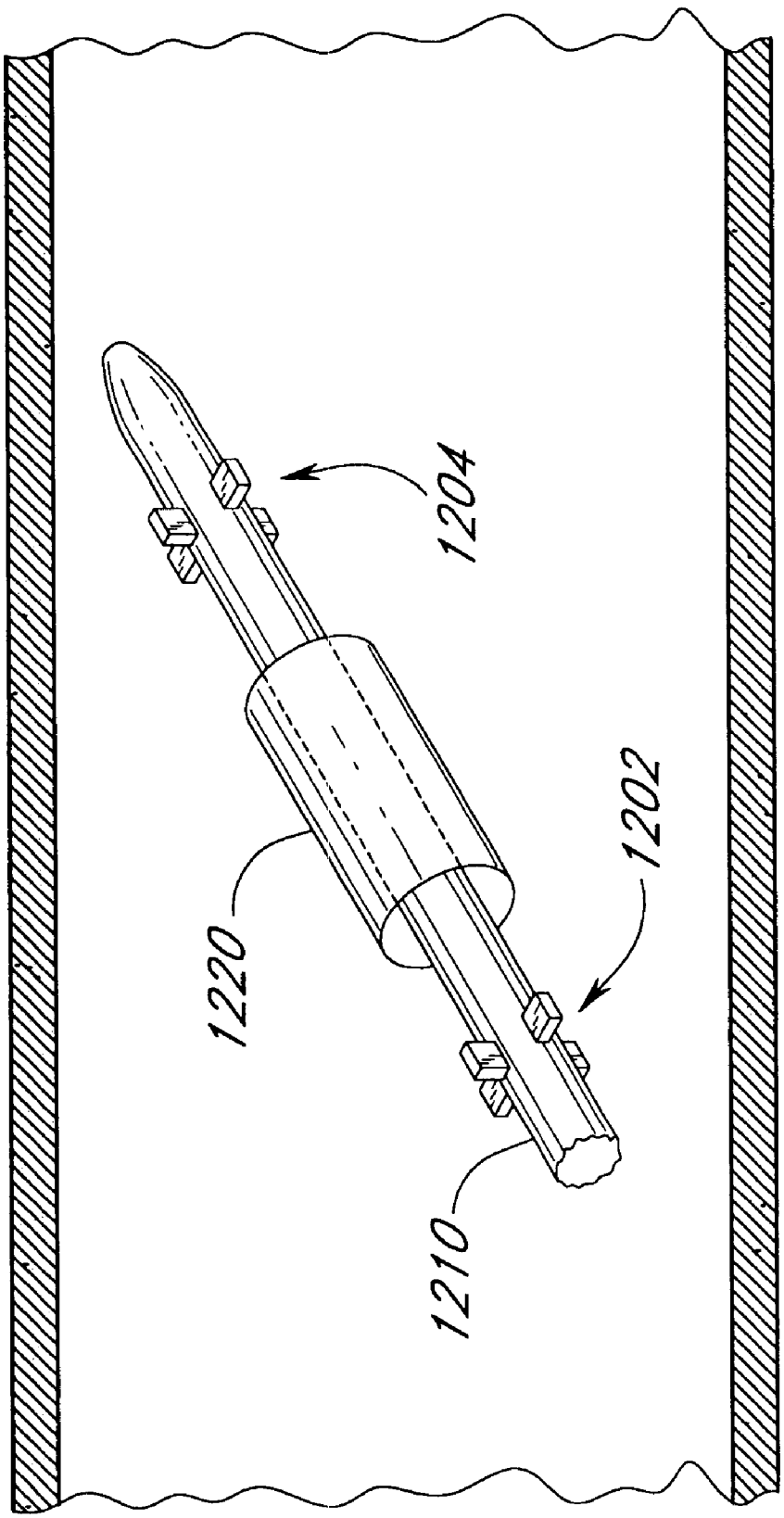
FIG. 12 shows a skew-sensing catheter positioned in a body lumen (e.g., an ostium) in a skewed orientation.

As discussed above, a single ultrasonic sensor is sufficient to determine when the ablation element has entered the ostium. An array of sensors can be used to determine that that the catheter is off-center in the ostium. By extension, FIG. 12 shows a skew-sensing system that uses two arrays of sensors, a proximal array 1202 and a distal array 1204, that can be used to determine that the longitudinal centerline of the catheter 1210 angled ("skewed") with respect to the longitudinal centerline of the vein. Skew is detected by sensing that the array 1202 is off-center in a first direction when the array 1204 is off-center in a second direction. In the illustrated variation, the ultrasonic transducer 1220 that forms the ablation element is shown in between the proximal 1202 and distal 1204 arrays of sensor transducers.

FIG. 13 shows a pair of displays produced by data from a skew-sensing catheter. A proximal display 1302 shows the position of the proximal array 1202. A distal display 1304 that shows the position of the distal array 1204. The catheter 1210 is centered in the vein, with no skew, when both the display 1302 and the display 1304 show that the arrays are centered.

Doppler Monitoring

Figure 14:
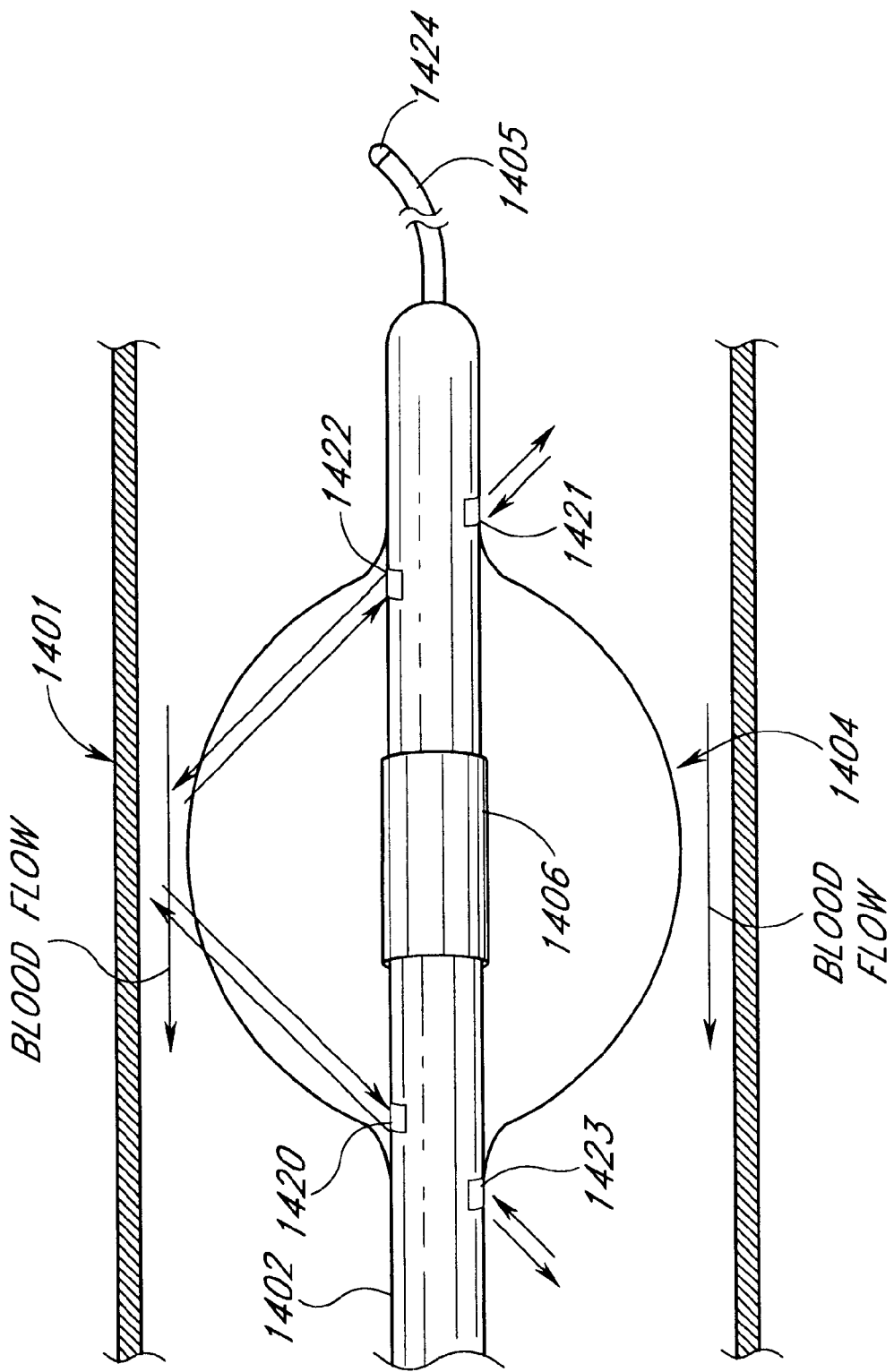
FIG. 14 shows a position-sensing catheter having ultrasonic transducers positioned to provide Doppler measurements of blood velocity in the body lumen (e.g., ostium).

The position of the ablation member (and thus the ablation element) can also be determined by measuring the velocity of the blood flow near an ablation member because blood flows faster in the vein than in the left atrium of the heart. FIG. 14 shows a position-sensing Doppler catheter having ultrasonic transducers positioned near an ablation element 1406 to provide Doppler measurements of blood velocity near the ablation element 1406. The ablation element 1406 is surrounded by a expandable member 1404. The Doppler catheter is shown inside a vein 1401, and the catheter includes a multi-lumen shaft portion 1402. A guidewire 1405 runs through one of the lumens in the shaft 1402 and protrudes from the distal end of the shaft 1402. The expandable member 1404 is located near the distal end of the shaft 1402.

An ultrasonic transducer 1422 is mounted inside the expandable member 1404 and distal to the ablation element 1406. The ultrasonic transducer 1422 is oriented so that it has a field of view that includes a region between the expandable member 1404 and the inner wall of the vein 1401. Another ultrasonic transducer 1420 is mounted inside the expandable member 1404 and a proximal to the ablation element 1406. The ultrasonic transducer 1420 is oriented so that it has a field of view that includes the region between the expandable member 1404 and the wall of the vein 1401. An ultrasonic transducer 1421 is mounted to the catheter shaft 1402 outside the expandable member 1404 and distal to the ablation element 1406. The ultrasonic transducer 1421 is oriented so that it has a field of view that is generally down the channel of the vein 1401 distal to the ultrasonic transducer 1421. An ultrasonic transducer 1423 is mounted to the catheter shaft 1402 outside inside the expandable member 1404 and proximal to the ablation element 1406. The ultrasonic transducer 1423 is oriented so that it has a field of view that is generally along the channel of the vein 1401 proximal to the ultrasonic transducer 1423. An ultrasonic trarnsducer 1424 is mounted on the end of the guidewire 1405. The ultrasonic transducer 1424 is oriented so that it has a field of view that is generally down the channel of the vein 1401 distal to the end of the guidewire 1405.

Each of the ultrasonic sensors 1420–1424 is configured to transmit an ultrasonic sound wave into the blood flowing in the vein 1401. The ultrasonic sensors 1420–1424 are oriented such that the transmitted sound wave will propagate in a vector direction that has a component parallel to the direction of blood flow. A portion of the ultrasonic sound wave will be reflected back to the ultrasonic sensor. The reflections are typically caused by particles and turbulence in the blood flow. The velocity of the blood flow is obtained by comparing a frequency difference between the frequency of the transmitted sound wave and the frequency of the reflected sound wave. A relatively small frequency difference corresponds to lower velocities, and a relatively higher frequency difference corresponds to higher velocities. As stated, the velocity of blood flow is typically higher in the vein 1401 than in the atrium. As the expandable member 1404 expands, the highest velocities are expected to occur in the blood flowing between the expandable member 1404 and the inner wall of the vein 1401 (corresponding to the field of view of the sensors 1422 and 1420). When the expandable member 1404 is fully expanded inside the vein 1401, very little if any blood will flow over the expandable member 1404 and thus the measured velocity will be very close to zero. By contrast, if the expandable member is expanded inside the heart cavity, little or no change will be seen in the velocity of the blood flow.

Thus, as the catheter is inserted into the vein 1401, each of the sensors 1420–1424 will sense an increase in flow velocity. As the expandable member 1404 is expanded the sensors 1420 and 1422 will sense a further increase in flow velocity, followed by a significant decrease in flow velocity when the expandable member 1404 plugs the vein 1401. As the expandable member expands, the sensors 1421, 1423 and 1424 will see a general decrease in flow velocity corresponding to the reduced blood flow. Any one of the sensors 1420–1424 is sufficient to determine the position of the expandable member 1404 and ablation element 1406 in the vein 1401. However, the use of more than one of the sensors 1420–1424 will typically provide greater accuracy.

The pulmonary vein is very distensible, and even with an expandable member 1404 that inflates to well over the "normal" diameter of the vein 1401, the compliance of the vein wall can allow blood flow to pass around the expandable member 1404. It is desirable to minimize this flow as it provides a convective cooling means that competes with the desire to heat the tissue during ablation. The Doppler sensors 1420 and 1422 can advantageously be used indicate that the ablation element 1406 is positioned in the vein ostium, and to check for leakage flow around the expandable member 1404. The Doppler measurements of leakage flow can be used to assist the clinician when adjusting the position of the expandable member 1404 and when adjusting the size of the expandable member 1404 so that there is no appreciable leakage flow around the expandable member 1404.

The A-mode devices discussed in connection with FIGS. 3–13 and the Doppler-mode device discussed in connection with FIG. 14 are not mutually exclusive. A combination of A-mode sensing and Doppler-mode sensing can be advantageously used to provide additional information regarding the position of an ablation element in a pulmonary vein ostium.

Fluid Pressure Monitoring

Fluid pressure at various locations in the patient's body can also be used to establish the position of the ablation catheter, either alone or in combination with the position measurement techniques discussed herein. Pressure measurements can include distal pressure, proximal pressure, and a differential between distal and proximal pressure.

Distal pressure can be monitored either through fluid-filled lumen such as the guidewire lumen or the distal lumen connected to the distal port. The fluid-filled lumen is used as a fluid column to which a pressure transducer is attached. Alternatively, pressure may be monitored by piezoelectric pressure transducers mounted on the catheter shaft distal to the expandable member. In yet another device, a separate pressure-monitoring guide member (e.g., guidewire) may be inserted through a lumen in the catheter shaft to measure the intraluminal blood pressure.

The distal intraluminal blood pressure is relatively higher when the vein is occluded as compared to when the vein is not occluded. A relatively gradual rise in distal pressure is observed as the distal end of the catheter enters pulmonary vein. A relatively sharp increase in distal pressure is observed when the expandable member seats in the pulmonary vein ostium and blocks flow from the pulmonary vein into the atrium. Seating can occur either by inserting the ablation member into the pulmonary vein ostium and expanding the expandable member to engage the wall of the ostium, or by expanding the expandable member in the atrium and then advancing the expanded expandable member into the pulmonary vein ostium in a retrograde fashion. By monitoring pressure as the expandable member is positioned to occlude the vein, it is possible to determine that the expandable member is properly seated in the ostium.

Proximal pressure is typically measured either by using a proximal port lumen attached to a proximal port as a fluid column, by using a piezoelectric pressure transducer mounted on the catheter shaft proximal to the expandable member, or by a pressure-monitoring guide wire inserted through the proximal port lumen. When the expandable member is properly seated in the pulmonary vein ostium, a pressure difference is observed between the distal pressure and the proximal pressure, with the distal pressure being relatively higher than the proximal pressure. This pressure difference will increase relatively gradually as the expandable member enters the ostium and it will increase relatively rapidly as the expandable member seats in the ostium.

X-ray Visualization

A distal port or the guidewire lumen can also be used to introduce radiopaque dies into the blood stream. By using an X-ray system, the clinician can watch the path of the radiopaque die in the bloodstream of the patient. When the expandable member is in the atrium, the radiopaque die will rapidly disperse owing to the relatively large volume of blood and turbulence in the atrium. When the distal port is in the pulmonary vein, the radiopaque die will be seen to flow past the expandable member owing to the relatively uniform flow of blood in the vein. When the expandable member is seated against the pulmonary vein ostium, the radiopaque die will be seen to pool, or stagnate, near the distal port, owing to the cessation of flow in the vein.

Temperature Monitoring

Figure 15:
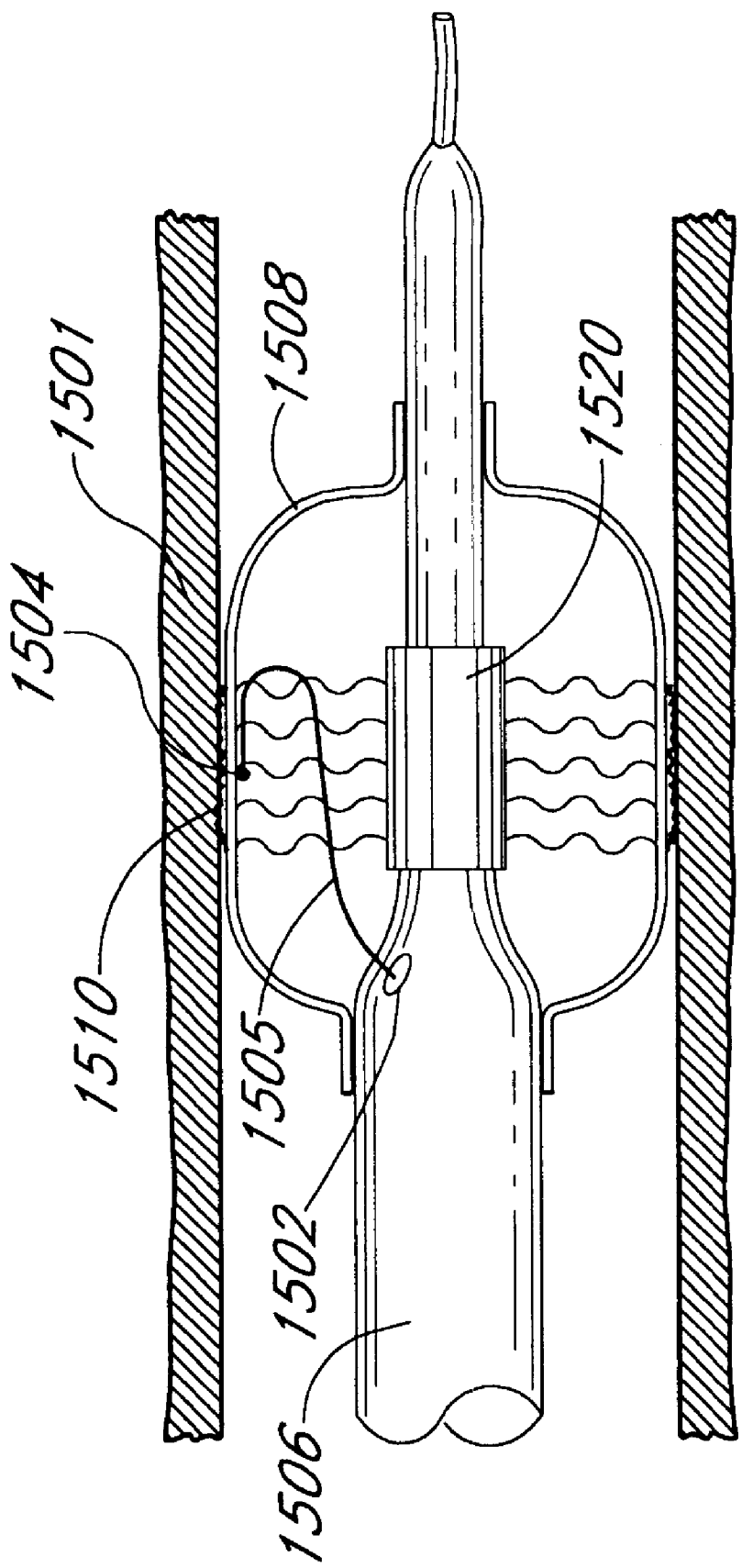
FIG. 15 shows a thermocouple attached to an ablation member to provide temperature feedback for ablation control and position control.

The position of the ablation member can also be determined by temperature measurement. FIG. 15 shows a temperature sensor 1504, such as, for example, a thermocouple, solid-state semiconductor junction, thermistor, optical junction, and the like, attached to the expandable member 1508. The sensor 1504 can be attached to the inside wall of the expandable member 1508, to the outside wall of the expandable member 108, or between layers of the wall of the expandable member 1508. A cable 1505, such as, for example, a wire, optical cable, waveguide, etc, is provided to the sensor 1504. The cable 1505 is routed through a lumen 1502 in the catheter 1506 and back to a proximal sensor element system (not shown).

When the expandable member 1508 is seated against the wall of a vein 1501, the temperature sensor 1504 can measure the temperature of a region of tissue 1510 on the wall of the vein 1501. When the sensor 1504 is not mounted on the outside of the expandable member 1508, temperature corrections can be employed to convert a measured temperature at the sensor 1504 into an actual temperature for the tissue 1510. Such temperature corrections can be used to compensate for the imperfect thermal conductivity of the materials typically used for the expandable member 1508. Although FIG. 15 shows a single sensor 1504, multiple temperature sensors can be used in a similar fashion to monitor more regions of the wall of the vein 1501.

In one device, the sensor 1504 is in the path of the ablation energy produced by the ablation element 1520, and the ablation energy causes a temperature rise (or drop) in the sensor 1504. For example, an RF or ultrasonic ablation element will cause heating of a thermocouple. The temperature reading produced by the sensor 1504 is preferably compensated to remove temperature variations caused by ablation energy coupling into the sensor 1504. In one device, the temperature variations caused by coupling of ablation energy into the sensor 1504 are identified by extracting a relatively slow temperature decay (or rise) due to thermal conduction (with the ablated tissues) from a relatively rapid temperature change due to the ablation energy being turned on or off.

The sensor 1504 can be used to monitor and control the position of the ablation element 1520. The sensor 1504 can also be used to monitor and control the temperature of the tissue 1510 during the ablation process.

When the temperature sensor 1504 (or the portion of the expandable member 1508 near the sensor 1504) is not in contact with the wall of the vein 1501, blood flowing past the sensor 1504 will cool the sensor. Thus, for example, if the ablation element 1520 is activated while the temperature sensor 1504 is in the atrium, blood flowing past the sensor 1504 will carry away the heat produced by the ablation element 1520 and the temperature sensor will detect a relatively small temperature rise. Similarly, if the expandable member 1508 is not properly seated in the ostium to cut off the flow of blood from the vein, blood flowing past the sensor 1504 will again carry away heat produced by the ablation element 1520, and the temperature sensor will only detect a relatively small temperature rise. But, if the expandable member 1508 is properly seated in the ostium, little or no blood will flow past the sensor 1504, the region of tissue 1510 will exhibit a relatively large temperature rise, and the temperature sensor will measure a relatively large temperature rise. Thus, the clinician can position the ablation element by watching for the expected temperature rise, and can determine if the expandable member has properly engaged the target tissue (i.e., determine whether the expandable member is in contact with the target tissue).

The temperature sensor can also be used to assist in the initial positioning of the ablation member (when in an unexpanded state) in the pulmonary vein ostium. In this mode, the ablation element is activated while the ablation member is located in the atrium. As the ablation member is advanced into the pulmonary vein ostium, it has been observed that the sensed temperature decreases. The clinician can use this feedback information to determine when the ablation member is located at the pulmonary vein ostium.

In one device, the ablation element is activated at a medium power, that is, enough power to cause a measurable temperature rise, but not enough power to cause denature the cells of the blood or tissue adjacent to the ablation band of the ablation member. The clinician then advances the catheter 1506 until the sensor 1504 indicates an abrupt temperature rise, indicating hat the expandable member 1508 is properly seated in the ostium. Once the expandable member is properly seated, the ablation element is operated at high power to cause ablation of the tissue region 1510. The sensor 1504 is used to measure the temperature of the region 1510 to control the ablation process and provide sufficient energy to produce the desire ablation without over ablating the tissue region 1510.

FIGS. 16A–L show various modes of operating a circumferential ablation member and various circumferential conduction blocks thereby formed. The present invention contemplates the various combinations of these ablation assemblies and methods with the position monitoring assemblies and related sensor devices, and/or with ablation monitoring assemblies such as temperature monitoring assemblies otherwise herein shown and described, as would be apparent to one of ordinary skill. Therefore, the inclusion of a position monitoring assembly 1650 is variously shown in schematic form throughout FIGS. 16A–L, and furthermore various ablation monitoring sensors and circuits, such as temperature monitoring sensors and circuits, may be coupled to the various ablation members shown where appropriate.

FIG. 16A shows an ablation catheter having on its distal end a circumferential ablation member 1601 with the ablation element that forms an ablative circumferential band 1603 that circumscribes an expandable member 1608 shown to be a balloon. The expandable member 1608 is shown in a radially collapsed position adapted for percutaneous translumenal delivery into the pulmonary vein. However, expandable member 1608 is also adjustable to a radially expanded position when actuated by an expansion actuator, such as, for example, a pressurizeable fluid source, as shown in FIG. 16B, in order to couple circumferential band 1603 to a circumferential region of tissue and thereby form a circumferential conduction block 1654, as shown in FIG. 16C. More specifically, the circumferential band 1603 is schematically shown to be coupled to the ablation actuator 1602 at a proximal end portion of the catheter. After expandable member 1608 is adjusted to the radially expanded position and the band 1603 engages the pulmonary vein wall in the ablation region, the ablation element is actuated by the ablation actuator 1602 such that circumferential band 1603 ablates the surrounding circumferential path of tissue, thereby forming a circumferential lesion that circumscribes the pulmonary vein, as shown in FIG. 16C.

Figure 16E:
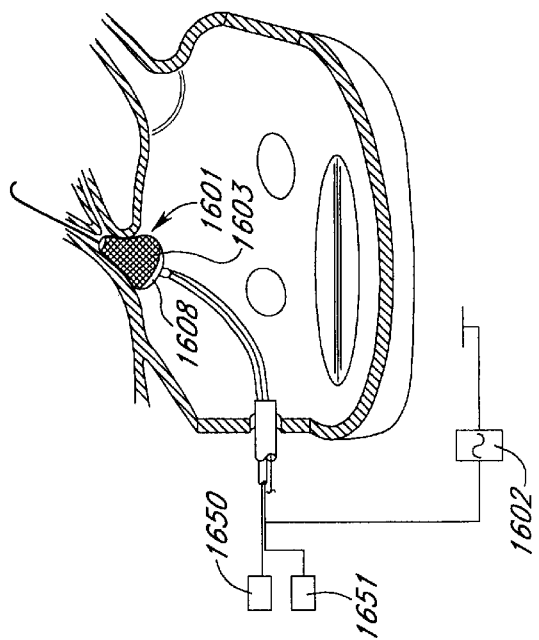
Figure 16G:
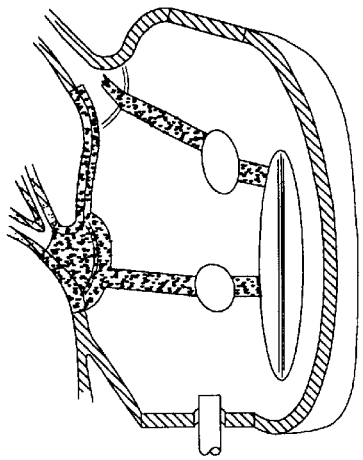
FIG. 16G shows a segmented view of a left atrium and pulmonary veins with a similar circumferential lesion as that shown in FIG. 16F, although further showing the inclusion of such lesion in a pattern with other lesions formed along the posterior left atrial wall in a patient.
Figure 16D:
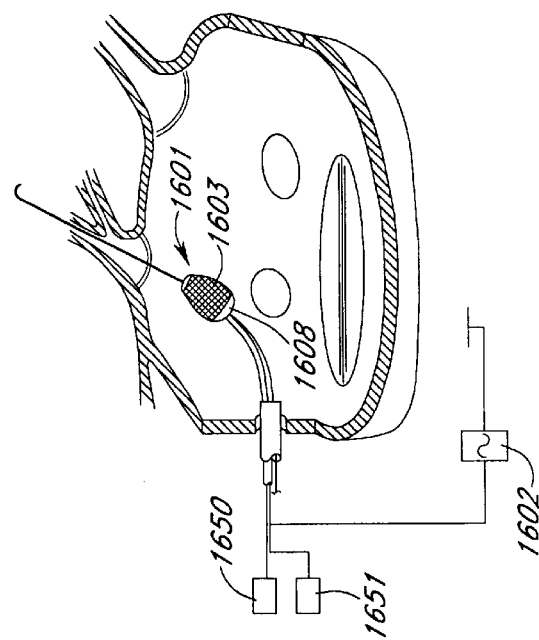
Figure 16F:
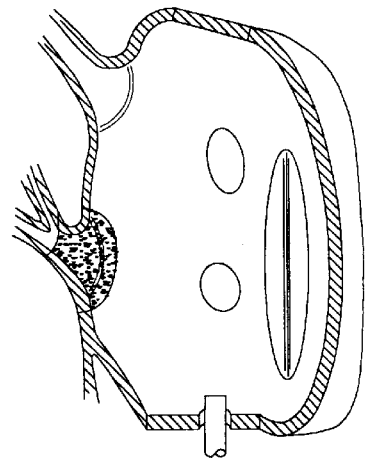
FIG. 16F shows a segmented view of a left atrium and pulmonary veins with one type of circumferential lesion formed during ablation with a circumferential ablation member according to the modes shown in FIGS. 16D–E.

As shown in various other illustrative examples and modes of use throughout FIGS. 16D–I, the desired positioning of the ablation member may be varied, as would be defined by a particular patients anatomy, and the respectively desired ablative coupling of a particular ablation element device via a particular mode for the expandable member of the ablation member. More specifically, the sequential modes of operation for ablation member 1601 shown in FIGS. 16D–E the position sensor of the position monitoring assembly may be coupled to the expandable member. In one mode, the engagement of the expandable member to the tissue surrounding the pulmonary vein ostium is the sensed by the position monitoring sensor, such as when the ablation element is actuated before engagement, as in FIG. 16D, and the sensor senses when the element immediately begins ablating as the assembly is advanced into the vein, such as when the band 1608 couples to the tissue as shown in FIG. 16E. In another mode, by introducing an already inflated balloon into the vein ostium as shown in FIGS. 16D–E, distinctive changes of other parameters, such as blood flow or pressure, may also be accentuated in order to aid the position monitoring according to related sensor devices described above.

Figure 16L:
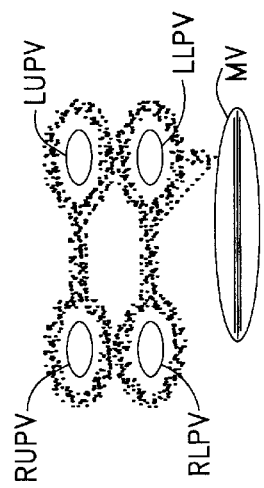
FIG. 16L shows a schematic view of another lesion pattern which may be formed by use of a circumferential ablation member coupled to a position monitoring assembly.
Figure 16I:
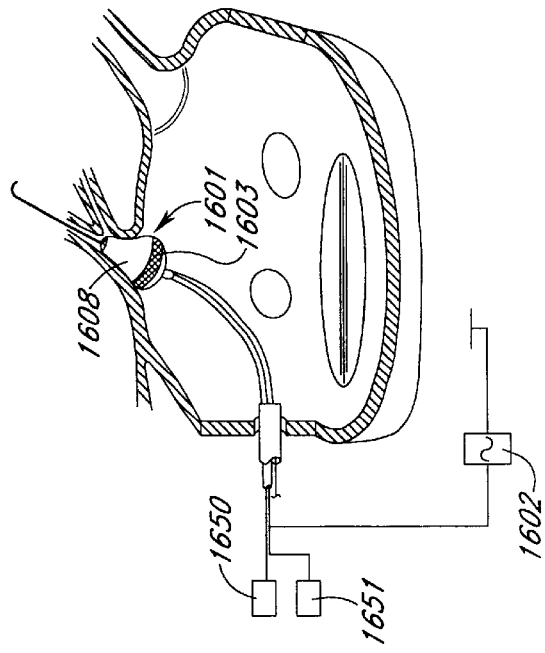
FIG. 16I shows a circumferential ablation catheter with a circumferential ablation member similar to that shown in FIG. 16H after using a position monitoring assembly to position the ablation member at a desired location with the balloon engaged to tissue in a similar manner as shown for the circumferential ablation member in FIG. 16E, except that FIG. 16I shows the circumferential band formed by the ablation element to be coupled to the circumferential region of tissue along the posterior left atrial wall and surrounding the pulmonary vein's ostium.
Figure 16K:
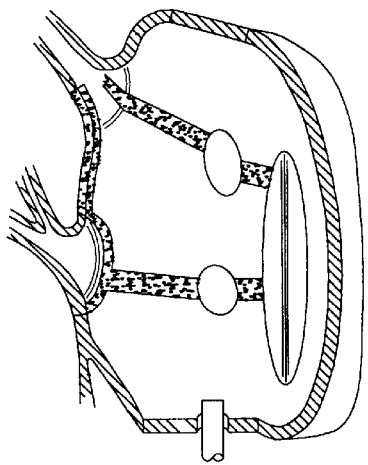
FIG. 16K shows a segmented view of a left atrium and pulmonary veins with a similar circumferential lesion as that shown in FIG. 16F, although further showing the circumferential lesion in combination with other lesions formed along the posterior left atrial wall in a patient in order to form one type of lesion pattern for preventing atrial arrhythmia.
Figure 16H:
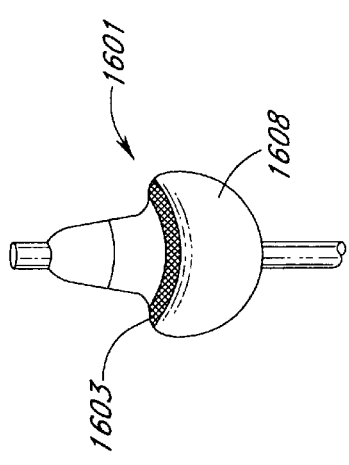
FIG. 16H shows another circumferential ablation member for use with the position monitoring assembly, and includes a pear-shaped expandable balloon with a contoured outer surface and an ablation element forming a circumferential band along a distal facing taper of the contoured outer surface.
Figure 16J:
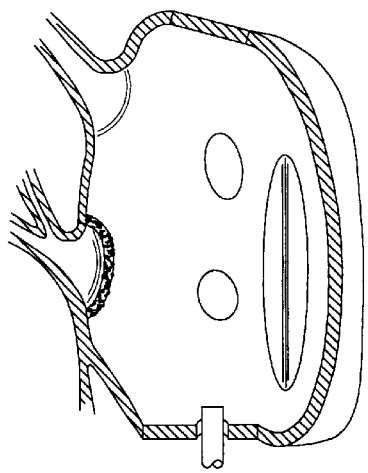
FIG. 16J shows one type of circumferential lesion formed according to the mode shown in FIG. 16I.

Moreover, as shown in FIGS. 16D and 16L, the desired location for the ablation member may be at least in part outside of the pulmonary vein (and in some circumstances as shown partially within the vein and partially outside), such that the ablation element is coupled to a circumferential region of tissue along the posterior left atrial wall and surrounding the ostium. Further to this particular circumstance, the ablative coupling may include both tissue outside and inside of the pulmonary vein (FIGS. 16D–G), or only tissue outside of the vein and along the atrial wall (FIGS. 16H–L). Still further, as shown variously in FIGS. 16F–G and 16K–L, such circumferential lesions as variously described may be formed in conjunction with other lesions to form particular patterns of connected lesions in order to isolate arrhythmogenic foci from other parts of the atrium.

Various forms of ablation elements may be suitable for use in an overall ablation assembly as contemplated within the present invention.

In one example, the band 1603 includes one or more conductive electrodes. In one device, the band 1603 includes a porous skin that is adapted to allow fluid, such as hypertonic saline solution, to pass from an internal chamber defined by the catheter and outwardly to contact the tissues of the ostium. Such a porous skin can be constructed according to several different methods, such as by forming holes in an otherwise contiguous polymeric material, including mechanically drilling or using laser energy, or the porous skin may simply be an inherently porous construction, such as a porous fluoropolymer, e.g. polytetrafluoroethylene (PTFE), cellulose, polyurethane, or other porous material, blend, or construction. In any case, by electrically coupling the fluid within the porous balloon skin to an RF current source (preferably monopolar), the porous band serves as an electrode wherein RF current flows outwardly through the pores via the conductive fluid. In addition, it is further contemplated that a porous outer skin may be provided externally of another, separate expandable member, such as a separate expandable balloon, wherein the conductive fluid is contained in a region between the porous outer skin and the expandable member contained therein. Various other "fluid electrode" designs than those specifically herein described may also be suitable according to one of ordinary skill upon review of this disclosure.

In the alternative, or in addition to the RF electrode variations just described, the circumferential ablation element may also include other ablative energy sources or sinks, and particularly may include a thermal conductor that circumscribes the outer circumference of the working length of an expandable member. Examples of suitable thermal conductor arrangements include a metallic element, which can, for example, be constructed as previously described for the more detailed RF devices above. In one device, the thermal conductor, such a metallic element, can be generally either resistively heated in a closed loop circuit internal to the catheter, or conductively heated by a heat source coupled to the thermal conductor. In the latter case of conductive heating of the thermal conductor with a heat source, the expandable member may be for example a polymeric balloon skin which is inflated with a fluid that is heated either by a resistive coil or by bipolar RF current. In any case, it is believed that a thermal conductor on the outer surface of the expandable member is suitable when it is adapted to heat tissue adjacent thereto to a temperature between 40° and 80° C.

Figure 17B:
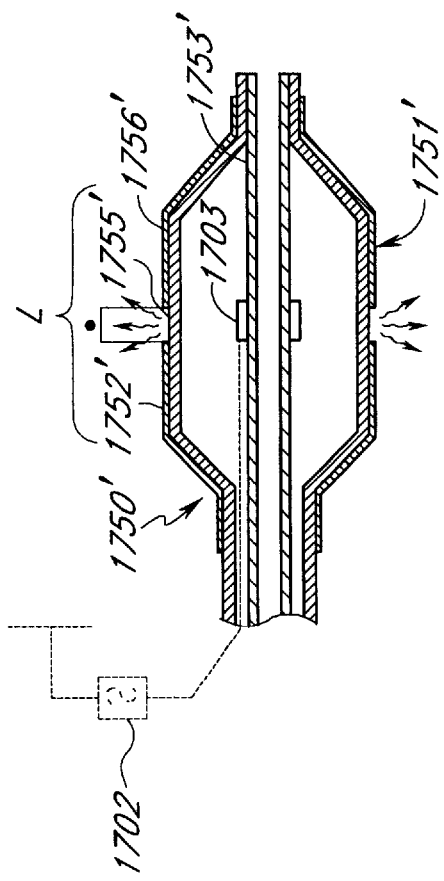
FIG. 17B shows a circumferential ablation member for use with a position monitoring assembly and which includes proximal and distal insulators over the working length of a balloon such that a narrow, circumferential band circumscribing the working length is left uninsulated to thereby isolate the ablatively coupling between an ablation source within the balloon and a circumferential region of tissue engaged to the narrow uninsulated band.
Figure 17A:
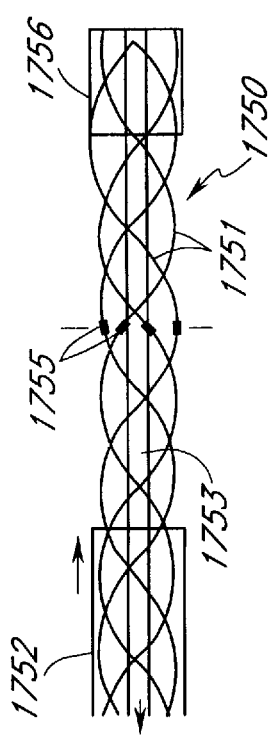
FIG. 17A shows a circumferential ablation member that includes an expandable cage with a pattern of electrodes and that is adapted for use with a position monitoring assembly in order to ablate a circumferential region of tissue such as according to the modes of use and in order to produce the circumferential conduction blocks variously shown throughout FIGS. 16A–L.

In a further variation, another ablation catheter for use with a position monitoring assembly includes an expandable member comprising a cage structure 1750 as shown in FIG. 17. The cage 1750 includes a mesh of wires 1751 and is expandable to engage a desired ablation region in a pulmonary vein.

The radial expansion of the cage 1750 is accomplished as follows. A sheath 1752 is secured proximally around the wires 1751. A core 1753, which may be a metallic mandrel such as stainless steel, extends through the sheath 1752 and distally within the cage 1750 wherein it terminates in a distal tip 1756. The wires 1751 are secured to the distal tip 1756, by, for example, soldering, welding, adhesive bonding, heat shrinking a polymeric member over the wires, or any combination of these methods. The core 1753 is slideable within the sheath 1752, and may for example be housed within a tubular lumen (not shown) within the sheath 1752. By moving the sheath 1752 relative to the core 1753 and the distal tip 1756 (shown by arrows in FIG. 17), the cage 1750 is collapsible along its longitudinal axis in order to force an outward radial bias (also shown with arrows in FIG. 17) to the wires 1751 in an organized fashion to formed a working length of the cage 1750, which is expanded (not shown).

A plurality of ablation electrodes 1755 are attached to the cage 1750. Each electrode is positioned on one of the wires 1751 and each electrode is similarly located along the longitudinal axis of the cage 1750. The radial bias given to the wires 1751 during expansion, together with the location of the ablation electrodes 1755, serves to position the plurality of ablation electrodes 1755 along a circumferential, equatorial band along the expanded working length of cage 1750.

The wires 1751 are preferably electrically conductive, and are typically made from an elastic metal alloy, such as, for example, stainless steel, nickel-titanium, or a combination of both. In one device, separate electrical conductors are used in order to actuate the ablation electrodes 1755 to efficiently emit ablative current into surrounding tissues. The wires 1751 themselves can also serve as electrical conductors for ablation electrodes 1755. The wires 1751 can be coated with an electrical insulator to isolate the electrical flow into surrounding tissues to the site of the ablation electrodes 1755. Moreover, the ablation electrodes 1755 can be formed by removing electrical insulation to expose a selected region on the wires 1751 to allow for current to flow into tissue only from the exposed region.

For the purpose of further illustration, FIG. 17B further shows another suitable circumferential ablation member 1750' that includes an inflatable balloon 1751' for the expandable member. Circumferential ablation member 1750' further includes shields or insulators 1752', 1756' which isolate an ablative coupling from an ablation source within the balloon to circumferential band 1755' that is formed along an uninsulated portion of the balloon between insulators 1752', 1756'. Further to this assembly, ablation actuator 1702 is coupled to and actuates ablation source 1703 that thereby ablative couples through the inflation medium and through the balloon 1751' to tissue engaged to circumferential band 1755'. The ablative coupling may take many forms as herein described for the various types of ablation elements. For example, the band 1755' may include a porous skin such as described above, wherein fluid within the balloon 1751' ablative couples through the skin, such as a chemical ablation means or an electrical ablation means (shown in schematically in shadow by electrical current source 1702 coupled to ablation source 1703 that may be, for example, an electrode). The insulators according to this variation do not allow such coupling along the insulated regions of the balloon. Furthermore, the coupling may be thermal, such as by heating or hypothermically cooling tissue engaged to the band 1755'. Furthermore, the insulators may be ultrasonic or light shields, wherein the ablation source 1751 may be an ultrasonic or light emitting ablation element.

Still further, other ablation members and related ablation elements may be used with a position monitoring assembly or with an ablation monitoring assembly as herein described without departing from the scope of the invention. For example, various shaped ablation members such as looped members that are adapted to ablate a circumferential region of tissue may be appropriate substitutes for inclusion in the overall assemblies herein described.

Thermocouple-Electrode Attachment

As noted above, the catheter assembly can include one or more temperature sensors (e.g., thermocouples) to (1) determine the position of the ablation member and/or (2) monitor tissue ablation. Thus, such temperature sensors can be used in conjunction with all of the position monitoring systems described above.

The catheter assembly can also include one or more electrodes arranged to make contact with venous and/or cardiac tissue adjacent the targeted region of tissue. Such electrodes desirably are arranged for electrical mapping purposes as well as to check the integrity of the conductive block after ablation of the region of tissue. For instance, in one mode, an electrode is mounted distal of the ablation element and is used to invoke an arrythemogenic condition in venous/cardiac tissue distal of the formed lesion. This electrode can be used by itself or in combination with one or more electrodes that are positioned proximally of this distal-most electrode.

One or more of these proximal electrodes can be used to map the responsive electro-physiological response to determine whether the response transcends the formed lesion (i.e., the produced conductive block). In one variation, the catheter assembly includes only one distal electrode and a proximal electrode positioned on opposite sides of the ablation element. In another variation, the catheter assembly includes an array of electrodes positioned along a length of the catheter. When the expandable member lies in a collapsed position, the distal portion of the delivery member can be manipulated to position the array of electrodes against the tissue and across the formed lesion. In this manner, the integrity of the formed conduction block being formed can be monitored and checked.

Both temperature sensors and electrodes desirably are arranged along at least a portion of the length of the expandable member (e.g., the inflatable balloon). The following provides a description of several ways to attach such sensors and electrodes to or use such sensors and electrodes with an expandable member.

The temperature sensor devices herein shown and described are believed to be particularly well suited for use with highly elastomeric balloons, wherein such designs are at least in part intended to account for and accommodate high amounts of elongation at the balloon/sensor interface. More particular examples of such highly compliant or elastomeric balloons are described elsewhere in this disclosure.

Notwithstanding the highly beneficial aspects of such assemblies, the embodiments may also be combined with other non-compliant balloon varieties, or may be further coupled to other ablation members not incorporating balloons, such as for example those using expandable cages, wherein the outer perimeter of such cage may be interchangeably substituted with the balloon skin in the devices shown. In other more isolated instances, the temperature monitoring sensor assemblies herein disclosed may be combined with certain circumferential ablation members without reliance on any particular circumferential ablation member design, such as in the event of deployable thermocouple splines that may be positioned in a circumferential pattern in order to monitor ablation in a manner that is relatively independent of the ablation member features (see, for example, FIGS. 28A–F).

In one device, one or more thermocouples or electrodes are disposed near a distal end of a catheter. FIGS. 18A–B show a catheter having a catheter shaft 1801 and an expandable member, such as a balloon 1802 shown in the figure, near the distal end of the shaft 1801. In FIG. 18A the balloon 1802 is collapsed, and in FIG. 18B the balloon 1802 is expanded. The catheter optionally includes an ablation element, such as an ultrasonic ablation element 1803, which may be inside or near the balloon 1802. A thermocouple wire 1804 runs through a lumen in the shaft 1801 and exits the shaft inside the balloon. A thermocouple 1806 on the thermocouple wire 1804 is attached to the balloon 1802.

Figure 18D:
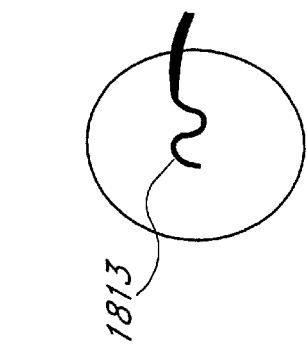
FIG. 18D is a plan and cross-sectional view of another thermocouple configuration and technique for attachment.
Figure 18E:
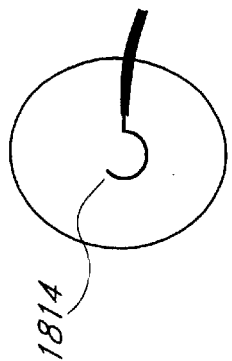
FIG. 18E is a plan view of a thermocouple configured as an oval loop.
Figure 18G:
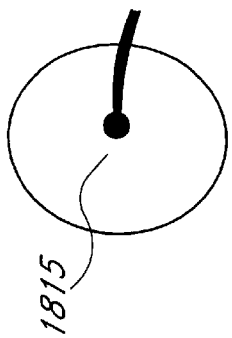
FIG. 18G is a plan view of a thermocouple configured in a serpentine or "S" shape.
Figure 18H:
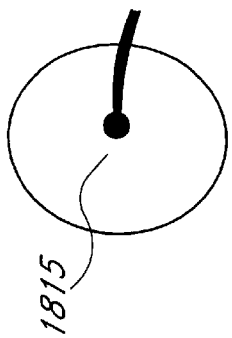
FIG. 18H is a plan view of a thermocouple configured as a hook shape.
Figure 18I:
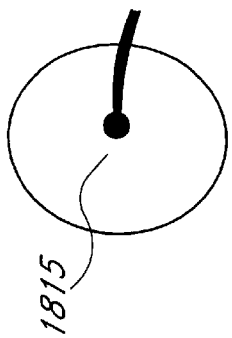
FIG. 18I is a plan view of a thermocouple configured as a spherical ball.
Figure 18A:
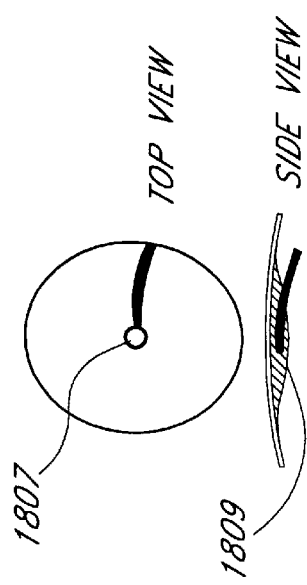
FIG. 18A shows an ablation catheter having an expandable member (such as a balloon) in a collapsed position and a thermocouple attached to an inside wall of the expandable member.
Figure 18F:
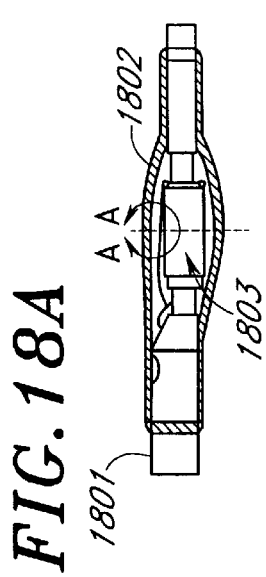
FIG. 18F is a plan view of a thermocouple configured as a "T" shape.
Figure 18B:
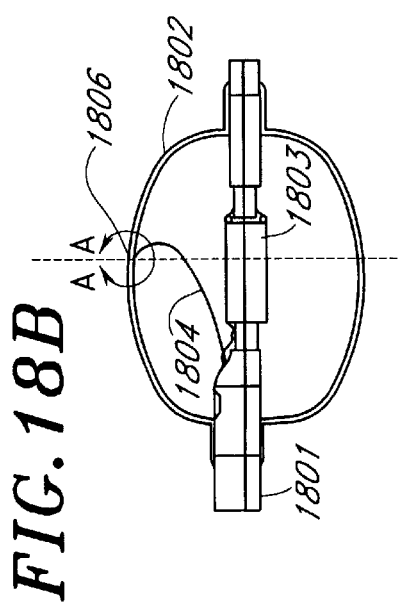
FIG. 18B shows the ablation catheter of FIG. 18B where the expandable member is in an expanded position.

Suitable shapes for the thermocouple 1806 include, but are not limited to, a loop 1807 as shown in the plan view of FIG. 18D, an oval loop 1811 as shown in the plan view of FIG. 18E, a "T" configuration 1812 as shown in the plan view of FIG. 18F, an "S" configuration 1813 as shown in the plan view of FIG. 18G, a hook configuration 1814 as shown in the plan view of FIG. 18H or a spherical ball configuration 1815 as shown in the plan view of FIG. 18I. Such shapes are desirable both for anchoring the thermocouple to the balloon and for sensing the temperature of tissue outside the balloon. That is, in each of the above shapes a portion of the thermocouple lies generally normal to, or at least skewed relative to, the axis of the thermocouple wire to enhance the coupling between the thermocouple and the adhesive that bonds it to the balloon wall, as described below. These shapes also provide more surface area for the thermocouple without lengthening the thermocouple. These thermocouples, with more exposed area than a straight thermocouple, are believed to have better accuracy and response time.

Figure 18C:
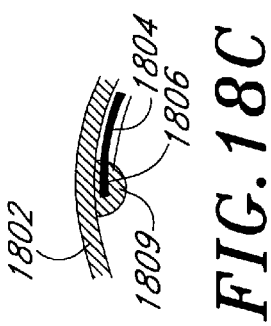
FIG. 18C is an enlarged view of the area A—A noted in FIGS. 18A–B which illustrates one technique for attaching the thermocouple to the inside wall of the expandable member.

The thermocouple 1806 is attached to an inside wall of the balloon 1802 as shown in FIG. 18C by a fastener 1809. In one variation, the fastener 1809 is a bead of adhesive that is compatible with the material used for manufacturing the balloon 1802. Suitable adhesives include, but are not limited to, epoxies, cyanoacetate adhesives, silicone adhesives, flexible adhesives, etc. In alternate embodiments, the fastener 1809 is a tape that is bonded to the balloon, a bead of material that is molded or heat-bonded to the balloon.

The thermocouple wire 1804 preferably has sufficient flexibility so that it does not seriously impede the expansion of the balloon 1802. Additionally, according to one highly beneficial aspect of the embodiment shown in FIGS. 18A–B, the thermocouple wire 1804 is provided with a looped or single-turn spring shape so that the wire expands with the balloon 1802, and again does not seriously impede the expansion of the balloon 1802, as well as not pull on the embedded thermocouple when the balloon 1802 is expanded.

In FIG. 18C, even though the fastener 1809 can be constructed using a flexible material, the fastener 1809 is shown as providing a relatively non-adjustable or fixed attachment point between the thermocouple 1806 (or the thermocouple wire 1804) and the balloon 1802.

Figure 18J:
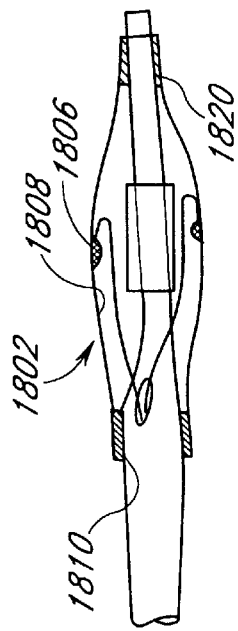
FIG. 18J shows a partially sectioned perspective view of the distal end portion of a circumferential ablation catheter during one mode of assembling a thermocouple to the inner surface of a balloon in an assembly similar to that shown in FIGS. 18A–B.
Figure 18K:
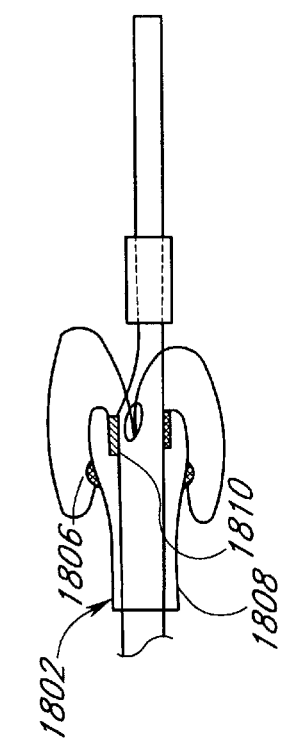
FIG. 18K shows a perspective view of a further sequential mode of assembling the assembly shown in FIG. 18J.

Attachment of the thermocouple to the interior wall of the balloon 1802 may be completed according to many modes, one of which, is provided herein for the purpose of illustration in FIGS. 18J–K. More specifically shown in FIG. 18J, the proximal end of the balloon 1802 is secured onto the catheter shaft at proximal adaption 1810 and is then everted over onto the shaft to expose inner balloon surface 1808. The thermocouple 1806 is secured to inner surface 1808 in the orientation shown in FIG. 18J and by use of adhesive as elsewhere described herein. Other additional thermocouples can be secured in this manner as also shown and described in more detail in FIG. 36 below. The balloon is then rolled back into its original non-everted orientation where distal adaption 1820 is made to the shaft, securing the thermocouple within the interior chamber of balloon 1802, as shown in FIG. 18K.

Figure 19A:
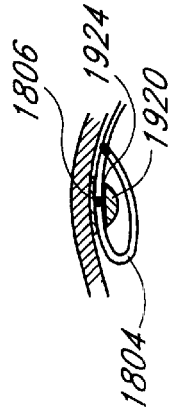
FIGS. 19A–D show various sectional perspective and enlarged cross-sectioned views of the area within circle B—B of FIGS. 19A–B of an ablation catheter having an expandable member and a thermocouple attached to the expandable member by a looped coupling between the thermocouple member and a relatively flexible adhesive attachment.
Figure 19B:
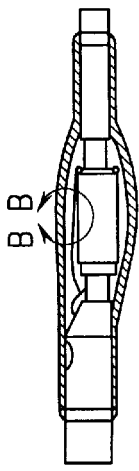
Figure 19C:
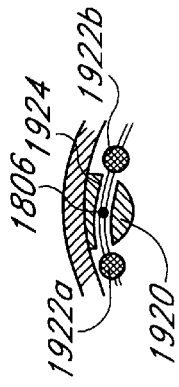
Figure 19D:
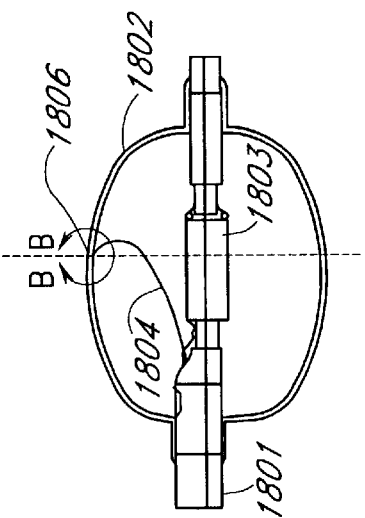

FIGS. 19A–D show another embodiment wherein an attachment 1920 attaches the thermocouple 1806, or the thermocouple wire 1804, to the balloon 1802. The attachment 1920 is adjustable and provides a relatively flexible attachment. In the embodiment illustrated in FIGS. 19C–D, the attachment 1920 is a bead of adhesive that includes a channel or tube 1924. The thermocouple wire 1804 is slideably disposed in the tube so that as the balloon 1802 expands, the thermocouple wire 1804 can move somewhat with respect to the balloon 1802. In one embodiment, the thermocouple wire 1804 is held in the tube 1924 by one or more beads 1922a,b of material attached to the thermocouple wire 1804, as shown in FIG. 19D. The thermocouple wire 1804 can also be held in the tube by a loop or bend in the thermocouple wire as shown in FIG. 19C.

For clarity, the figures show a single thermocouple. Nonetheless, a plurality of thermocouples can also be attached to the balloon 1802 using the techniques shown in FIGS. 18A–I and 19A–D. One beneficial construction for such thermocouples uses "T"-type thermocouple wire which is commercially available from "Hudson International" and is constructed of copper and Constantine, and more particularly a 44 gauge bifilar configuration has been observed to be suitable.

In brief, such thermocouple wires may be cut to the desired length and then soldered where the temperature monitoring is to be made—such solder removes insulation between the individual strands of the bifilar and electrically couples the leads in a manner that is sensitive to changes in temperature. Notwithstanding the benefits provided by such thermocouples in the present embodiments, other well-known temperature sensors may be suitable substitutes for the thermocouples described herein without departing from the scope of the invention.

Figure 20:
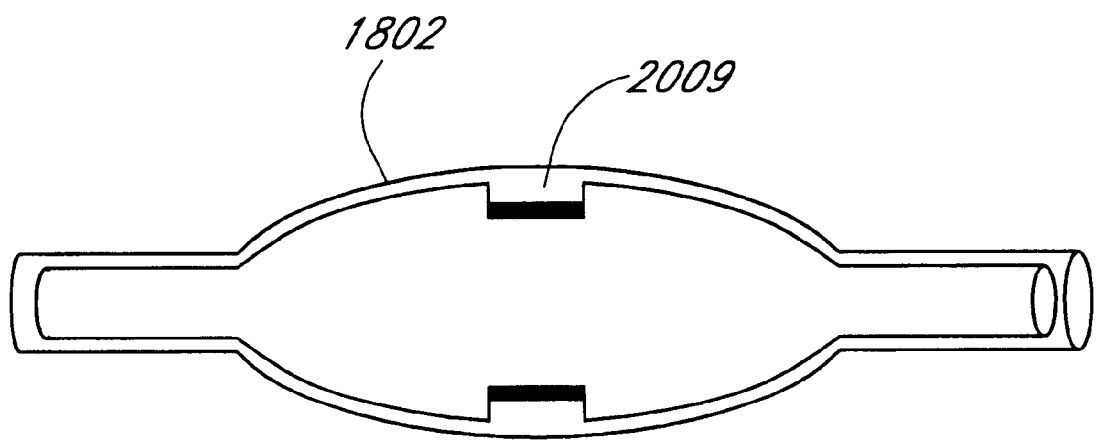
FIG. 20 shows a reinforcement area wherein the inner wall of a balloon is thickened near a stress point, such as a point where a thermocouple, electrode, or other element is attached to the balloon, the reinforcement is configured to strengthen the balloon at the stress point while still maintaining a relatively smooth outer surface of the balloon.
Figure 21:
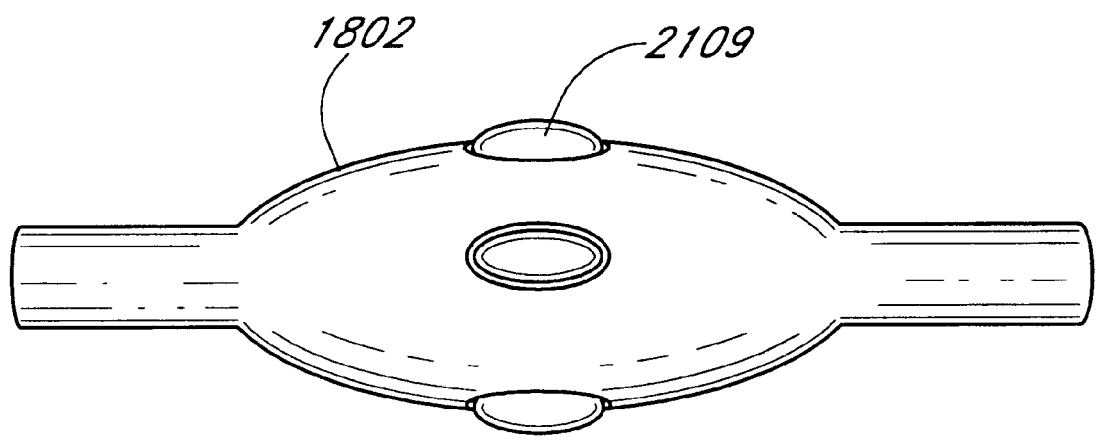
FIG. 21 shows a reinforcement area wherein the reinforcement includes thickening the outer wall of the balloon.

The attachment points are typically located in high-stress areas. In one embodiment, the wall of the balloon 1802 may be reinforced near attachment points, such as is shown in FIGS. 20–21. More specifically, FIG. 20 shows a reinforcement 2009 wherein the wall surface of the balloon 1802 is thickened on an inner side near the attachment point. Thickening the inner surface wall provides increased strength while still maintaining a smooth outer surface of the balloon 1802, thus allowing the balloon to be easily manipulated inside the body of the patient.

FIG. 21 shows a reinforcement 2109 wherein the reinforcement includes thickening the wall of the balloon 1802 on an outer side. The thickened areas of the outer wall surface of the balloon may be smoothed such that the balloon still provides a relatively smooth outer contour. In either event, such variable wall thickness may be created by use of molding of the balloon material, either as a thermoset or thermoplastic material process, or by varying the operating parameters or mandrel dimensions when the balloon is formed by a dip coating process, or otherwise by post processing a pre-extruded generally uniform tubing (e.g. shrinking, stretching, laminating the tubing as appropriate to achieve the desired dimensions and geometry).

Figure 22A:
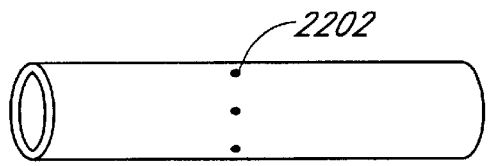
FIGS. 22A, 22B and 22C shows side view, a longitudinal cross-sectional view, and an enlarged cross-sectional view, respectively, of a thermocouple (or an electrode) protruded through an aperture in the wall of a balloon such that the thermocouple is disposed on the outside of the balloon.
Figure 22B:
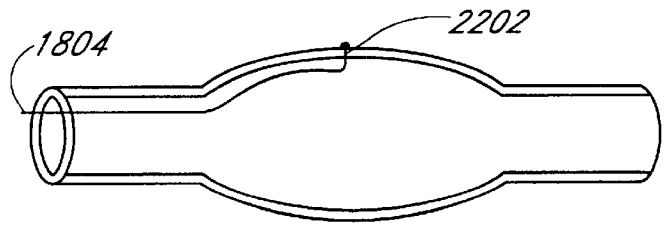
Figure 22C:
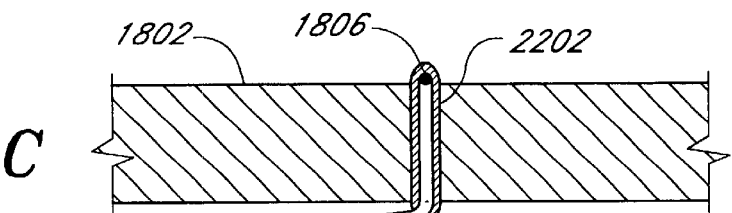

In a further thermocouple/balloon variation, shown in FIGS. 22A–C, the thermocouple wire 1804 protrudes through an aperture or hole 2202 in the wall of the balloon 1802 such that the thermocouple 1806 (or an electrode) is disposed on the outside of the balloon 1802. The thermocouple 1806 is held in place by a bead of adhesive 2204 compatible with the balloon 1802, such as, for example, a flexible adhesive, an elastomeric adhesive, a silicone adhesive, etc. Placing the thermocouple 1806 on the outside of the balloon 1802 typically provides enhanced thermal contact between the thermocouple 1806 and the pulmonary vein. The mounting shown in FIGS. 22A–C can also be used to place an electrode in contact with the pulmonary vein by replacing the thermocouple with an electrode and leaving the electrode electrically conductive to tissue adjacent thereto (or merely using the thermocouple as an electrode). As noted above, electrodes are useful for stimulating and mapping the electrical properties of tissue, such as along the ablation region or elsewhere for the purpose of monitoring the electrical cardiac signals or otherwise assessing the formation of a conduction block, e.g. where a pulmonary vein extends from an atrial wall.

Figure 23:
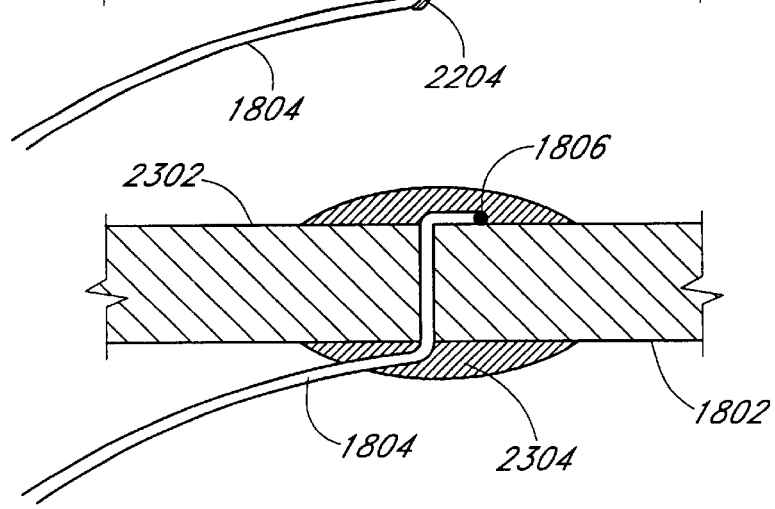
FIG. 23 shows an enlarged cross-sectional view of a thermocouple/balloon interface wherein the thermocouple is shaped to lay along the outside wall of a balloon and secured by a bead of adhesive or other material.
Figure 24:
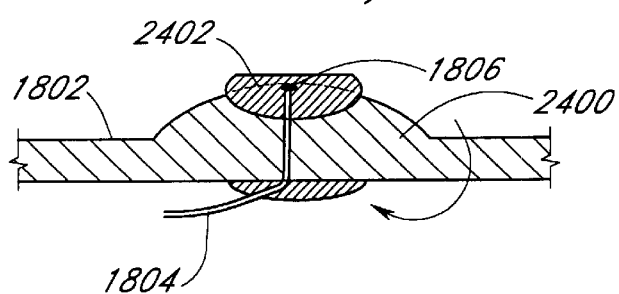
FIG. 24 shows an enlarged view of a bump integrally formed along the outer surface of a balloon wall, and shows a thermocouple seated outwardly through a channel extending through the bump, and further shows the thermocouple potted with adhesive in a depression on the outside aspect of the bump.

FIG. 23 shows an additional embodiment wherein the thermocouple 1806 is laid along an outside wall 2302 of the balloon 1802 and secured by a bead of adhesive 2304 or other material. FIG. 24 shows yet another embodiment, wherein a bump 2400 is formed into the wall of the balloon 1802 and the thermocouple wire 1804 extends from the inside surface of the balloon, and through the bump 2400, wherein the thermocouple 1806 is seated on the outside surface of the bump or within a recess 2402 on the outside surface of the bump 2400.

Figure 25:
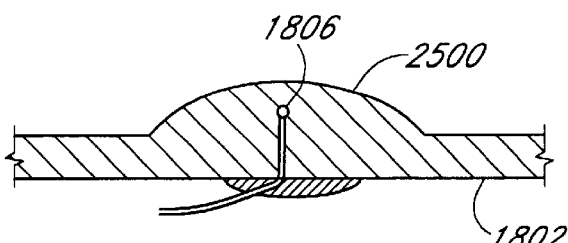
FIG. 25 shows a similar view of a balloon wall, bump, and thermocouple as that shown in FIG. 24, although showing the channel formed only partially through the wall of the balloon such that the thermocouple terminates within the bump and is potted within the channel by use of only an adhesive along the inner surface of the balloon.

FIG. 25 shows another embodiment, wherein a bump 2500 is formed in the wall of the balloon 1802 and the thermocouple 1806 is seated inside the bump 2500 without the need for introducing a hole completely through the wall of the balloon 1802. The bumps 2400 and 2500 shown in FIGS. 24 and 25 provide extra strength to the wall of the balloon 1802 at the stress point caused by the thermocouple 1806. The bumps 2400, 2500 also help to smooth the outside surface of the balloon with an external thermocouple 1806, thus allowing the balloon to slide smoothly through the patient. In the embodiments shown, the bumps 2400 and 2500 are formed integrally with the balloon wall 1802, such as according to the constructions described previously above, though they may be otherwise formed in suitable substitute constructions or methods without departing from the scope of the invention.

FIG. 26A shows an embodiment wherein the thermocouple 1806 is disposed between two layers of a multi-layer balloon 2602. Like the previously disclosed balloons, the balloon 2602 is mounted on a catheter shaft 2610. The balloon 2602 includes a two-layer wall having an outer layer 2620 and an inner layer 2621. The outer layer 2620 is attached to the catheter shaft by an outer seal 2650, and the inner layer 2621 is attached to the catheter shaft by an inner seal 2652. The thermocouple wire exits a lumen 2654 in the catheter shaft via an exit port 2656 located between the inner and outer seals. The thermocouple 1806 is disposed between the outer layer 2620 and the inner layer 2621.

In one embodiment, shown in FIGS. 26B–D, the thermocouple wire 1804 and the thermocouple 1806 are slideably disposed between the inner layer 2621 and the outer layer 2620, such that the thermocouple slides inside the balloon 2602 as the balloon 2602 expands. When the balloon 2602 is collapsed, as shown in FIG. 26B, the thermocouple is in a first position. When the balloon 2602 is expanded, as shown in FIG. 26C, the thermocouple 1806 moves a distance d (see FIG. 26B) to a second position owing to the expansion of the balloon. In the particular variation shown, the thermocouple 1806 and the thermocouple wire 1804 slide in a channel 2624 (FIG. 26D) formed between the inner layer 2621 and the outer layer 2620. The channel 2624 may be filled with a fluid, such as in order to facilitate movement of the thermocouples as described or to prevent air bubbles from being trapped. It may be further desirable to fill channel 2624 with a material having an acoustic property similar to the acoustic properties of the fluid used to fill and expand the balloon 2602.

It is contemplated that the channel embodiment just described by reference to FIGS. 26A–D may be further constructed out of one continuous balloon material, versus between laminate layers. For example, in a dip coating process for forming balloon 2602, the thermocouple and thermocouple member may be laid along the partially formed balloon length and dipped over during completion of the dipping process until it is imbedded within the resultant cured balloon. Furthermore, a separate member such as a relatively lubricious "beading" mandrel, more particularly a beading mandrel constructed from polytetrafluoroethylene (PTFE) may be used during the dip coating process as just described for the thermocouple. According to this variation however, upon completion and cure of the fully dip coated balloon, the beading mandrel is then removed to leave channel 2624. The thermocouple is then inserted within the channel that was formed in a final thermocouple/balloon subassembly. In the event a thermocouple bifilar construction is used having outer dimensions of 0.003 inches by 0.006 inches (applicable to the other thermocouple embodiments herein described), the use of a 0.007 inches PTFE beading mandrel in such a process is one illustrative example that is believed to be particularly suitable.

Moreover, and further to other appropriate embodiments herein shown and described, such thermocouple/balloon assembly has been observed to be suitable when forming the balloon 2602 from silicone rubber, such as is available from "Applied Silicones", PN 40000, formed according to the methods described with a wall thickness of approximately 0.015 inches in an uninflated condition and approximately 0.0025 inches in the inflated condition at 25 millimeters outer diameter. The channel 2624 may also be formed along the whole length of the balloon, and then sealed distally to the thermocouple 1806 and proximally over the thermocouple lead to complete the thermocouple/balloon subassembly. In one particular construction using the silicone material just described above, LocTite™ 4011 has been observed to be a suitable adhesive for these seals.

It is also to be understood that the methods of construction just described may also be applicable to the multi-layered balloon variation previously described, and in particular wherein the multi-layers are adhered or laminated to each other, as would be apparent to one of ordinary skill based upon this disclosure.

Further to the "thermocouple-imbedded-in balloon" variation just described by reference to FIGS. 26A–D, it has been observed that pressure within the balloon chamber 2610 may at times collapse inner and outer layers 2621, 2620 and close down channel 2624 over thermocouple 1806, thereby preventing the desired movement of thermocouple 1806 which in turn limits the balloon's expansion characteristics during inflation (see FIG. 26E). Therefore, FIG. 26F shows a further variation wherein an aperture or port 2605 is provided that allows for fluid communication between the channel 2624 and the inflation medium within the balloon chamber 2610. It is believed that such communication between these regions allows their respective pressures to equilibrate, such that the channel 2624 remains open and patent during inflation of the balloon. The port 2605 is formed by puncturing through the inner wall of the balloon 2602 until the channel 2624 communicates with the balloon chamber 2610.

As shown in FIG. 26G, the port 2605 is preferably formed along the proximal taper region of the balloon 2602, in part for reliability reasons so that the induced material flaw in the balloon from the puncture forming port 2605 is not provided along the high strain region of the working length of the balloon. Such positioning is also believed to aid in achieving the desired pressure equilibration whereas the thermocouple extends distally therefrom along the balloon and is pulled proximally in the direction of the port 2605 during inflation.

Figure 27B:
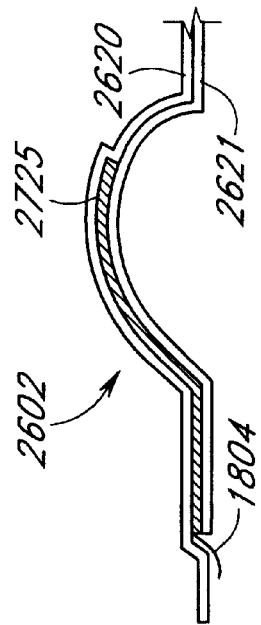
FIGS. 27A–B show partial axial cross-sectional (FIG. 27A) and longitudinal cross-sectional (FIG. 27B) views of another thermocouple/multi-layer balloon assembly wherein a stenting member is positioned within the thermocouple channel in order to prevent binding of the thermocouple during balloon inflation.
Figure 27A:
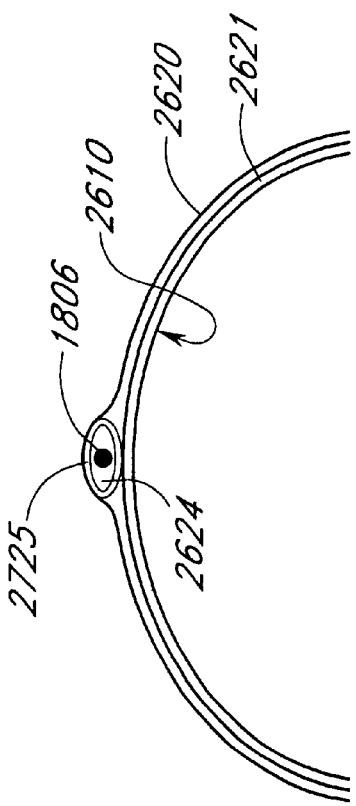

In addition or in the alternative to providing the pressure communication and equilibrium between the channel 2624 and the balloon chamber 2610, FIGS. 27A–B show an embodiment wherein a tube of material, such as, for example, polyimide material, is provided along the channel 2624 between the outer layer 2620 and the inner layer 2621. In this variation, the tube provides a stenting member 2725 for preventing collapse of the channel 2624 and maintaining patency of the channel during balloon inflation. Other "stenting member" variations may also be suitable substitutes for the particular embodiment shown in FIG. 27, such as, for example, by use of a coil or braid reinforcement within the inter-layer channel 2624.

FIGS. 28A–H show variations of a further mode for deploying a thermocouple at or near the balloon skin in a circumferential ablation device assembly, wherein the thermocouple members 2810a,b are "free-floating" within the balloon chamber in the sense that the thermocouples are deployable within the balloon chamber independently of the balloon skin and there is no direct coupling between the thermocouple and the balloon skin. It is believed that these embodiments allow for a more simple balloon construction than may be provided by other balloon/thermocouple designs.

Figure 28B:
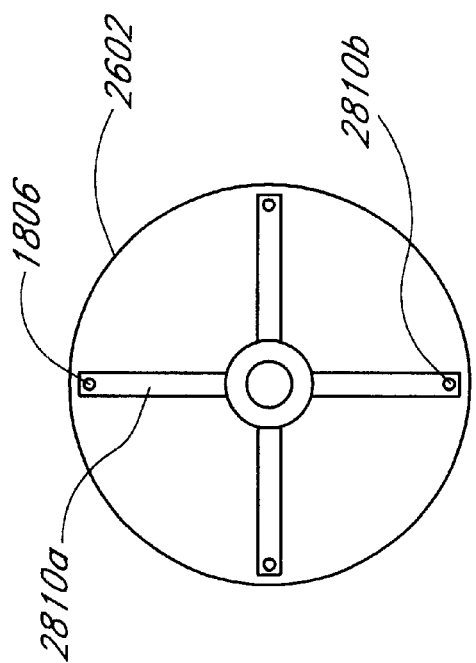
FIGS. 28A–B show partially cross-sectioned longitudinal (FIG. 28A) and axial (FIG. 28B) views of another mode for positioning a thermocouple at a desired location within a balloon of a circumferential ablation assembly, and variously show a plurality of thermocouples on spline members that have a first shape when the balloon is deflated and a second shape that positions the thermocouples at desired locations when the balloon in inflated.

In one regard, the thermocouple or thermocouples may be coupled to a delivery assembly which is in a collapsed state when the balloon is collapsed, and is adjustable to an expanded state when the balloon is inflated. For example, FIGS. 28A–D show various modes of such a thermocouple delivery assembly incorporating shaped or shapeable thermocouple splines 2810 that may be either self expanding, or that may be actuated to expand in order to mechanically deploy the thermocouple such as the thermocouple 1806 to the desired position such as against the balloon skin as shown in FIGS. 28B and D. Such deployment may be accomplished, for example, by incorporation of a superelastic alloy member into the spline, such as a nickle-titanium alloy that is preshaped to expand upon balloon inflation, or by incorporation of a shape-memory alloy, such as also for example a nickel-titanium alloy that may be heated either electrically or by conduction to take on the shape necessary to deploy the thermocouples (as shown).

Figure 28A:
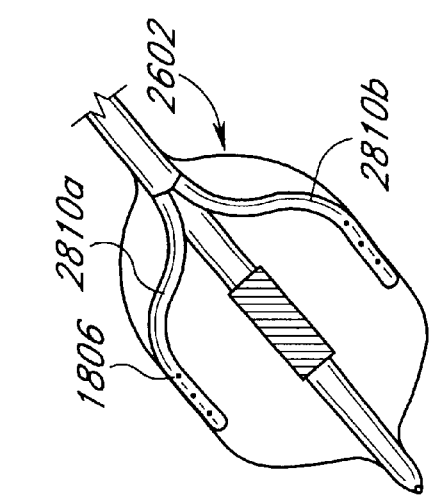
Figure 28C:
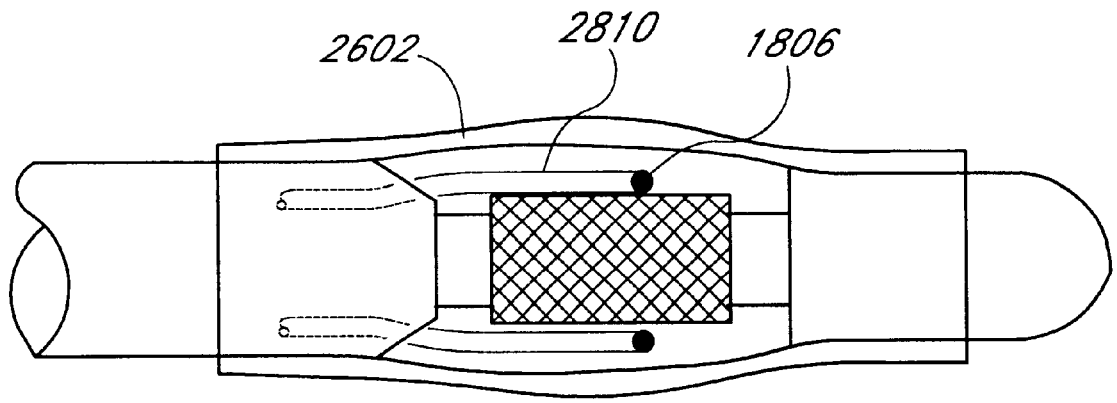
FIGS. 28C–D show partially sectioned longitudinal views of a thermocouple/balloon assembly similar to that shown in FIGS. 28A–B, although showing more detail regarding shaft construction of such assembly, and wherein FIG. 28D further shows a third thermocouple extending from one of the other thermocouples' spline members and positioned near an ultrasound transducer of the overall circumferential ablation member assembly.
Figure 28D:
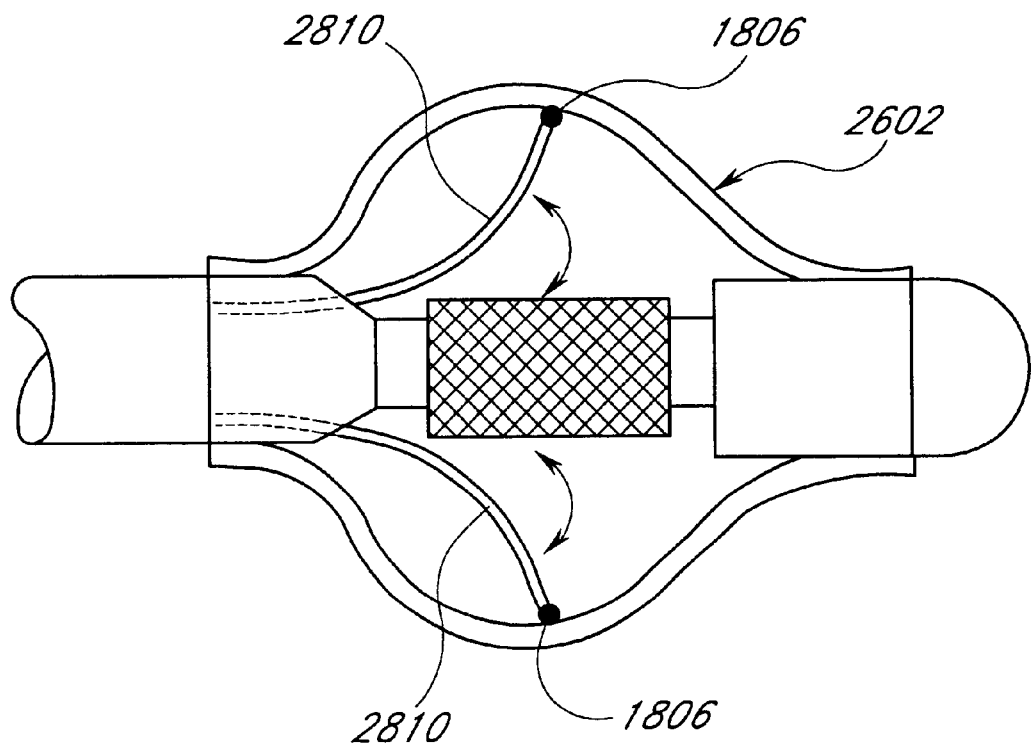
Figure 28E:
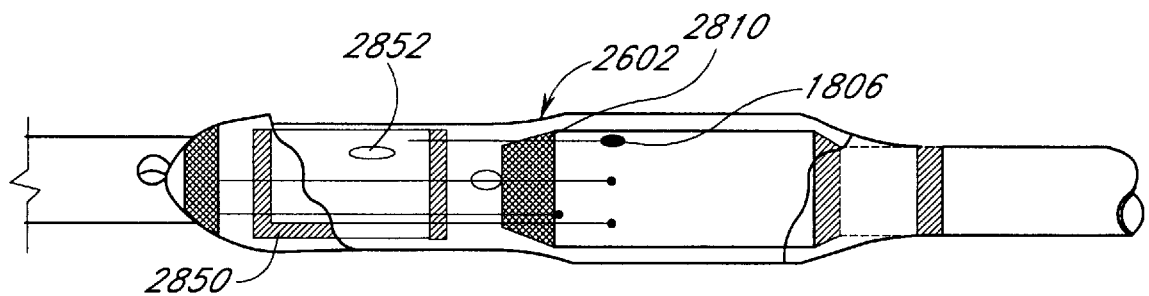
FIGS. 28E–F show partially sectioned longitudinal views of a thermocouple/balloon assembly wherein an internal balloon positioned within an external balloon and beneath the thermocouples is shown in a deflated mode for the assembly (FIG. 28E) and an inflated mode wherein the thermocouples are shown forced outwardly by the inflated internal balloon and against the inner surface of the inflated outer balloon's wall (FIG. 28F).
Figure 28F:
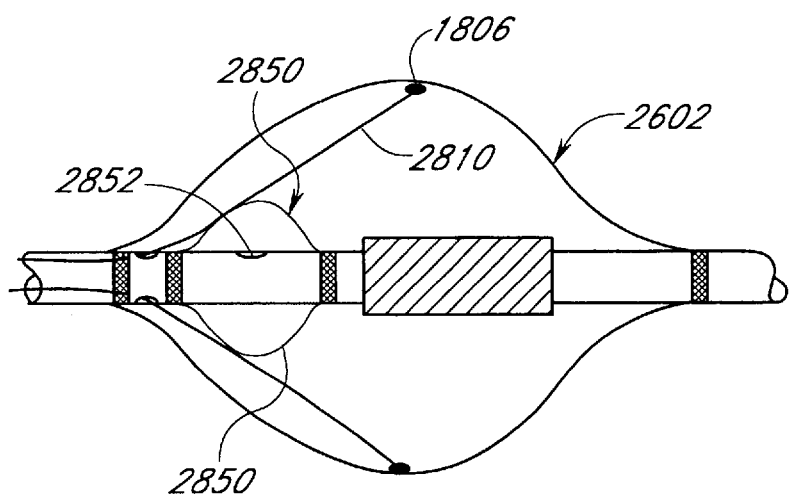

Another mode for independently deploying the thermocouples to interface with an expanded balloon skin is shown in FIGS. 28E–F, wherein an internal expandable member or balloon 2850 is positioned within the outer balloon 2602 and beneath the thermocouple spline 2810. The internal balloon 2850 inflates through the inflation port 2852 to push the thermocouple spline 2810 radially outwardly until the thermocouple 1806 provided along that spline is positioned as desired.

FIGS. 28G–H show a further embodiment wherein a mechanical means for deploying the thermocouple 1806 and the spline 2810 to the desired orientation and position within the balloon is incorporated into the wall of the balloon 2602. More specifically, the thermocouple spline 2810 is slideably housed within a channel 2860 (shown in shadow) that is positioned along the proximal taper 2809 (FIG. 28H). The spline 2810 extends distally from the channel 2860 at the port 2865 positioned along the proximal taper 2809 such that the thermocouple 1806 is free-floating within the chamber of the balloon 2602. Upon inflation of the balloon, the channel 2860 takes a radially deposed orientation with the proximal shoulder or taper 2809, and deploys with it in that orientation spline 2810, such that the thermocouple 1806 is forced against the inner wall of the balloon 2602, preferably along an ablation region for the purpose of temperature monitoring there, as is shown in FIG. 28H.

FIGS. 29A–B show an alternative technique for attaching thermocouples or electrodes to a catheter 2601 and the balloon 2602. In FIG. 29A, one or more elongated flexible members 2910 are disposed around the balloon 2602. While the members 2910 are herein described in one illustrative embodiment as being relatively "flexible", the present invention contemplates that the members 2910 need not necessarily be flexible, and in some particular embodiments may be preferably relatively stiff in order to provide a controlled motion and positioning when the balloon 2602 is inflated. Each elongated flexible member 2910 is attached to the catheter shaft 2601 proximal to the balloon 2602, and each elongated flexible member 2910 is attached to the catheter shaft 2601 distal to the balloon 2602. Each elongated flexible member 2910 includes one or more thermocouples 1806 and thermocouple wires. The elongated flexible members can be constructed: as tubes with the thermocouples and thermocouple wires inside the tube; as flexible printed circuits; as bundles of thermocouples and thermocouple wires, etc. When the balloon 2602 expands, it presses the elongated flexible members 2910 against the inner wall of the pulmonary vein.

In one embodiment, the elongated flexible members 2910 are attached to the catheter shaft 1801 with enough slack to allow the balloon 2602 to expand properly. In one a embodiment, the elongated flexible members 2910 are provided with sufficient stretch to allow the balloon 2602 to expand properly. In one embodiment, shown in FIG. 29B, the elongated flexible members 2910 are provided with a stretchable zone 2950 to allow the elongated flexible members 2910 to accommodate the expansion of the balloon 2602. The proximal ends of the elongated flexible members 2910 are attached to the catheter body 2601.

Figure 30:
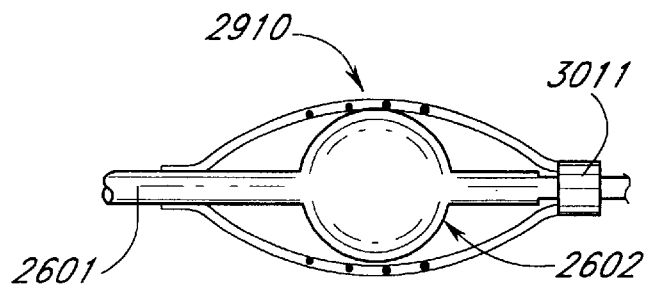
FIG. 30 shows a longitudinal perspective view of another thermocouple/balloon assembly which is similar to those shown in FIGS. 29A–B, except that FIG. 30 shows the distal ends of the elongated thermocouple members attached to a slideable collar disposed around the ablation catheter shaft distal to the balloon.

In an additional embodiment, shown in FIG. 30, the distal ends of the elongated flexible members 2910 are attached to a slideable collar 3011 disposed around the catheter shaft 2601 distal to the balloon 2602. The sliding collar 3011 slides longitudinally along the catheter shaft 2601, thereby allowing the elongated flexible members 2910 to accommodate the expansion of the balloon 2602.

The elongated flexible members 2910, being external to the balloon 2602, can be provided with either or both of the thermocouples and electrodes. The thermocouples can be used for measuring position of the balloon, as discussed above, and for monitoring the ablation process, as discussed above. The electrodes can be used for ablation, as discussed above, and for mapping the electrical properties of tissue, such as along the wall of the pulmonary vein either along an ablation region or distal or proximally thereto.

Figure 31:
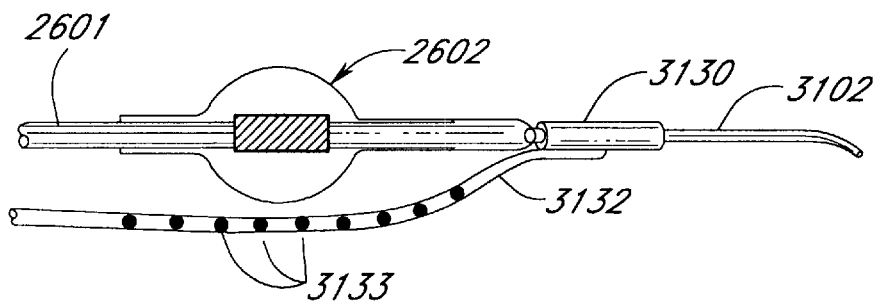
FIG. 31 shows a longitudinal perspective view of a temperature-sensing circumferential catheter system wherein the distal end of a temperature-sensing catheter is attached to a collar disposed around a guide member that protrudes from the distal end of a separate circumferential ablation catheter.

FIG. 31 shows an ablation catheter system that uses a separate temperature catheter (or wire) 3132 in addition to the catheter shaft 2601 and the balloon 2602. The distal end of the temperature catheter 3132 is attached to a collar 3130 disposed around a guide wire 3102 that protrudes from the distal end of the catheter shaft 2601. The temperature catheter 3132 includes one or more thermocouples (or electrodes) 3133.

In one surgical procedure, the guide wire 3102 is introduced into the pulmonary vein. The temperature catheter 3132 is then deployed over the guide wire 3102. After the temperature catheter 3132 is in position in the pulmonary vein, the ablation catheter 2601 is deployed over the guide wire 3102. The thermocouples 3133 on the temperature catheter 3132 may be used to position the ablation catheter 2601 at a desired location for ablation, as previously described for the position monitoring assemblies above (this applies to the other temperature monitoring embodiments as well). The temperature catheter 3132 is also used to provide temperature feedback during the ablation process. The temperature catheter 3132 can also be provided with electrodes to map the conductivity of the pulmonary vein ostium both before and after ablation, as elsewhere herein described.

Figure 32:
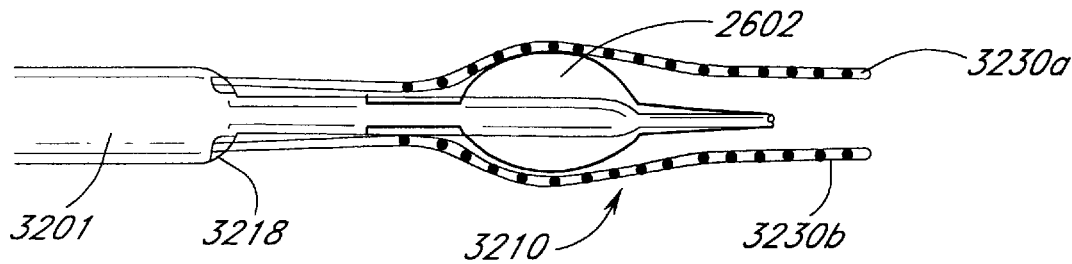
FIG. 32 shows a longitudinal perspective view of an ablation catheter system having steerable deployable temperature sensing members extending from lumens in the catheter shaft.

FIG. 32 shows an ablation catheter system having a catheter shaft 3201, the balloon 2602, and one or more deployable temperature members 3210. Each deployable temperature member 3210 is slideably disposed in a lumen in the catheter shaft 3201 and is deployed outward from a port 3218 in the lumen such that the deployable temperature member 3210 can be slideably deployed and controlled from the proximal end of the catheter shaft 3201. Each deployable temperature members 3210 is typically deployed such that the distal end of the deployable temperature member 3210 is distal to the balloon 2602. One or more temperature sensors (e.g. thermocouples) in the deployable temperature members 3210 provide temperature feedback used to measure position of the ablation catheter and/or monitor the ablation process.

Figure 33:
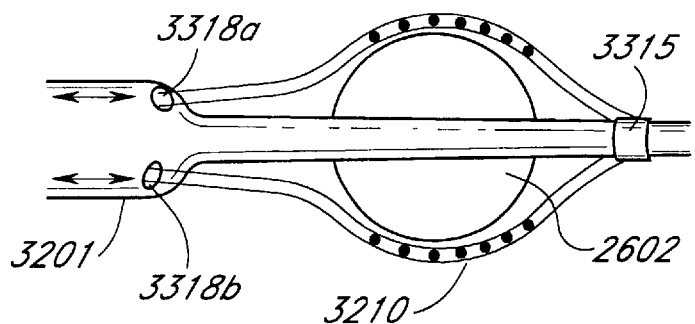
FIG. 33 shows a longitudinal perspective view of an ablation catheter system having deployable temperature members slideably deployed and controlled from the proximal end of the catheter shaft, where the distal end of each of each deployable temperature member is attached to a collar slideably disposed on the catheter shaft.

In one embodiment, such as that shown in FIG. 32, each deployable temperature member 3210 is provided with a steerable tip 3230$a,b$ that allows the deployable temperature member to be desirably maneuvered inside the patient. In another embodiment, such as that shown in FIG. 33, the distal end of each of the deployable temperature members 3210 is attached to a portion of the catheter shaft 3201 distal to the balloon 2602. The deployable temperature members 3210 can be fixedly attached to the catheter shaft 3201 or slideably attached to the catheter shaft 3201 (e.g. attached to a collar 3315 that is slideably disposed about the catheter shaft 3201). In this embodiment, the temperature members slide through the openings 3318$a,b$ in the catheter shaft 3201.

Figure 34A:
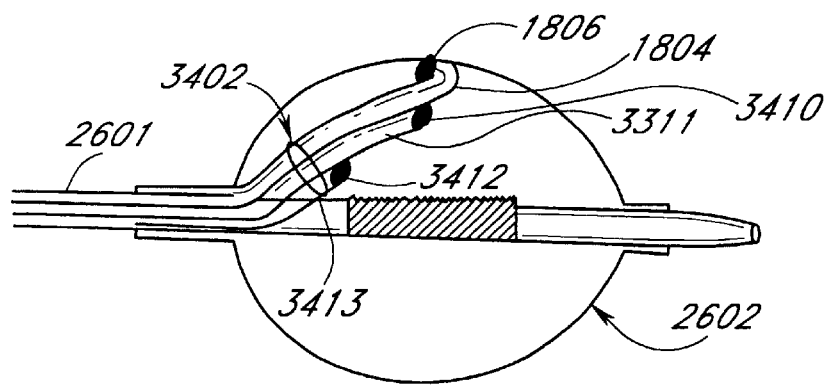
FIG. 34A shows an ablation catheter having a thermocouple bundle disposed within an expandable member, where the thermocouples are positioned to provide a profile of the temperatures inside the expandable member.
Figure 34B:
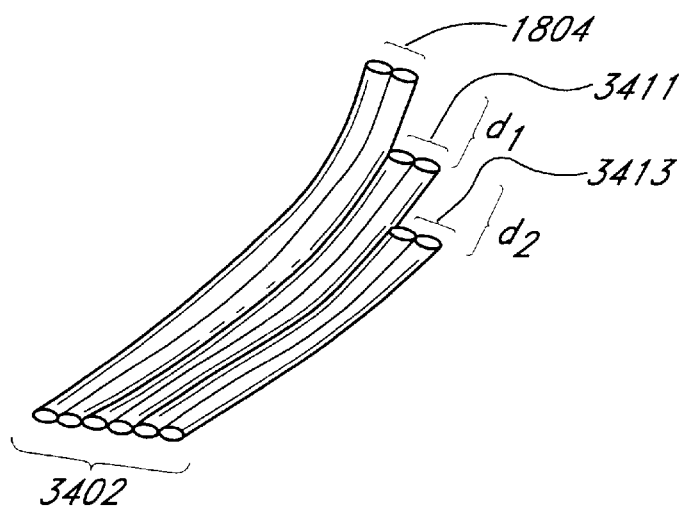
FIG. 34B shows additional details of the thermocouple bundle shown in FIG. 34A.

The use of thermocouples inside an expandable member (e.g., a balloon), as shown, for example, in FIGS. 18A–K, is not limited to thermocouples attached to the balloon, but includes thermocouples disposed inside the balloon as shown in FIGS. 34A–B. FIG. 34A shows the catheter shaft 2601, the balloon 2602, the thermocouple wire 1804, and the thermocouple 1806. FIG. 34A also shows additional thermocouple wires 3411, 3413 provided to additional thermocouples 3410, 3412, respectively. The thermocouple wires 1804, 3411 and 3413 are members of a thermocouple bundle 3402 as shown in FIG. 34B. Each thermocouple has two terminals. The thermocouple wire 1804 includes two conductors for the thermocouple 1806. The thermocouple wire 3411 includes two conductors for the thermocouple 3410. The thermocouple wire 3413 includes two conductors for the thermocouple 3412.

Alternatively, the first terminal of each of the thermocouples 1804, 3410 and 3412 can be provided to common thermocouple bus (not shown) and the second terminal of the thermocouples 1806, 3410 and 3412 are provided to single-conductor embodiments of the thermocouple wires 1804, 3411 and 3413, respectively. The thermocouples are staggered in the bundle 3402, such that the when the balloon 2602 is expanded, the thermocouple 3412 is positioned relatively near the shaft 2601 inside the balloon 2602, and the thermocouple 3410 is positioned between thermocouples 1806 and 3412.

The thermocouples 1806, 3410 and 3412, being positioned at different locations inside the balloon 2602, are useful for measuring an axial temperature gradient across the balloon 2602. The temperature of the wall of the pulmonary vein that is in contact with the balloon 2602 near the thermocouple 1806 can typically be calculated relatively more accurately by using the axial temperature gradient than can be calculated by using the temperature measured by the thermocouple 1806 alone.

In particular, where a thermocouple is positioned within the path of ablative coupling between an ablation element within the balloon and the balloon/tissue interface, there may be false temperature readings for that thermocouple due to a response of the thermocouple itself to the ablation energy (e.g. ultrasonic heating of the thermocouple within an ultrasonic ablation energy path may heat the thermocouple to a greater temperature than its surroundings). In this case, providing multiple thermocouples at different locations and comparing their operating parameters (e.g. response times, etc.) may provide useful information to allow certain such variables to be filtered and thereby calculate an accurate temperature at the thermocouple location.

Figure 35:
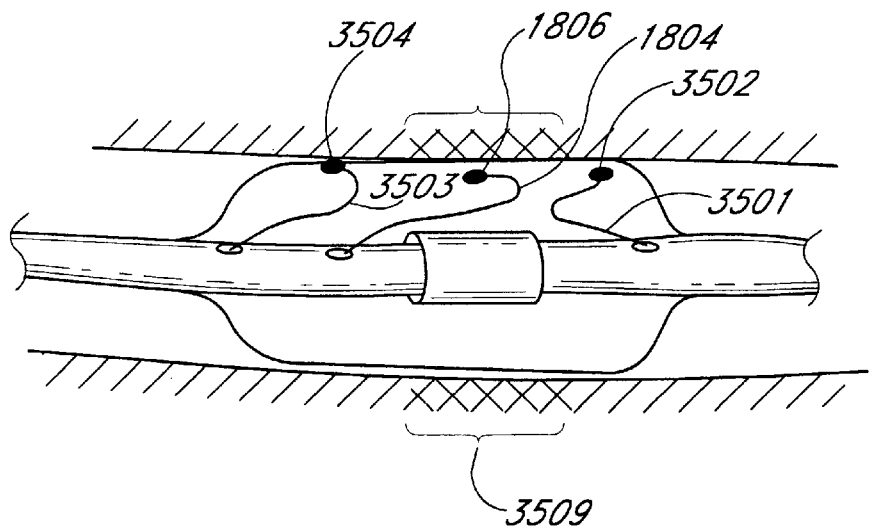
FIG. 35 shows a circumferential ablation catheter system provided with a thermocouple sensor between two external electrodes positioned along the balloon's working length to be used for mapping the conductivity of the pulmonary vein and to ascertain the effectiveness of the ablation.

As shown in FIG. 35, an ablation catheter system can be provided with electrodes to be used for mapping the conductivity of the pulmonary vein and to ascertain the effectiveness of the ablation. FIG. 35 shows the catheter shaft 2601, the balloon 2602, the thermocouple wire 1804, and the thermocouple 1806. FIG. 35 also shows a distal electrode 3502 and a proximal electrode 3504. The distal electrode is distal to an ablated region of the tissue 3509 and the proximal electrode is proximal to the ablated region 3509. According to this orientation, the distal and proximal electrodes 3502, 3504 are positioned to allow the monitoring of an action potential across the ablation zone where the thermocouple is located, thereby enabling a user to confirm formation of a conduction block either during or after performing an ablation procedure with the assembly.

Figure 36:
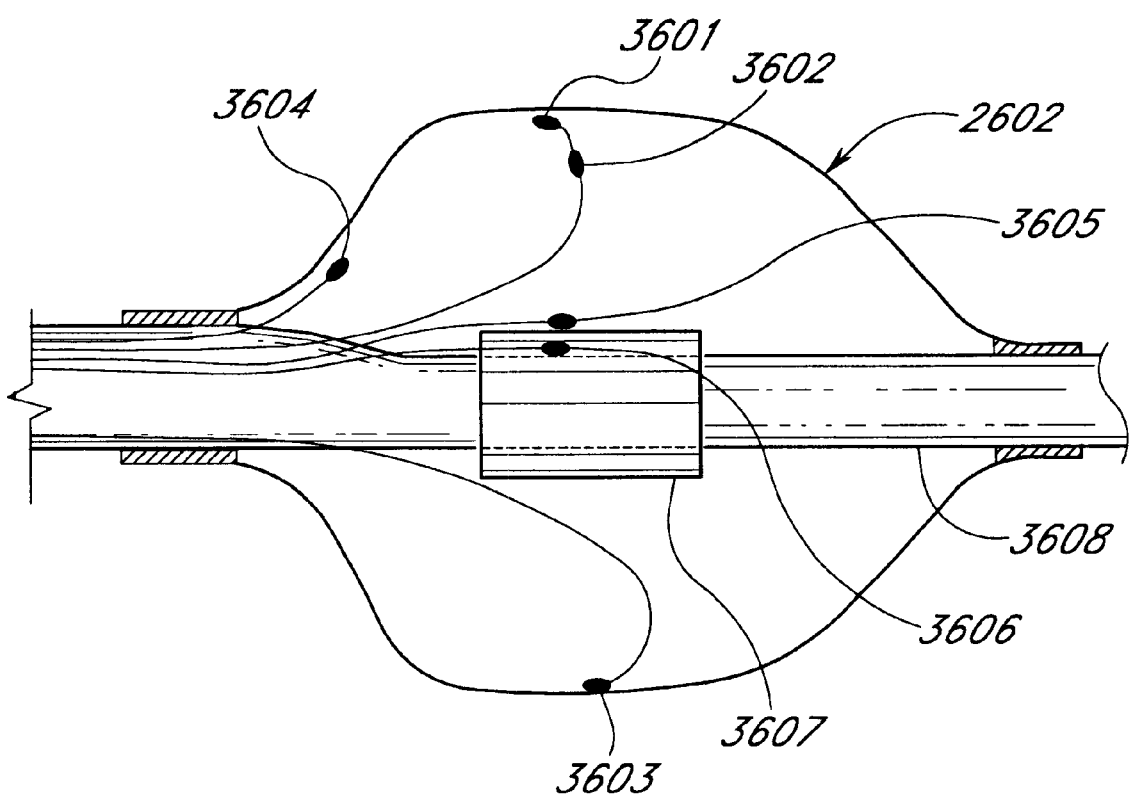
FIG. 36 shows a further assembly of multiple thermocouples at particular positions within a balloon member in order to monitor various parameters during operation of a circumferential ablation catheter system.

FIG. 36 further shows one particular arrangement of thermocouples within a balloon-based circumferential ablation member that incorporates an ultrasound ablation element 3607, such as previously described above. More specifically, the thermocouples 3601 and 3603 are secured to the interior wall of the balloon 2602 with a 180° separation about the circumference of the balloon, each thermocouple being secured to the balloon in an orientation previously discussed above that allows for a loop in the associated leads to provide slack and a robust coupling during balloon inflation. The thermocouple 3602 is coupled to a common delivery member with the thermocouple 3601 and is spaced from the thermocouple 3601 sufficiently to allow for a comparison of temperature at the tissue interface and within the ultrasound ablation path in the balloon inflation medium, such as for example with a separation of approximately 2 millimeters. In one construction, these two thermocouples may be provided as a twisted pair of bifilar leads. The thermocouple 3604 is positioned along the proximal taper of the balloon 2602 for the purpose of monitoring general balloon temperature outside of the ablation zone (circumferential pattern of radiating energy from the ablation element 3607), and may be secured to the inner surface of the taper by adhesive or as otherwise described for the various embodiments above. The thermocouple 3606 is positioned underneath the ultrasound ablation element 3607 (or may be between the ablation element and a spline member, or between the spline member and the inner catheter member 3608 according to the detailed ultrasound constructions described above), in order to monitor the operating parameters of the transducer such as for safety and operating efficiency purposes. The thermocouple 3605 is secured to an outer surface of a PET member that covers the transducer ablation element 3607 for a similar purpose as the thermocouple 3606.

It is believed that this particular arrangement provides a useful array of data points for monitoring various aspects of the ablation member during ablation, as just described by way of examples for each thermocouple. However, various modifications to this particular arrangement of the transducer array may be made without departing from the scope of the invention, as is evidenced in part by the other embodiments. For example, it is believed that providing three thermocouples along the balloon/tissue interface at 120° radial separation may provide a high degree of confidence in monitoring complete circumferentiality of ablation during certain ablation procedures in and around pulmonary veins, although the two-thermocouple at 180° separation shown is believed to be adequate in many if not most applications.

Figure 37:
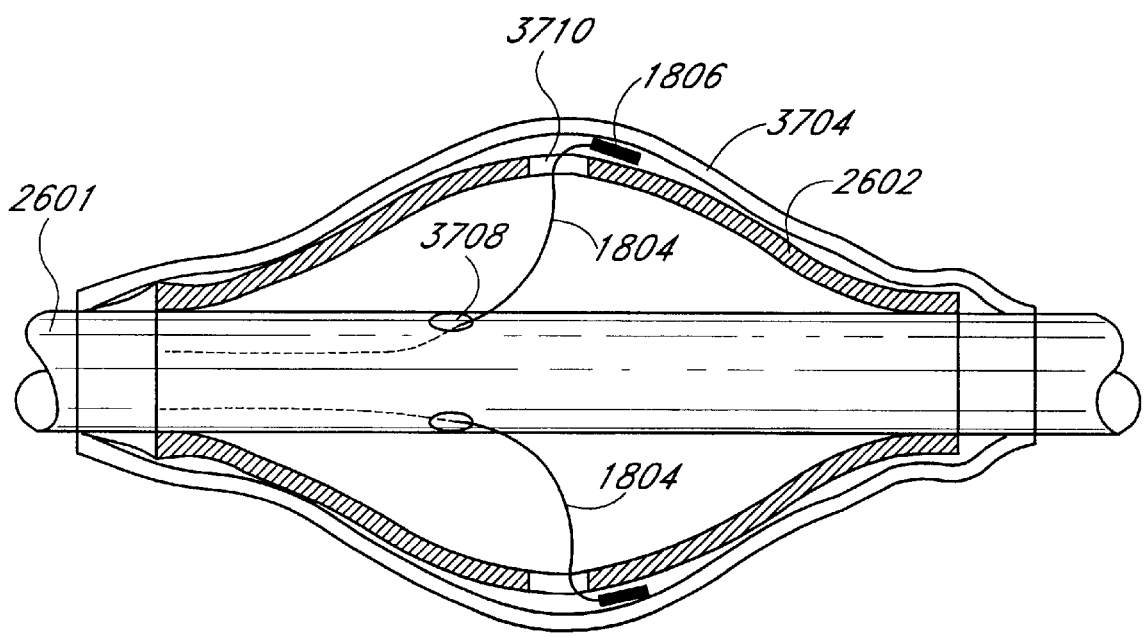
FIG. 37 shows a device of a circumferential ablation catheter provided with a multi-layer balloon having thermocouples affixed between the balloon layers.

FIG. 37 provides another embodiment of a particular arrangement of thermocouples mounted between the balloon wall 2602 and a silicon layer 3704 of a balloon-based circumferential ablation member. As illustrated, the thermocouple wires 1804 run from the orifices 3708 in the catheter shaft 2601 through the holes 3710 in the balloon wall 2602.

The embodiment illustrated in FIG. 37 can be manufactured by drilling or punching the hole 3710 through the balloon 2602 in order to provide a passageway for the thermocouple wires 1804. The thermocouple 1806 is then threaded from the interior of the balloon 2602 to the exterior of the balloon 2602. It should be noted that the thermocouple wires 1804 traverse the hole 3710 in order to enter the interior of the catheter shaft 2601. The thermocouple 1806 is then affixed to the exterior of the balloon by an adhesive or other compound, as discussed previously. The balloon/thermocouple combination is then dipped into a silicone bath to create the layer of silicone 3704 covering the thermocouple 1806.

While the above-description of the sensory system need not be used with an ablation catheter, the embodiments described herein are believed to be particularly useful in catheter assemblies which are specifically adapted for ablating tissue along a region where a pulmonary vein extends from a left atrium in the treatment of atrial fibrillation, as noted above. Therefore, the assemblies and methods of the present invention are also contemplated for use in combination with, or where appropriate in the alternative to, the various particular features and embodiments shown and described in the following co-pending U.S. Patent Applications that also address circumferential ablation at a location where a pulmonary vein extends from an atrium: U.S. Ser. No. 08/889,798 for "CIRCUMFERENTIAL ABLATION DEVICE ASSEMBLY" to Lesh et al., filed Jul. 8, 1997, now U.S. Pat. No. 6,024,740, issued Feb. 15, 2000; U.S. Ser. No. 08/889,835 for "DEVICE AND METHOD FOR FORMING A CIRCUMFERENTIAL CONDUCTION BLOCK IN A PULMONARY VEIN" to Lesh, filed Jul. 8, 1997; U.S. Ser. No. 09/199,736 for "CIRCUMFERENTIAL ABLATION DEVICE ASSEMBLY" to Diederich et al., filed Feb. 3, 1998; and U.S. Ser. No. 09/260,316 for "DEVICE AND METHOD FOR FORMING A CIRCUMFERENTIAL CONDUCTION BLOCK IN A PULMONARY VEIN" to Lesh. The disclosures of these references are herein incorporated in their entirety by reference thereto.

It is further contemplated that the embodiments shown and described herein may be combined, assembled together, or where appropriate substituted for, the various features and embodiments which are disclosed in the following co-pending provisional and non-provisional U.S. Patent Applications: the co-pending provisional U.S. Patent Application for "FEEDBACK APPARATUS AND METHOD FOR ABLATION AT PULMONARY VEIN OSTrUM", filed on the same day as this Application, co-pending Provisional U.S. Patent Application No. 60/122,571, for "FEEDBACK APPARATUS AND METHOD FOR ABLATION AT PULMONARY VEIN OSTIUM", filed on Mar. 2, 1999; co-pending Provisional U.S. Patent Application No. 60/133,610 for "BALLOON ANCHOR WIRE", filed May 11, 1999; the co-pending non-provisional U.S. Patent Application for "TISSUE ABLATION DEVICE ASSEMBLY AND METHOD FOR ELECTRICALLY ISOLATING A PULMONARY VEIN OSTIUM FROM A POSTERIOR LEFT ATRIAL WALL", filed on the same day as this Application, and which claims priority to Provisional U.S. Patent Application No. 60/133,677, filed May 11, 1999; the co- pending non-provisional U.S. Patent Application for "APPARATUS AND METHOD INCORPORATING AN ULTRASOUND TRANSDUCER ONTO A DELIVERY MEMBER", filed on the same day as this Application, and which claims priority to Provisional U.S. Patent Application No. 60/133,680, filed May 11, 1999; and co-pending Provisional U.S. Patent Application Serial No. 60/133,807 for "CATHETER POSITIONING SYSTEM". The disclosures of these references are herein incorporated in their entirety by reference thereto.

In addition, such a circumferential ablation device assembly may be used in combination with other linear ablation assemblies and methods, and various related components or steps of such assemblies or methods, respectively, in order to form a circumferential conduction block adjunctively to the formation of long linear lesions, such as in a less-invasive "maz"-type procedure. Examples of such assemblies and methods related to linear lesion formation and which are contemplated in combination with the presently disclosed embodiments are shown and described in the following additional co-pending U.S. Patent Applications and Patents: U.S. Pat. No. 5,971,983, issued on Oct. 26, 1999, entitled "TISSUE ABLATION DEVICE AND METHOD OF USE" filed by Lesh on May 9, 1997; U.S. Ser. No. 09/260,316 for "TISSUE ABLATION SYSTEM AND METHOD FOR FORMING LONG LINEAR LESION" to Langberg et al., filed May 1, 1999; and U.S. Ser. No. 09/073,907 for "TISSUE ABLATION DEVICE WITH FLUID IRRIGATED ELECTRODE", to Schaer et al., filed May 6, 1998. The disclosures of these references are herein incorporated in their entirety by reference thereto.

While a number of variations of the invention have been shown and described in detail, other modifications and methods of use contemplated within the scope of this invention will be readily apparent to those of skill in the art based upon this disclosure. It is contemplated that various combinations or sub-combinations of the specific embodiments may be made and still fall within the scope of the invention. For example, the embodiments variously shown to be "guidewire" tracking variations for delivery into a left atrium and around or within a pulmonary vein may be modified to instead incorporate a deflectable/steerable tip instead of guidewire tracking and are also contemplated. Moreover, all assemblies described are believed useful when modified to treat other tissues in the body, in particular other regions of the heart, such as the coronary sinus and surrounding areas. Further, the disclosed assemblies may be useful in treating other conditions, wherein aberrant electrical conduction may be implicated, such as for example, heart flutter. Indeed, other conditions wherein catheter-based, directed tissue ablation may be indicated, such as for example, in the ablation of fallopian tube cysts. Accordingly, it should be understood that various applications, modifications and substitutions may be made of equivalents without departing from the spirit of the invention or the scope of the following claims.

We claim:

1. A medical article comprising:
   an elongate body with a proximal end portion and a distal end portion;
   an expandable member coupled to the distal end portion of the elongate body and having a tube disposed along an inner surface, wherein the expandable member is adjustable from a collapsed position to an expanded position;
   a sensor slidably disposed in the tube and thereby coupled to the expandable member at a location; and
   a conductor coupled to a coupler at the proximal end portion of the elongated body and to the sensor in a manner that does not substantially affect the adjustment of the expandable member from the collapsed position to the expanded position.

2. The apparatus of claim 1, wherein the expandable member comprises an inflatable balloon.

3. The apparatus of claim 1, wherein the tube is formed through an adhesive disposed along the inner surface.

4. The apparatus of claim 3, wherein the adhesive encapsulates the tube.

5. The apparatus of claim 1, wherein the conductor is shaped so as to reduce tension at the location when the expandable member is adjusted between the collapsed position and the expanded position.

6. The apparatus of claim 5, wherein the conductor forms a loop extending through the tube.

7. The apparatus of claim 5, wherein the conductor forms a helix that reduces tension on the location at which the sensor is coupled to the expandable member.

8. The apparatus of claim 1, wherein the location on the expandable member further comprises a reinforcement disposed on an outer surface of the expandable member.

9. The apparatus of claim 1, wherein the conductor further comprises means for reducing tension on said location when the expandable member is adjusted from the collapsed position to the expanded position.

10. The apparatus of claim 1, wherein the expandable member comprises a spline.

11. The apparatus of claim 1, wherein the sensor comprises a temperature sensor.

12. The apparatus of claim 11 additionally comprising an ablation element that is coupled to the distal end of the portion the elongated body.

13. A tissue ablation apparatus for ablating a substantial portion of a circumferential region of tissue at a body location where a pulmonary vein extends from an atrium, comprising:
   an elongate body with a proximal end portion and a distal end portion;
   an ablation member coupled to the elongate body and comprising:
      an expandable member coupled to the distal end portion of the elongate body, wherein the expandable member is adjustable from a collapsed position to an expanded position and the expandable member has an outer surface that is adapted to contact at least the substantial portion of the circumferential region of tissue along an ablative path when the expandable member is adjusted to the expanded position;
      an ablation element that is adapted to ablate at least a portion of the substantial portion of the circumferential region of tissue;
      a sensor coupled to the expandable member at a location at least when the expandable member is in the expanded position;
      a conductor coupled to a coupler at the proximal end portion of the elongated body and to the sensor in a manner that does not substantially affect the adjustment of the expandable member from the collapsed position to the expanded position; and
      at least one elongated member adapted to at least partially overlie the expandable member, the sensor being positionable along an outside surface of the expandable member within the ablative path when the expandable member is in its expanded position.

14. The apparatus of claim 13, wherein the elongated member is flexible.

15. The apparatus of claim 13, wherein the sensor is fixed to the elongated member.

16. tissue ablation apparatus for ablating a substantial portion of a circumferential region of tissue at a body location where a pulmonary vein extends from an atrium, comprising:
- an elongate body with a proximal end portion and a distal end portion;
- an ablation member coupled to the elongate body and comprising:
  - an expandable member coupled to the distal end portion of the elongate body, wherein the expandable member is adjustable from a collapsed position to an expanded position and the expandable member has an outer surface that is adapted to contact at least the substantial portion of the circumferential region of tissue along an ablative path when the expandable member is adjusted to the expanded position;
  - an ablation element that is adapted to ablate at least a portion of the substantial portion of the circumferential region of tissue;
  - a electrode coupled to the expandable member at a location at least when the expandable member is in the expanded position; and
  - a conductor coupled to a coupler at the proximal end portion of the elongated body and to the electrode in a manner that does not substantially affect the adjustment of the expandable member from the collapsed position to the expanded position.

17. A tissue ablation apparatus for ablating a substantial portion of a circumferential region of tissue at a body location where a pulmonary vein extends from an atrium comprising:
- an elongate body with a proximal end portion and a distal end portion;
- an ablation member coupled to the elongate body and comprising:
  - an expandable member coupled to the distal end portion of the elongate body and having an outer layer and an inner layer, wherein the expandable member is adjustable from a collapsed position to an expanded position in which the outer layer is adapted to contact the substantial portion of the circumferential region of tissue;
  - an ablation element that is adapted to ablate at least a portion of the substantial portion of the circumferential region of tissue;
  - a sensor disposed between the inner and outer layers and coupled to the expandable member at a location at least when the expandable member is in the expanded position;
  - a passageway between the outer layer and the inner layer, wherein the sensor is slideably engaged within the passageway; and
  - a conductor coupled to a coupler at the proximal end portion of the elongated body and to the sensor in a manner that does not substantially affect the adjustment of the expandable member from the collapsed position to the expanded position.

18. The apparatus of claim 17, wherein the passageway is filled with a fluid.

19. A tissue ablation apparatus for ablating a substantial portion of a circumferential region of tissue at a body location where a pulmonary vein extends from an atrium, comprising:
- an elongate body with a proximal end portion and a distal end portion;
- an ablation member coupled to the elongate body and comprising:
  - an expandable member coupled to the distal end portion of the elongate body and including a passageway, wherein the expandable member is adjustable from a collapsed position to an expanded position in which the expandable member is adapted to engage the substantial portion of the circumferenital region of tissue;
  - an ablation element that is adapted to ablate at least a portion of the substantial portion of the circumferential region of tissue;
  - a sensor coupled to the expandable member at a location at least when the expandable member is in the expanded position; and
  - a conductor coupled to a coupler at the proximal end portion of the elongated body and to the sensor;
  - wherein the sensor and the conductor are slideably engaged within the passageway of the expandable member in a manner that does not substantially affect the adjustment of the expandable member from the collapsed position to the expanded position.

20. The apparatus of claim 19, wherein the expandable member has an interior space which is in fluid communication with the passageway.

21. The apparatus of claim 20, wherein the passageway further comprises a stenting member.

22. A tissue ablation apparatus for ablating a substantial portion of a circumferential region of tissue at a body location where a pulmonary vein extends from an atrium, comprising:
- an elongate body with a proximal end portion and a distal end portion;
- an ablation member coupled to the elongate body and comprising:
  - an expandable member coupled to the distal end portion of the elongate body, wherein the expandable member is adjustable from a collapsed position to an expanded position in which the expandable member is adapted to engage the substantial portion of the circumferenital region of tissue;
  - an ablation element that is adapted to ablate at least a portion of the substantial portion of the circumferential region of tissue;
  - an electrode coupled to the expandable member at a location at least when the expandable member is the expanded position; and
  - a conductor coupled to a coupler at the proximal end portion of the elongated body and to the electrode in a manner that does not substantially affect the adjustment of the expandable member from the collapsed position to the expanded position.

23. A tissue ablation apparatus for ablating a substantial portion of a circumferential region of tissue at a body location where a pulmonary vein extends from an atrium, comprising:
- an elongate body with a proximal end portion and a distal end portion;
- an ablation member coupled to the elongate body and comprising:
  - an expandable member coupled to the distal end portion of the elongate body, wherein the expandable member is adjustable from a collapsed position to an expanded position in which the expandable member is adapted to engage the substantial portion of the circumferenital region of tissue;
  - an ultrasonic transducer that is adapted to ablate at least a portion of the substantial portion of the circumferential region of tissue;

a sensor coupled to the expandable member at a location at least when the expandable member is in the expanded position; and a conductor coupled to a coupler at the proximal end portion of the elongated body and to the sensor in a manner that does not substantially affect the adjustment of the expandable member from the collapsed position to the expanded position.

24. A medical article comprising:

an elongate body with a proximal end portion and a distal end portion;

an expandable member coupled to the distal end portion of the elongate body and having an outer layer and an inner layer, wherein the expandable member is adjustable from a collapsed position to an expanded position;

a passageway disposed between the outer layer and the inner layer;

a sensor slideably engaged within the passageway and coupled to the expandable member at a location at least when the expandable member is in the expanded position; and a conductor coupled to a coupler at the proximal end portion of the elongated body and to the sensor in a manner that does not substantially affect the adjustment of the expandable member from the collapsed position to the expanded position.

25. The apparatus of claim 24, wherein the passageway is filled with a fluid.

26. A medical article comprising:

an elongate body with a proximal end portion and a distal end portion;

an expandable member coupled to the distal end portion of the elongate body and having a passageway, wherein the expandable member is adjustable from a collapsed position to an expanded position;

a sensor coupled to the expandable member at a location at least when the expandable member is in the expanded position; and a conductor coupled to a coupler at the proximal end portion of the elongated body and to the sensor;

wherein the sensor and the conductor are slideably engaged within the passageway in a manner that does not substantially affect the adjustment of the expandable member from the collapsed position to the expanded position.

27. The apparatus of claim 26, wherein the expandable member has an interior space which is in fluid communication with the passageway.

28. The apparatus of claim 27, wherein the passageway further comprises a stenting member.

29. A tissue ablation apparatus for ablating a substantial portion of a circumferential region of tissue at a body location where a pulmonary vein extends from an atrium, comprising:

an elongate body with a proximal end portion and a distal end portion;

an ablation member coupled to the elongate body and comprising:

an expandable member coupled to the distal end portion of the elongate body, wherein the expandable member is adjustable from a collapsed position to an expanded position, the expandable member having an inner layer and an outer layer, the outer layer having an outer surface adapted to contact the circumferential region of tissue;

an ablation element disposed within an interior of the expandable member, the ablation element being adapted to ablate at least a portion of the circumferential region of tissue;

a sensor slidably disposed between the inner layer and outer layer of the expandable member at a location at least when the expandable member is in the expanded position; and a conductor coupled to a coupler at the proximal end portion of the elongated body and to the sensor in a manner that does not substantially affect the adjustment of the expandable member from the collapsed position to the expanded position.

30. A tissue ablation apparatus for ablating a substantial portion of a circumferential region of tissue at a body location where a pulmonary vein extends from an atrium, comprising:

an elongate body with a proximal end portion and a distal end portion;

an ablation member coupled to the elongate body and comprising:

an inflatable balloon coupled to the distal end portion of the elongate body and including a spline, wherein the inflatable balloon is adjustable from a collapsed position to an expanded position in which the inflatable balloon is adapted to engage the circumferential region of tissue;

an ultrasound transducer adapted to emit a circumferential path of ultrasound ablative energy for ablating at least a portion of the circumferential region of tissue;

a sensor coupled to the inflatable balloon along the spline when the inflatable balloon is in the expanded position, the sensor being positionable within the circumferential path when the expandable member is in the expanded position; and a conductor coupled to a coupler at the proximal end portion of the elongated body and to the sensor in a manner that does not substantially affect the adjustment of the inflatable balloon from the collapsed position to the expanded position.

* * * * *

UNITED STATES PATENT AND TRADEMARK OFFICE
CERTIFICATE OF CORRECTION

PATENT NO. : 6,547,788 B1
DATED : April 15, 2003
INVENTOR(S) : Maguire et al.

It is certified that error appears in the above-identified patent and that said Letters Patent is hereby corrected as shown below:

<u>Title page,</u>
Item [73], Assignee, should read -- Atrionix, Inc., Palo Alto, CA (US) --

Signed and Sealed this

Twenty-sixth Day of August, 2003

JAMES E. ROGAN
*Director of the United States Patent and Trademark Office*